United States Patent
Marroquin Belaunzaran et al.

(10) Patent No.: US 11,807,676 B2
(45) Date of Patent: Nov. 7, 2023

(54) MHC CLASS IA OPEN CONFORMERS

(71) Applicants: UNIVERSITAT ZURICH, Zurich (CH); UNIVERSITAT BASEL, Basel (CH)

(72) Inventors: Osiris Marroquin Belaunzaran, Zurich (CH); Christoph Renner, Zurich (CH)

(73) Assignees: UNIVERSITÄT ZÜRICH, Zurich (CH); UNIVERSITÄT BASEL, Basel (CH)

( * ) Notice: Subject to any disclaimer, the term of this patent is extended or adjusted under 35 U.S.C. 154(b) by 15 days.

(21) Appl. No.: 17/687,732

(22) Filed: Mar. 7, 2022

(65) Prior Publication Data

US 2022/0185865 A1    Jun. 16, 2022

Related U.S. Application Data

(62) Division of application No. 16/323,902, filed as application No. PCT/EP2017/070255 on Aug. 9, 2017, now Pat. No. 11,279,747.

(30) Foreign Application Priority Data

Aug. 10, 2016 (EP) ..................................... 16183626
Jan. 25, 2017 (EP) ..................................... 17153123

(51) Int. Cl.
| | | |
|---|---|---|
| A61K 48/00 | (2006.01) | |
| C07K 14/74 | (2006.01) | |
| A61K 39/395 | (2006.01) | |
| A61P 31/22 | (2006.01) | |
| A61P 31/18 | (2006.01) | |
| A61P 31/16 | (2006.01) | |
| A61P 35/00 | (2006.01) | |

(52) U.S. Cl.
CPC ...... *C07K 14/70539* (2013.01); *A61K 39/395* (2013.01); *A61K 48/00* (2013.01); *A61P 31/16* (2018.01); *A61P 31/18* (2018.01); *A61P 31/22* (2018.01); *A61P 35/00* (2018.01); *C07K 2319/00* (2013.01); *Y02A 50/30* (2018.01)

(58) Field of Classification Search
None
See application file for complete search history.

(56) References Cited

U.S. PATENT DOCUMENTS

| | | |
|---|---|---|
| 2006/0134744 A1 | 6/2006 | Hildebrand |
| 2011/0219464 A1 | 9/2011 | Domon |
| 2013/0078253 A1 | 3/2013 | Fang |
| 2013/0259876 A1 | 10/2013 | Murphy |
| 2015/0125456 A1 | 5/2015 | Kim |

FOREIGN PATENT DOCUMENTS

| | | |
|---|---|---|
| CN | 1849395 | 10/2006 |
| CN | 102227214 | 10/2011 |
| CN | 102958942 | 3/2013 |
| WO | 1999058557 | 11/1999 |
| WO | 2004029071 | 4/2004 |
| WO | 2015022669 | 2/2015 |
| WO | 2015153969 | 10/2015 |
| WO | 2016124661 | 8/2016 |

OTHER PUBLICATIONS

Zhong et al. Dimerization of Soluble HLA-G by IgG-Fc Fragment AugmentsILT2 Mediated Inhibition of T-Cell Alloresponse. Transplantation, 87(1): 8-15, Jan. 15, 2009.*
Favier et al. Tolerogenic Function of Dimeric Forms of HLA-G Recombinant Proteins: A Comparative Study In Vivo. PLoS ONE, 2011, 6(7): e21011.*
Cullen et al. A Divalent Major Histocompatibility Complex/IgG1 Fusion Protein Induces Antigen-Specific T Cell Activation in Vitro and in Vivo. Cellular Immunology 192, 54-62 (1999).*
Arosa et al: "Open conformers: the hidden face of MHC-I molecules", Trends in Immunology (2007), vol. 28, No. 3, pp. 115-123.
Stephens et al: "HIV-1 diversity versus HLA class I polymorphism", Trends in Immunology (2005), vol. 26, No. 1, pp. 41-47.
Smith et al: "Characterization of signaling function and expression of HLA class I molecules in medulloblastoma", Journal of Neuro-Oncology (2010), vol. 103, No. 2, pp. 197-206.
Zhao et al: "[beta]2-Microglobulin-free HLA-G activates natural killer cells by increasing cytotoxicity and proinflammatory cytokine production", Human Immunology (2013), vol. 74, No. 4, pp. 417-424.
Kao et al: "Evaluation of individual specificities of class I HLA on platelets by a newly developed monoclonal antibody", Human Immonulogy (1990), vol. 27, No. 4, pp. 285-297.
Maohua et al: "Dimerization of solubla HLA-G by IgG-Fc fragment augments ILT2-mediated inhibition of T-cell alloresponse", Transplantation (2009), vol. 87, No. 1, pp. 8-15.

(Continued)

*Primary Examiner* — Nianxiang Zou
(74) *Attorney, Agent, or Firm* — JMB Davis Ben-David

(57) ABSTRACT

The invention relates to MHC-Ia open conformers as immunomodulatory agents, particularly in the treatment or prevention of cancer. The open conformer comprises or consists of a first and a second monomer, and each monomer comprises a HLA-heavy chain from the MHC-Ia molecules. The open conformer further comprises a protein stabilizing polypeptide sequence and optionally an amino acid linker. Further aspects of the invention provide combination medicaments comprising the MHC-Ia open conformers and immune checkpoint inhibitors. Furthermore, the invention relates to the use of MHC-Ia open conformers as immunomodulators, particularly in diseases where the interaction to diverse immunoregulatory receptors such as KIR3DL1, KIR3DL2, KIR3DL3, LILRB1, LILRB2, and PTPRJ modulates an immune response, and in diseases were the negative modulation of Tregs is a therapeutic strategy, e.g. infectious diseases.

15 Claims, 37 Drawing Sheets

Specification includes a Sequence Listing.

(56) References Cited

OTHER PUBLICATIONS

MHC class I antigen, partial [*Homo sapiens*]; GenBank Accession No. AAL18239; 2001.
MHC class I antigen, partial [*Homo sapiens*]; GenBank Accession No. AAQ13833, 2004.
Beers and Berkow, The Merck Manual (1999), vol. 17, pp. 986-995.
Rao et al: "Anti-PD-1/PD-L1 therpy for infectious diseases: learning from the cancer paradigm", Internatrional journal of infectious Diseases (2017), vol. 56, pp. 221-228.
Pauken et al: "The PD-1 Pathway regulates Development and function of memory CD8+ T cells following respiratory viral infection", Cell Rep. (2020), Author Manuscript.
Ayodele et al: "Immuntherapy in soft-tissue sarcoma", Current Oncology (2020), (S1):17-23.
Levy F et al: "Co-Expression of the Human HLA-B27 Class I Antigen and the E3/19K Protein of Adenovirus-2 in Insect Cells Using a Baculovirus Vector", International Immunology, Oxford University Press, GB, vol. 2, No. 10, Jan. 1, 1990 (Jan. 1, 1990), pp. 995-1002, XP001106051, ISSN: 0953-8178.
Santos Susana G et al: "Induction of HLA-B27 heavy chain homodimer formation after activation in dendritic cells.", Arthritis Research & Therapy 2008, vol. 10, No. 4, 2008, p. R100, XP0216803, ISSN: 1478-6362.
R. Tarazona et al: "HLA-B2702 (77-83/83-77) Peptide Binds to Tubulin on Human NK Cells and Blocks Their Cytotoxic Capacity", The Journal of Immunology, vol. 165, No. 12, Dec. 15, 2000 (Dec. 15, 2000), pp. 6776-6782, XP055257084, US, ISSN: 0022-1767, 001: 10.4049/jimmunol.165.12.6776.
Guillermo Mazzolini et al: "Immunotherapy and immunoescape in colorectal cancer", World Journal of Gastroenterology, vol. 13, No. 44, Nov. 1, 2007 (Nov. 1, 2007), pp. 5822-5831, XP055257553, CN, ISSN: 1007-9327, 001 : 10.3748/wjg.v13.i44.5822.
Dolan et al. Cancer Control. 21(3): 231-237, Jul. 2014.
Yu et al. Targeted Delivery of an Antigenic Peptide to the Endoplasmic Reticulum: Application for Development of a Peptide Therapy for Ankylosing Spondylitis. PLOS ONE 8 (10): 1-14, published Oct. 14, 2013.
Ciprandi G et al: "Soluble HLA-G and HLA-A,-B,-C serum levels in patients with allergic rhinitis", Allergy (Oxford), vol. 63, No. 10, Oct. 2008 (Oct. 2008), pp. 1335-1338, XP002770154, ISSN: 0105-4538.
Luthra-Guptasarma M et al: "HLA-B27 lacking associated beta2-microglobulin rearranges to auto-display or cross-display residues 169-181: a novel molecular mechanism for spondyloarthropathies", FEBS Letters, Elsevier, Amsterdam, NL, vol. 575, No. 1-3, Sep. 24, 2004 (Sep. 24, 2004), pp. 1-8, XP004573846, ISSN: 0014-5793. DOI: 10.1016/J.FEBSLET.2004.08.037.
Rana Manish Kumar et al: "Multi-modal Binding of a 'Self' Peptide by HLA-B*27:04 and B*27:05 Allelic Variants, but not B*27:09 or B*27:06 Variants: Fresh Support for Some Theories Explaining Differential Disease Association", Protein Journal, Kluwer Academic/ Plenum Publishers, Dordrecht, NL, vol. 35, No. 5, Sep. 7, 2016 (Sep. 7, 2016), pp. 346-353, XP036088952, ISSN: 1572-3887, DOI: 10. 1007/S10930-016-9678-6.
Suzanne L. Topalian et al: "Immune Checkpoint Blockade: A Common Denominator Approach to Cancer Therapy". Cancer Cell. vol. 27, No. 4. Apr. 1, 2015 (Apr. 1, 2015), pp. 450-461, XP055372181. US, ISSN: 1535-6108, DOI: 10.1016/j.ccell.2015.03.001.
Marchesi et al. "HLA-dependent tumour development: a role for tumour associate macrophages?", Journal of Translational Medicine, 2013, vol. 11, No. 247, p. 1-15.
Zipeto et al. "HLA-C and HIV-1: friends or foes?", Retrovirology, 2012, vol. 9, No. 39, p. 1-9.
Baia et al., "Interaction of the LILRB1 inhibitory receptor with HLA class Ia dimers", Eur. J. Immunology, 2016, vol. 46, p. 1681-1690.
Goodridge et al. "HLA-F and MHC-I Open Conformers Cooperate in a MHC-I Antigen Cross-Presentation Pathway", The Journal of Immunology, 2013, 191: 1567-1577.
Cullen et al. "A Divalent Major Histocompatibility ComplexIlgG1 Fusion Protein Induces Antigen-Specific T Cell Activation in Vitro and in Vivo", Cellular Immunology 192, 54-62 (1999).

\* cited by examiner

A

B

A

B

SEQUENCE LISTING

<160> NUMBER OF SEQ ID NOS: 9

<210> SEQ ID NO 1
<211> LENGTH: 10
<212> TYPE: PRT
<213> ORGANISM: Artificial Sequence
<220> FEATURE:
<223> OTHER INFORMATION: amino acid linker

<400> SEQUENCE: 1

Gly Gly Gly Gly Ser Gly Gly Gly Gly Ser
1               5                   10

<210> SEQ ID NO 2
<211> LENGTH: 365
<212> TYPE: PRT

<213> ORGANISM: Homo sapiens

<400> SEQUENCE: 2

Met Ala Val Met Ala Pro Arg Thr Leu Val Leu Leu Leu Ser Gly Ala
1               5                   10                  15

Leu Ala Leu Thr Gln Thr Trp Ala Gly Ser His Ser Met Arg Tyr Phe
            20                  25                  30

Tyr Thr Ser Val Ser Arg Pro Gly Arg Gly Glu Pro Arg Phe Ile Ala
        35                  40                  45

Val Gly Tyr Val Asp Asp Thr Gln Phe Val Arg Phe Asp Ser Asp Ala
    50                  55                  60

Ala Ser Gln Arg Met Glu Pro Arg Ala Pro Trp Ile Glu Gln Glu Gly
65                  70                  75                  80

Pro Glu Tyr Trp Asp Arg Asn Thr Arg Asn Val Lys Ala His Ser Gln
                85                  90                  95

Thr Asp Arg Glu Ser Leu Arg Ile Ala Leu Arg Tyr Tyr Asn Gln Ser
            100                 105                 110

Glu Asp Gly Ser His Thr Ile Gln Arg Met Tyr Gly Cys Asp Val Gly
        115                 120                 125

Pro Asp Gly Arg Phe Leu Arg Gly Tyr Gln Asp Ala Tyr Asp Gly
    130                 135                 140

Lys Asp Tyr Ile Ala Leu Asn Glu Asp Leu Arg Ser Trp Thr Ala Ala
145                 150                 155                 160

Asp Met Ala Ala Gln Ile Thr Gln Arg Lys Trp Glu Thr Ala His Glu
                165                 170                 175

Ala Glu Gln Trp Arg Ala Tyr Leu Glu Gly Arg Cys Val Glu Trp Leu
            180                 185                 190

Arg Arg Tyr Leu Glu Asn Gly Lys Glu Thr Leu Gln Arg Thr Asp Ala
        195                 200                 205

Pro Lys Thr His Met Thr His His Ala Val Ser Asp His Glu Ala Thr
    210                 215                 220

Leu Arg Cys Trp Ala Leu Ser Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Gly Thr Phe Gln Lys Trp Ala Ser Val Val
            260                 265                 270

Val Pro Ser Gly Gln Glu Gln Arg Tyr Thr Cys His Val Gln His Glu
        275                 280                 285

Gly Leu Pro Lys Pro Leu Thr Leu Arg Trp Glu Pro Ser Ser Gln Pro
    290                 295                 300

Thr Ile Pro Ile Val Gly Ile Ile Ala Gly Leu Val Leu Phe Gly Ala
305                 310                 315                 320

Val Ile Ala Gly Ala Val Val Ala Ala Val Met Trp Arg Arg Lys Ser
                325                 330                 335

Ser Asp Arg Lys Gly Gly Ser Tyr Ser Gln Ala Ala Ser Ser Asp Ser
            340                 345                 350

Ala Gln Gly Ser Asp Met Ser Leu Thr Ala Cys Lys Val
        355                 360                 365

<210> SEQ ID NO 3
<211> LENGTH: 365
<212> TYPE: PRT
<213> ORGANISM: Homo sapiens

<400> SEQUENCE: 3

```
Met Ala Val Met Ala Pro Arg Thr Leu Leu Leu Leu Ser Gly Ala
1               5                   10                  15

Leu Ala Leu Thr Gln Thr Trp Ala Gly Ser His Ser Met Arg Tyr Phe
            20                  25                  30

Ser Thr Ser Val Ser Arg Pro Gly Ser Gly Glu Pro Arg Phe Ile Ala
        35                  40                  45

Val Gly Tyr Val Asp Asp Thr Gln Phe Val Arg Phe Asp Ser Asp Ala
    50                  55                  60

Ala Ser Gln Arg Met Glu Pro Arg Ala Pro Trp Ile Glu Gln Glu Arg
65                  70                  75                  80

Pro Glu Tyr Trp Asp Gln Glu Thr Arg Asn Val Lys Ala Gln Ser Gln
                85                  90                  95

Thr Asp Arg Val Asp Leu Gly Thr Leu Arg Gly Tyr Tyr Asn Gln Ser
            100                 105                 110

Glu Ala Gly Ser His Thr Ile Gln Ile Met Tyr Gly Cys Asp Val Gly
        115                 120                 125

Ser Asp Gly Arg Phe Leu Arg Gly Tyr Glu Gln His Ala Tyr Asp Gly
130                 135                 140

Lys Asp Tyr Ile Ala Leu Asn Glu Asp Leu Arg Ser Trp Thr Ala Ala
145                 150                 155                 160

Asp Met Ala Ala Gln Ile Thr Gln Arg Lys Trp Glu Ala Ala Arg Trp
                165                 170                 175

Ala Glu Gln Leu Arg Ala Tyr Leu Glu Gly Thr Cys Val Glu Trp Leu
            180                 185                 190

Arg Arg Tyr Leu Glu Asn Gly Lys Glu Thr Leu Gln Arg Thr Asp Pro
        195                 200                 205

Pro Lys Thr His Met Thr His His Pro Ile Ser Asp His Glu Ala Thr
210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Gly Thr Phe Gln Lys Trp Ala Ala Val Val
            260                 265                 270

Val Pro Ser Gly Glu Glu Gln Arg Tyr Thr Cys His Val Gln His Glu
        275                 280                 285

Gly Leu Pro Lys Pro Leu Thr Leu Arg Trp Glu Leu Ser Ser Gln Pro
290                 295                 300

Thr Ile Pro Ile Val Gly Ile Ile Ala Gly Leu Val Leu Leu Gly Ala
305                 310                 315                 320

Val Ile Thr Gly Ala Val Val Ala Ala Val Met Trp Arg Arg Lys Ser
                325                 330                 335

Ser Asp Arg Lys Gly Gly Ser Tyr Thr Gln Ala Ala Ser Ser Asp Ser
            340                 345                 350

Ala Gln Gly Ser Asp Val Ser Leu Thr Ala Cys Lys Val
        355                 360                 365
```

<210> SEQ ID NO 4
<211> LENGTH: 362
<212> TYPE: PRT
<213> ORGANISM: Homo sapiens

<400> SEQUENCE: 4

```
Met Arg Val Thr Ala Pro Arg Thr Leu Leu Leu Leu Trp Gly Ala
1               5                   10                  15

Val Ala Leu Thr Glu Thr Trp Ala Gly Ser His Ser Met Arg Tyr Phe
            20                  25                  30

His Thr Ser Val Ser Arg Pro Gly Arg Gly Glu Pro Arg Phe Ile Thr
            35                  40                  45

Val Gly Tyr Val Asp Asp Thr Leu Phe Val Arg Phe Asp Ser Asp Ala
50                  55                  60

Ala Ser Pro Arg Glu Glu Pro Arg Ala Pro Trp Ile Glu Gln Glu Gly
65                  70                  75                  80

Pro Glu Tyr Trp Asp Arg Glu Thr Gln Ile Cys Lys Ala Lys Ala Gln
                85                  90                  95

Thr Asp Arg Glu Asp Leu Arg Thr Leu Leu Arg Tyr Tyr Asn Gln Ser
                100                 105                 110

Glu Ala Gly Ser His Thr Leu Gln Asn Met Tyr Gly Cys Asp Val Gly
                115                 120                 125

Pro Asp Gly Arg Leu Leu Arg Gly Tyr His Gln Asp Ala Tyr Asp Gly
130                 135                 140

Lys Asp Tyr Ile Ala Leu Asn Glu Asp Leu Ser Ser Trp Thr Ala Ala
145                 150                 155                 160

Asp Thr Ala Ala Gln Ile Thr Gln Arg Lys Trp Glu Ala Ala Arg Val
                165                 170                 175

Ala Glu Gln Leu Arg Ala Tyr Leu Glu Gly Glu Cys Val Glu Trp Leu
                180                 185                 190

Arg Arg Tyr Leu Glu Asn Gly Lys Glu Thr Leu Gln Arg Ala Asp Pro
                195                 200                 205

Pro Lys Thr His Val Thr His His Pro Ile Ser Asp His Glu Ala Thr
210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Arg Thr Phe Gln Lys Trp Ala Ala Val Val
                260                 265                 270

Val Pro Ser Gly Glu Glu Gln Arg Tyr Thr Cys His Val Gln His Glu
                275                 280                 285

Gly Leu Pro Lys Pro Leu Thr Leu Arg Trp Glu Pro Ser Ser Gln Ser
290                 295                 300

Thr Val Pro Ile Val Gly Ile Val Ala Gly Leu Ala Val Leu Ala Val
305                 310                 315                 320

Val Val Ile Gly Ala Val Val Ala Ala Val Met Cys Arg Arg Lys Ser
                325                 330                 335

Ser Gly Gly Lys Gly Gly Ser Tyr Ser Gln Ala Ala Cys Ser Asp Ser
                340                 345                 350

Ala Gln Gly Ser Asp Val Ser Leu Thr Ala
                355                 360

<210> SEQ ID NO 5
<211> LENGTH: 362
<212> TYPE: PRT
<213> ORGANISM: Homo sapiens

<400> SEQUENCE: 5

Met Arg Val Thr Ala Pro Arg Thr Val Leu Leu Leu Trp Gly Ala
1               5                   10                  15
```

Val Ala Leu Thr Glu Thr Trp Ala Gly Ser His Ser Met Arg Tyr Phe
        20                  25                  30

Tyr Thr Ala Met Ser Arg Pro Gly Arg Gly Glu Pro Arg Phe Ile Ala
        35                  40                  45

Val Gly Tyr Val Asp Asp Thr Gln Phe Val Arg Phe Asp Ser Asp Ala
 50                  55                  60

Ala Ser Pro Arg Thr Glu Pro Arg Ala Pro Trp Ile Glu Gln Glu Gly
65                  70                  75                  80

Pro Glu Tyr Trp Asp Arg Asn Thr Gln Ile Phe Lys Thr Asn Thr Gln
                85                  90                  95

Thr Tyr Arg Glu Asn Leu Arg Ile Ala Leu Arg Tyr Tyr Asn Gln Ser
            100                 105                 110

Glu Ala Gly Ser His Ile Ile Gln Arg Met Tyr Gly Cys Asp Leu Gly
        115                 120                 125

Pro Asp Gly Arg Leu Leu Arg Gly His Asp Gln Ser Ala Tyr Asp Gly
    130                 135                 140

Lys Asp Tyr Ile Ala Leu Asn Glu Asp Leu Ser Ser Trp Thr Ala Ala
145                 150                 155                 160

Asp Thr Ala Ala Gln Ile Thr Gln Arg Lys Trp Glu Ala Ala Arg Val
                165                 170                 175

Ala Glu Gln Leu Arg Ala Tyr Leu Glu Gly Leu Cys Val Glu Trp Leu
            180                 185                 190

Arg Arg Tyr Leu Glu Asn Gly Lys Glu Thr Leu Gln Arg Ala Asp Pro
        195                 200                 205

Pro Lys Thr His Val Thr His His Pro Val Ser Asp His Glu Ala Thr
    210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Arg Thr Phe Gln Lys Trp Ala Ala Val Val
            260                 265                 270

Val Pro Ser Gly Glu Glu Gln Arg Tyr Thr Cys His Val Gln His Glu
        275                 280                 285

Gly Leu Pro Lys Pro Leu Thr Leu Arg Trp Glu Pro Ser Ser Gln Ser
    290                 295                 300

Thr Ile Pro Ile Val Gly Ile Val Ala Gly Leu Ala Val Leu Ala Val
305                 310                 315                 320

Val Val Ile Gly Ala Val Val Ala Thr Val Met Cys Arg Arg Lys Ser
                325                 330                 335

Ser Gly Gly Lys Gly Gly Ser Tyr Ser Gln Ala Ala Ser Ser Asp Ser
            340                 345                 350

Ala Gln Gly Ser Asp Val Ser Leu Thr Ala
        355                 360

<210> SEQ ID NO 6
<211> LENGTH: 362
<212> TYPE: PRT
<213> ORGANISM: Homo sapiens

<400> SEQUENCE: 6

Met Arg Val Thr Ala Pro Arg Thr Val Leu Leu Leu Trp Gly Ala
1               5                   10                  15

Val Ala Leu Thr Glu Thr Trp Ala Gly Ser His Ser Met Arg Tyr Phe

```
            20                  25                  30
Tyr Thr Ala Met Ser Arg Pro Gly Arg Gly Glu Pro Arg Phe Ile Ala
            35                  40                  45
Val Gly Tyr Val Asp Asp Thr Gln Phe Val Arg Phe Asp Ser Asp Ala
    50                  55                  60
Ala Ser Pro Arg Met Ala Pro Arg Ala Pro Trp Ile Glu Gln Glu Gly
65                  70                  75                  80
Pro Glu Tyr Trp Asp Gly Glu Thr Arg Asn Met Lys Ala Ser Ala Gln
                85                  90                  95
Thr Tyr Arg Glu Asn Leu Arg Ile Ala Leu Arg Tyr Tyr Asn Gln Ser
            100                 105                 110
Glu Ala Gly Ser His Ile Ile Gln Val Met Tyr Gly Cys Asp Val Gly
        115                 120                 125
Pro Asp Gly Arg Leu Leu Arg Gly His Asp Gln Ser Ala Tyr Asp Gly
    130                 135                 140
Lys Asp Tyr Ile Ala Leu Asn Glu Asp Leu Ser Ser Trp Thr Ala Ala
145                 150                 155                 160
Asp Thr Ala Ala Gln Ile Thr Gln Arg Lys Trp Glu Ala Ala Arg Val
                165                 170                 175
Ala Glu Gln Leu Arg Ala Tyr Leu Glu Gly Leu Cys Val Glu Trp Leu
            180                 185                 190
Arg Arg Tyr Leu Glu Asn Gly Lys Glu Thr Leu Gln Arg Ala Asp Pro
        195                 200                 205
Pro Lys Thr His Val Thr His His Pro Ile Ser Asp His Glu Ala Thr
    210                 215                 220
Leu Arg Cys Trp Ala Leu Gly Phe Tyr Pro Ala Glu Ile Thr Leu Thr
225                 230                 235                 240
Trp Gln Arg Asp Gly Glu Asp Gln Thr Gln Asp Thr Glu Leu Val Glu
                245                 250                 255
Thr Arg Pro Ala Gly Asp Arg Thr Phe Gln Lys Trp Ala Ala Val Val
            260                 265                 270
Val Pro Ser Gly Glu Glu Gln Arg Tyr Thr Cys His Val Gln His Glu
        275                 280                 285
Gly Leu Pro Lys Pro Leu Thr Leu Arg Trp Glu Pro Ser Ser Gln Ser
    290                 295                 300
Thr Val Pro Ile Val Gly Ile Val Ala Gly Leu Ala Val Leu Ala Val
305                 310                 315                 320
Val Val Ile Gly Ala Val Val Ala Ala Val Met Cys Arg Arg Lys Ser
                325                 330                 335
Ser Gly Gly Lys Gly Gly Ser Tyr Ser Gln Ala Ala Cys Ser Asp Ser
            340                 345                 350
Ala Gln Gly Ser Asp Val Ser Leu Thr Ala
        355                 360

<210> SEQ ID NO 7
<211> LENGTH: 362
<212> TYPE: PRT
<213> ORGANISM: Homo sapiens

<400> SEQUENCE: 7

Met Arg Val Thr Ala Pro Arg Thr Val Leu Leu Leu Leu Trp Gly Ala
1               5                   10                  15
Val Ala Leu Thr Glu Thr Trp Ala Gly Ser His Ser Met Arg Tyr Phe
            20                  25                  30
```

Tyr Thr Ala Met Ser Arg Pro Gly Arg Gly Glu Pro Arg Phe Ile Ala
                35                  40                  45

Val Gly Tyr Val Asp Asp Thr Gln Phe Val Arg Phe Asp Ser Asp Ala
 50                  55                  60

Ala Ser Pro Arg Thr Glu Pro Arg Ala Pro Trp Ile Glu Gln Glu Gly
 65                  70                  75                  80

Pro Glu Tyr Trp Asp Gly Glu Thr Arg Asn Met Lys Ala Ser Ala Gln
                 85                  90                  95

Thr Tyr Arg Glu Asn Leu Arg Ile Ala Leu Arg Tyr Tyr Asn Gln Ser
                100                 105                 110

Glu Ala Gly Ser His Ile Ile Gln Arg Met Tyr Gly Cys Asp Leu Gly
                115                 120                 125

Pro Asp Gly Arg Leu Leu Arg Gly His Asp Gln Ser Ala Tyr Asp Gly
130                 135                 140

Lys Asp Tyr Ile Ala Leu Asn Glu Asp Leu Ser Ser Trp Thr Ala Ala
145                 150                 155                 160

Asp Thr Ala Ala Gln Ile Thr Gln Arg Lys Trp Glu Ala Ala Arg Val
                165                 170                 175

Ala Glu Gln Leu Arg Ala Tyr Leu Glu Gly Leu Cys Val Glu Trp Leu
                180                 185                 190

Arg Arg Tyr Leu Glu Asn Gly Lys Glu Thr Leu Gln Arg Ala Asp Pro
                195                 200                 205

Pro Lys Thr His Val Thr His His Pro Val Ser Asp His Glu Ala Thr
                210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Arg Thr Phe Gln Lys Trp Ala Ala Val Val
                260                 265                 270

Val Pro Ser Gly Glu Glu Gln Arg Tyr Thr Cys His Val Gln His Glu
                275                 280                 285

Gly Leu Pro Lys Pro Leu Thr Leu Arg Trp Glu Pro Ser Ser Gln Ser
290                 295                 300

Thr Ile Pro Ile Val Gly Ile Val Ala Gly Leu Ala Val Leu Ala Val
305                 310                 315                 320

Val Val Ile Gly Ala Val Val Ala Thr Val Met Cys Arg Arg Lys Ser
                325                 330                 335

Ser Gly Gly Lys Gly Gly Ser Tyr Ser Gln Ala Ala Ser Ser Asp Ser
                340                 345                 350

Ala Gln Gly Ser Asp Val Ser Leu Thr Ala
                355                 360

<210> SEQ ID NO 8
<211> LENGTH: 366
<212> TYPE: PRT
<213> ORGANISM: Homo sapiens

<400> SEQUENCE: 8

Met Arg Val Met Ala Pro Arg Thr Leu Ile Leu Leu Leu Ser Gly Ala
 1               5                  10                  15

Leu Ala Leu Thr Glu Thr Trp Ala Cys Ser His Ser Met Arg Tyr Phe
                20                  25                  30

Tyr Thr Ala Val Ser Arg Pro Gly Arg Gly Glu Pro Arg Phe Ile Ala
                35                  40                  45

Val Gly Tyr Val Asp Asp Thr Gln Phe Val Gln Phe Asp Ser Asp Ala
 50                  55                  60

Ala Ser Pro Arg Gly Glu Pro Arg Ala Pro Trp Val Glu Gln Glu Gly
 65                  70                  75                  80

Pro Glu Tyr Trp Asp Arg Glu Thr Gln Lys Tyr Lys Arg Gln Ala Gln
                 85                  90                  95

Thr Asp Arg Val Ser Leu Arg Asn Leu Arg Gly Tyr Tyr Asn Gln Ser
                100                 105                 110

Glu Ala Gly Ser His Thr Leu Gln Arg Met Tyr Gly Cys Asp Leu Gly
                115                 120                 125

Pro Asp Gly Arg Leu Leu Arg Gly Tyr Asn Gln Phe Ala Tyr Asp Gly
        130                 135                 140

Lys Asp Tyr Ile Ala Leu Asn Glu Asp Leu Arg Ser Trp Thr Ala Ala
145                 150                 155                 160

Asp Thr Ala Ala Gln Ile Thr Gln Arg Lys Trp Glu Ala Ala Arg Thr
                165                 170                 175

Ala Glu Gln Leu Arg Ala Tyr Leu Glu Gly Thr Cys Val Glu Trp Leu
                180                 185                 190

Arg Arg Tyr Leu Glu Asn Gly Lys Lys Thr Leu Gln Arg Ala Glu His
                195                 200                 205

Pro Lys Thr His Val Thr His His Pro Val Ser Asp His Glu Ala Thr
        210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Gly Thr Phe Gln Lys Trp Ala Ala Val Val
                260                 265                 270

Val Pro Ser Gly Glu Glu Gln Arg Tyr Thr Cys His Val Gln His Glu
        275                 280                 285

Gly Leu Pro Glu Pro Leu Thr Leu Arg Trp Gly Pro Ser Ser Gln Pro
        290                 295                 300

Thr Ile Pro Ile Val Gly Ile Ala Gly Leu Ala Val Leu Ala Val
305                 310                 315                 320

Leu Ala Val Leu Gly Ala Val Met Ala Val Met Cys Arg Arg Lys
                325                 330                 335

Ser Ser Gly Gly Lys Gly Gly Ser Cys Ser Gln Ala Ala Ser Ser Asn
                340                 345                 350

Ser Ala Gln Gly Ser Asp Glu Ser Leu Ile Ala Cys Lys Ala
        355                 360                 365

<210> SEQ ID NO 9
<211> LENGTH: 366
<212> TYPE: PRT
<213> ORGANISM: Homo sapiens

<400> SEQUENCE: 9

Met Arg Val Met Ala Pro Arg Thr Leu Ile Leu Leu Leu Ser Gly Ala
 1               5                  10                  15

Leu Ala Leu Thr Glu Thr Trp Ala Cys Ser His Ser Met Arg Tyr Phe
                20                  25                  30

Tyr Thr Ala Val Ser Arg Pro Gly Arg Gly Glu Pro Arg Phe Ile Ala
                35                  40                  45

Val Gly Tyr Val Asp Asp Thr Gln Phe Val Arg Phe Asp Ser Asp Ala

-continued

```
                50                  55                  60
Ala Ser Pro Arg Gly Glu Pro Arg Ala Pro Trp Val Gln Glu Gly
65                  70                  75                  80

Pro Glu Tyr Trp Asp Arg Glu Thr Gln Lys Tyr Lys Arg Gln Ala Gln
                85                  90                  95

Ala Asp Arg Val Ser Leu Arg Asn Leu Arg Gly Tyr Tyr Asn Gln Ser
                100                 105                 110

Glu Ala Gly Ser His Thr Leu Gln Arg Met Tyr Gly Cys Asp Leu Gly
                115                 120                 125

Pro Asp Gly Arg Leu Leu Arg Gly Tyr Asp Gln Ser Ala Tyr Asp Gly
                130                 135                 140

Lys Asp Tyr Ile Ala Leu Asn Glu Asp Leu Arg Ser Trp Thr Ala Ala
145                 150                 155                 160

Asp Thr Ala Ala Gln Ile Thr Gln Arg Lys Trp Glu Ala Ala Arg Glu
                165                 170                 175

Ala Glu Gln Trp Arg Ala Tyr Leu Glu Gly Thr Cys Val Glu Trp Leu
                180                 185                 190

Arg Arg Tyr Leu Glu Asn Gly Lys Glu Thr Leu Gln Arg Ala Glu His
                195                 200                 205

Pro Lys Thr His Val Thr His His Pro Val Ser Asp His Glu Ala Thr
                210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Gly Thr Phe Gln Lys Trp Ala Ala Val Val
                260                 265                 270

Val Pro Ser Gly Glu Glu Gln Arg Tyr Thr Cys His Val Gln His Glu
                275                 280                 285

Gly Leu Pro Glu Pro Leu Thr Leu Arg Trp Glu Pro Ser Ser Gln Pro
                290                 295                 300

Thr Ile Pro Ile Val Gly Ile Val Ala Gly Leu Ala Val Leu Ala Val
305                 310                 315                 320

Leu Ala Val Leu Gly Ala Val Met Ala Val Val Met Cys Arg Arg Lys
                325                 330                 335

Ser Ser Gly Gly Lys Gly Gly Ser Cys Ser Gln Ala Ala Ser Ser Asn
                340                 345                 350

Ser Ala Gln Gly Ser Asp Glu Ser Leu Ile Ala Cys Lys Ala
                355                 360                 365
```

MHC CLASS IA OPEN CONFORMERS

CROSS-REFERENCE TO RELATED APPLICATIONS

This is a division of U.S. patent application Ser. No. 16/323,902, filed on Feb. 7, 2019, which is the US National Stage of International Patent Application No. PCT/EP2017/070255, filed on Aug. 9, 2017, which in turn claimed priority to European Patent Application No. 17153123.9, filed on Jan. 25, 2017, and European Patent Application No. 16183626.7, filed on Aug. 10, 2016. The contents of the foregoing patent applications are hereby incorporated by reference in their entirety.

FIELD

The present invention relates to the use of classical MHC class Ia (MHC-Ia) open conformers, particularly for use in the prophylaxis or treatment of cancer, and for use as immunomodulators.

BACKGROUND

Human leukocyte antigens (HLA) belong to the classical major histocompatibility complex (MHC) protein family. The HLA complex helps the immune system distinguish the body's own proteins from proteins made by foreign invaders such as viruses and bacteria. Humans have MHC class I molecules comprising the classical (MHC-Ia) HLA-A, HLA-B, and HLA-C, and the non-classical (MHC-Ib) HLA-E, HLA-F, HLA-G and HLA-H molecules. Both categories are similar in their mechanisms of peptide binding, presentation and induced T-cell responses. The most remarkable feature of the classical MHC-Ia is their high polymorphism, while the non-classical MHC-Ib are usually non-polymorphic and tend to show a more restricted pattern of expression than their MHC-Ia counterparts.

The HLA nomenclature is given by the particular name of gene locus (e.g. HLA-A) followed by the allele family serological antigen (e.g. HLA-A*02), and allele subtypes assigned in numbers and in the order in which DNA sequences have been determined (e.g. HLA-A*02:01). Alleles that differ only by synonymous nucleotide substitutions (also called silent or non-coding substitutions) within the coding sequence are distinguished by the use of the third set of digits (e.g. HLA-A*02:01:01). Alleles that only differ by sequence polymorphisms in the introns, or in the 5' or 3' untranslated regions that flank the exons and introns, are distinguished by the use of the fourth set of digits (e.g. HLA-A*02:01:01:02 L) (FIG. 1).

A list of MHC-Ia alleles is provided in Table 1. For a complete list of allele subtypes visit the link: http://hla.alleles.org/alleles/class1.html.

Classical MHC-Ia molecules' principle function is to present peptides as part of the adaptive immune response. MHC-Ia molecules are trimeric structures comprising a membrane-bound heavy chain with three extracellular domains (α1, α2 and α3) that associates non-covalently with β2-microglobulin (β2m) and a small peptide which is derived from self-proteins, viruses or bacteria. The α1 and α2 domains are highly polymorphic and form a platform that gives rise to the peptide-binding groove. Juxtaposed to the conserved α3 domain is a transmembrane domain followed by an intracellular cytoplasmic tail.

To initiate an immune response classical MHC-Ia molecules present specific peptides to be recognized by TCR (T cell receptor) present on $CD8^+$ cytotoxic T lymphocytes (CTLs), while NK cell receptors present in natural killer cells (NK) recognize peptide motifs, rather than individual peptides. Under normal physiological conditions, MHC-Ia molecules exist as heterotrimeric complexes in charge of presenting peptides to CD8+ T cells and NK cells, however, MHC-Ia molecules may also be present in cells as free-heavy chains lacking β2-microglobulin and peptide, and are referred to as HLA-open conformers (Arosa et al., Trends in Immunology 2007 March; 28(3):115-23) (FIG. 2). The interaction of HLA-open conformers with T cell receptors and NK cell receptors is independent of the peptide and its function is unknown.

Open conformers can be expressed at the cell surface of cells and can be detected with antibodies recognizing linear epitopes of HLA molecules without β2m and peptide (e.g. LA45, L31, HCA2 and HC-10). These antibodies have been used to detect the presence of open conformers in diverse autoimmune patients and healthy individuals (Raine et al., Rheumatology 2006; 45:1338-1344). Despite their presence in patients and cell lines little is know of their mode of action. Open conformers have been mostly assessed in Ankylosing spondylitis (AS) +HLA-B27 patients, where HLA-B27 open conformers have been hypothesized to induce autoimmunity, their function in other autoimmune patients has not been yet addressed.

Here the inventors disclose for the first time that the classical MHC-Ia (HLA-A, HLA-B and HLA-C) family of molecules when present as open conformers (heavy chains without β2m) are useful therapeutics for their immunomodulatory properties and use in the treatment of cancer.

Cancer is a group of diseases characterized by abnormal cells of the body undergoing uncontrolled and destructive growth. Cancer cells can spread around the body and metastasize to form tumors; this growth pattern is called malignant. Cancer can be treated by surgery, chemotherapy, radiation therapy, hormonal therapy, targeted therapy and immunotherapy. The choice of therapy depends on the type of cancer, the stage of the cancer (how much it has spread), age, health status, and additional personal characteristics.

There is no single treatment for cancer, and patients often receive a combination of therapies and palliative care.

Cancer immunotherapy refers to a diverse set of therapeutic strategies designed to induce the patient's own immune system to fight the tumor, and is based on the insight that the progression of cancer, which involves the accumulation of diverse mutations, is monitored by the immune system. Immunotherapies either stimulate the activities of specific cell components of the immune system or counteract signals produced by cancer cells that suppress immune responses (Mahoney et al., Nat Rev Drug Discov. 2015 August; 14(8):561-84).

Different type of immune cells are involved in the immune response against cancer. Within this pool of white blood cells (immune contexture), the most notorious cells are: T-cells (cytotoxic CD8+ T-cells, T helper CD4+ cells—Th1, Th2, and Th17 phenotype), regulatory T cells (Tregs), macrophages (M1 type-pro-inflammatory and M2 type-pro-tumoral), myeloid derived suppressor cells (MDSCs), natural killer cells (NK cells), and dendritic cells (DCs). These immune cells can be located in the center of the tumor, in the invasive margin or in the adjacent tertiary lymphoid structures (Fridman et al., Nat. Rev. Cancer. 2012, April: 12, 298-306).

The density and composition of the immune microenvironment is heterogeneous among patients and tumors. It is now well established that in general the tumor infiltration with M2-phenotype macrophages and myeloid derived suppressor cells (MDSCs) promotes tumor progression, whereas infiltration of cytotoxic CD8+ T-cells, Th1 phenotype cells and M1 type macrophages are often associated with good clinical outcome, and good response to immunotherapy. The clinical impact of other lymphoid and myeloid cell populations is less consistent and seems dependent on the tumor type and stage. The presence of Th17, and NK cells, and the absence/reduction of Treg cells in tumor infiltrates is correlated with good outcome in some cancer indications (Giraldo et al., Current Opinion in Immunology 2014, 27:8-15). A general overview of the balance between leukocyte infiltrates and clinical outcome is reviewed in (Becht et al. Current Opinion in Immunology. 2016, 39:17-13).

Overall, modulating the immune contexture of tumors favoring the infiltration of M1 type macrophages, cytotoxic CD8 T-cells, and Th1 cells, and/or reducing the infiltration of MDSCs and M2 type macrophages is an promising therapeutic avenue to treat cancer that is explored here with the use of HLA open conformers proteins in diverse cancer indications.

% Δtumor inhibition of treated mice groups compared to control. The experimental design of injection time points of substances was as follow: isotype (5 mg/Kg) biwk×2; A25$_2$-Fc (5 mg/Kg) biwk×2; 4-1 BB antibody (1 mg/Kg) biwk×2 injections; A25$_2$-Fc+4-1 BB (5 mg/Kg and 1 mg/Kg, respectively) biwk×2; PD-1 antibody (5 mg/Kg) biwk×2; and A25$_2$-Fc+PD-1 (5 mg/Kg each) biwk×2. Tumor volumes are expressed as mean±SEM and analysed by two-way ANOVA followed by Bonferroni post-hoc analysis *p<0.05. Δtumor inhibition is calculated from the ΔT/ΔC tumor growth ratio, which represents the growth of the tumor in % from the beginning of the treatment (e.g. 300 mm$^3$), to the end volume of the treatment (e.g. 1000 mm$^3$) compared to isotype. biwk=twice a week.

Figure 10:
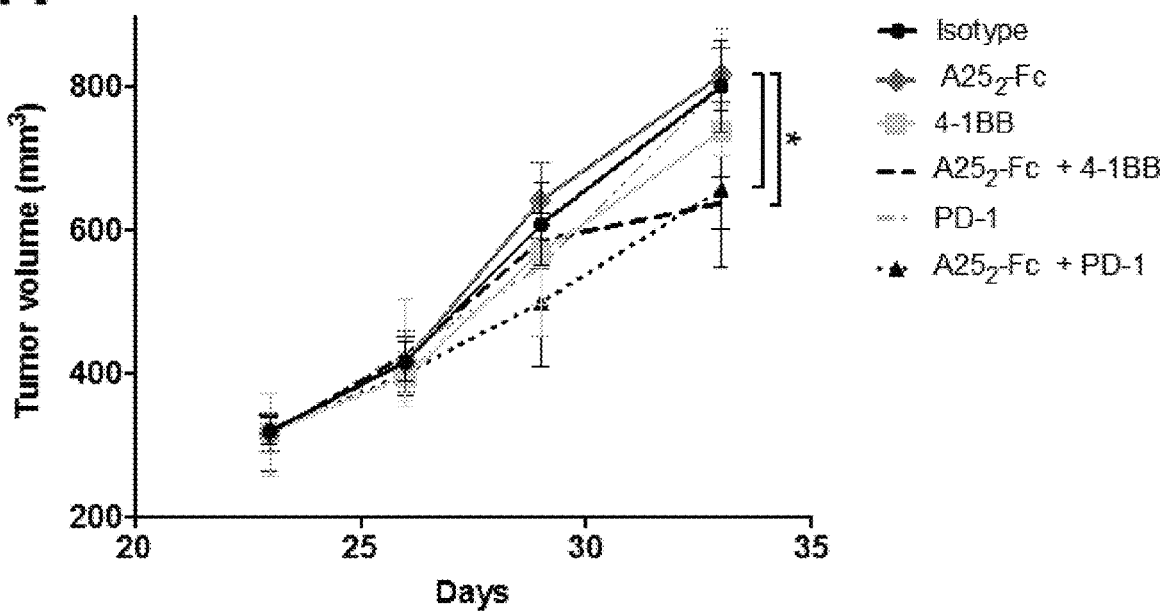
FIG. 10 shows the in vivo study of $A25_2$-Fc in combination with PD-1 and 4-1 BB antibodies in large tumors of the pancreatic Pan02 syngeneic mouse model. A) Mean average tumor volume in $mm^3$ of $A25_2$-Fc treated animals (n=6). B)
Figure 10:
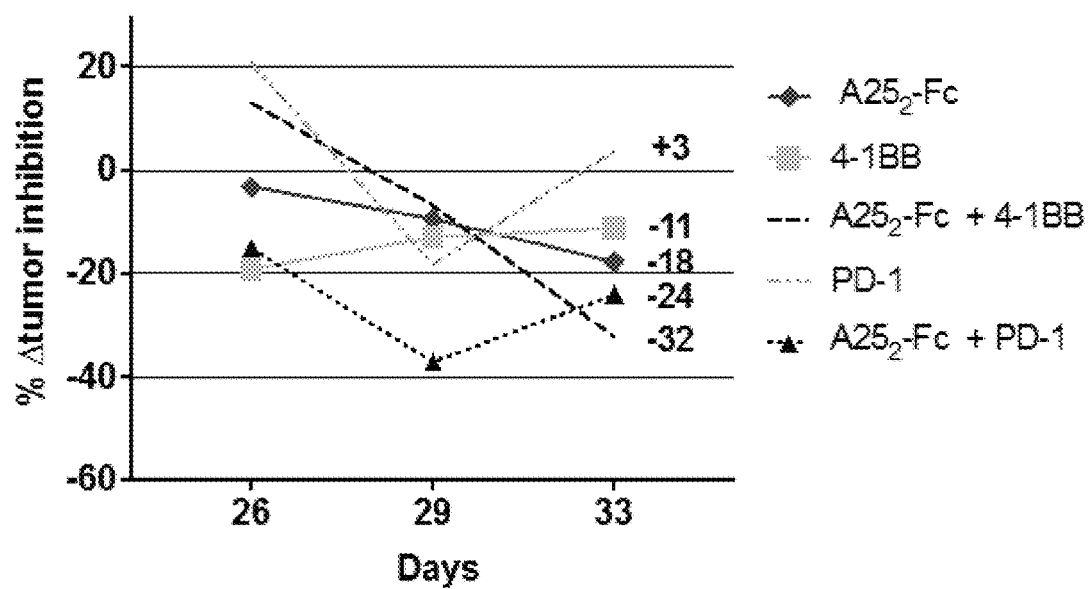
Figure 11:
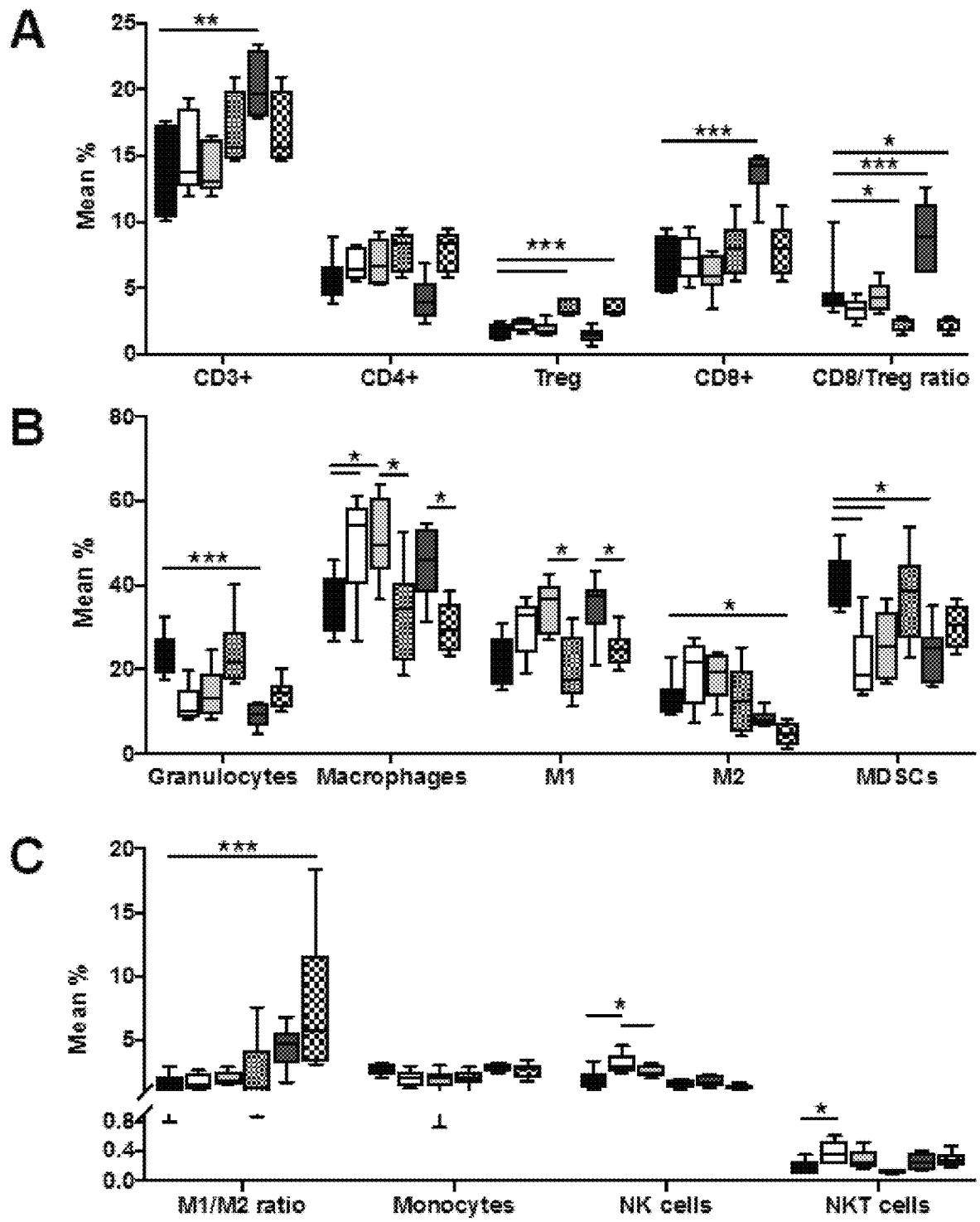

FIG. 11 shows the immune contexture of Tumor Infiltrating Lymphocytes (TILs) analysis from Pan02 pancreatic cancer mice with large tumors treated with A25$_2$-Fc, 4-1 BB and PD-1 by flow cytometry (continuation of experiment in FIG. 10). Relevant leukocytes analysed infiltrating the tumor: A) CD3+ T cells, CD4+ T cells, Regulatory T cells (Treg), CD8+ T cells, and the CD8+/Treg ratio. B) Granulocytes, Macrophages, Macrophage M1-type, Macrophage M2-type, and Myeloid Derived Suppressor Cells (MDSCs). C) M1/M2 macrophage ratio, Monocytes, Natural killer cells (NK), and Natural Killer T cells (NKT). Leukocytes % are expressed as box plots showing sample maxima and minima, and each group analysed by one-way ANOVA followed by Dunnet post-hoc analysis *p<0.05; p<0.01; *p<0.001.

Figure 12:
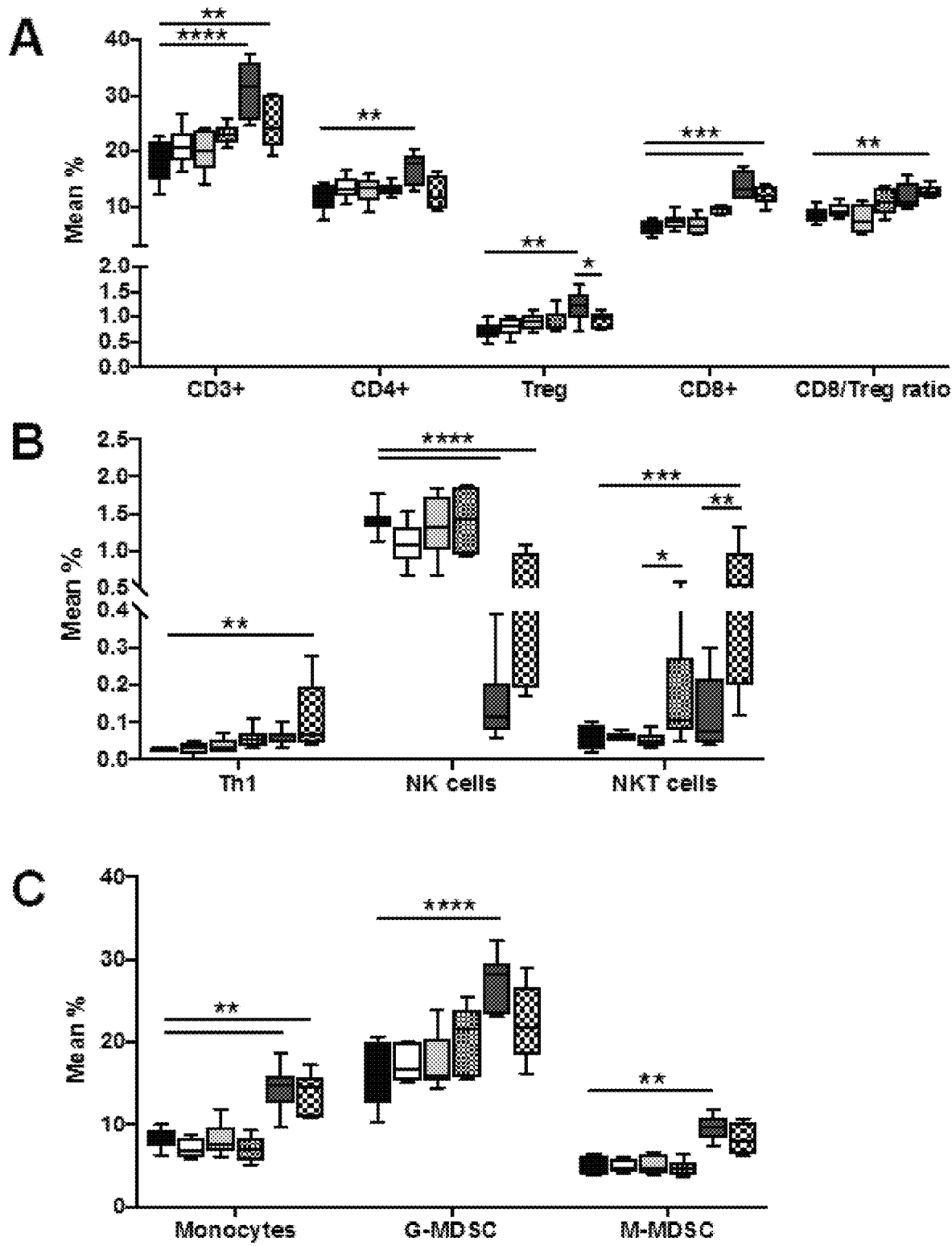

FIG. 12 shows the immune contexture of blood leukocyte analysis from Pan02 pancreatic cancer mice with large tumors treated with A25$_2$-Fc, 4-1 BB and PD-1 by flow cytometry (continuation of experiment in FIG. 10). Relevant leukocytes analysed present in the blood: A) CD3+ T cells, CD4+ T cells, Regulatory T cells (Treg), CD8+ T cells, and CD8+/Treg ratio. B) Th1 cells (CD4+ T cells IFNγ+), Natural Killer cells (NK), and Natural Killer T cells (NKT). C) Monocytes, Granulocyte-Myeloid Derived suppressor cells (G-MDSCs), and Monocytic-Myeloid Derived Suppressor cells (M-MDSCs). Leukocytes % are expressed as box plots showing sample maxima and minima, and each group analysed by one-way ANOVA followed by Dunnet post-hoc analysis *p<0.05; p<0.01; *p<0.001.

Figure 13:
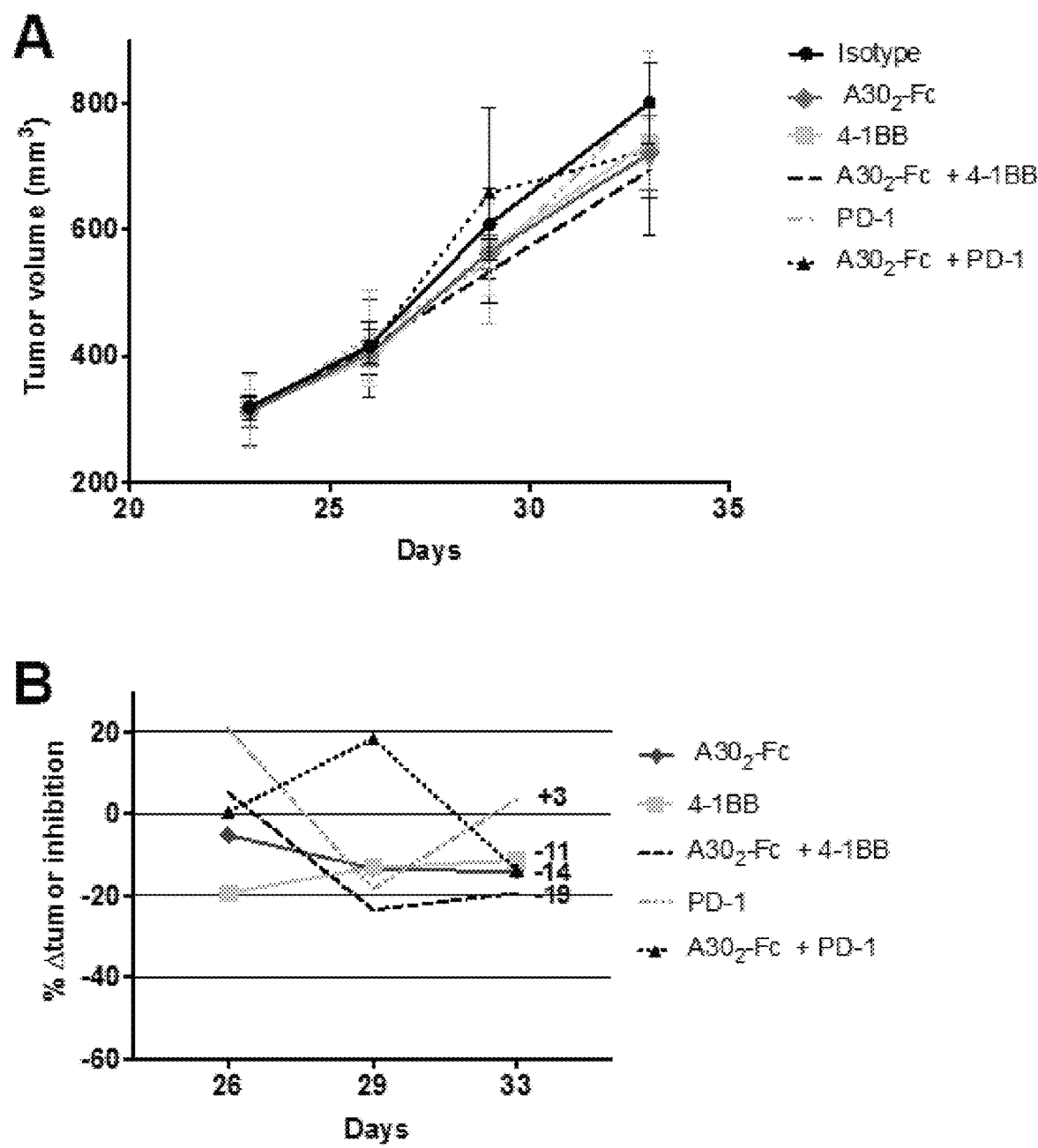

FIG. 13 shows the in vivo study of A30$_2$-Fc in combination with PD-1 and 4-1 BB antibodies in large tumors of the pancreatic Pan02 syngeneic mouse model. A) Mean average tumor volume in mm$^3$ of A30$_2$-Fc treated animals (n=6). B) % Δtumor inhibition of treated mice groups compared to control. The experimental design of injection time points of substances was as follow: isotype (5 mg/Kg) biwk×2; A30$_2$-Fc (5 mg/Kg) biwk×2; 4-1 BB antibody (1 mg/Kg) biwk×2 injections; A30$_2$-Fc+4-1 BB (5 mg/Kg and 1 mg/Kg, respectively) biwk×2; PD-1 antibody (5 mg/Kg) biwk×2; and A30$_2$-Fc+PD-1 (5 mg/Kg each) biwk×2. Tumor volumes are expressed as mean±SEM and analysed by two-way ANOVA followed by Bonferroni post-hoc analysis. Δtumor inhibition is calculated from the ΔT/ΔC tumor growth ratio, which represents the growth of the tumor in % from the beginning of the treatment (e.g. 300 mm$^3$), to the end volume of the treatment (e.g. 1000 mm$^3$) compared to isotype. biwk=twice a week.

Figure 14:
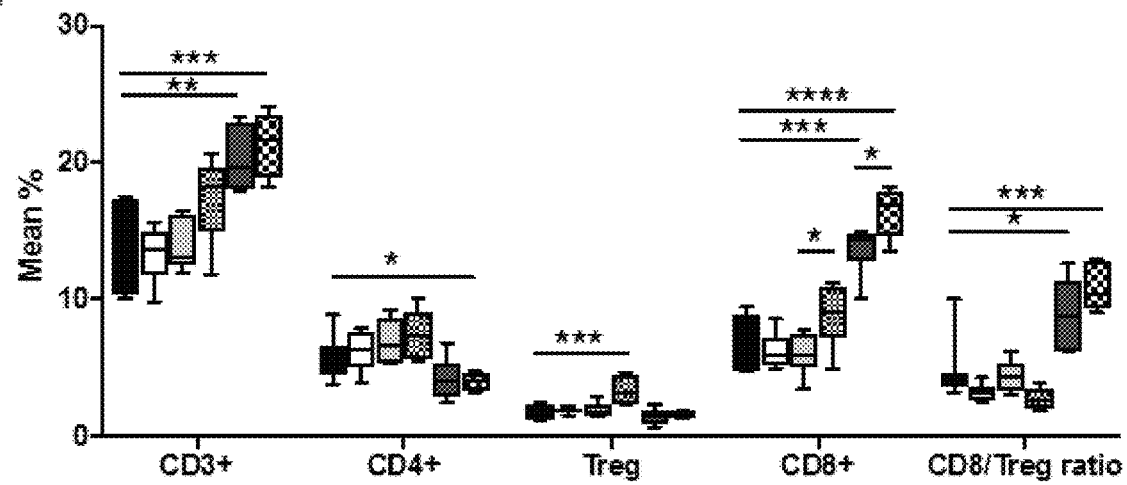
Figure 14:
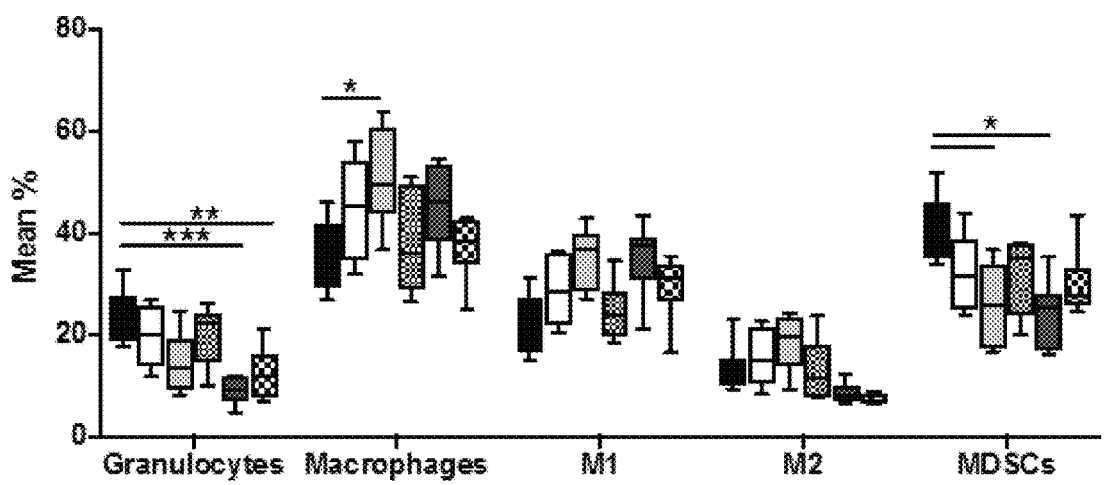
Figure 14:
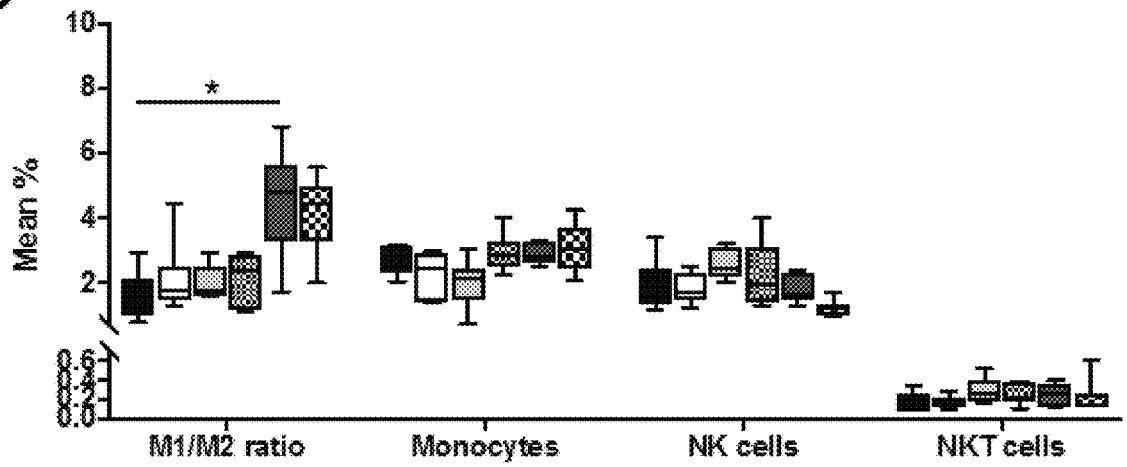

FIG. 14 shows the immune contexture of Tumor Infiltrating Lymphocytes (TILs) analysis from Pan02 pancreatic cancer mice with large tumors treated with A30$_2$-Fc, 4-1BB and PD-1 by flow cytometry (continuation of experiment in FIG. 13). Relevant leukocytes analysed infiltrating the tumor: A) CD3+ T cells, CD4+ T cells, Regulatory T cells (Treg), CD8+ T cells, and the CD8+/Treg ratio. B) Granulocytes, Macrophages, Macrophage M1-type, Macrophage M2-type, and Myeloid Derived Suppressor Cells (MDSCs). C) M1/M2 macrophage ratio, Monocytes, Natural killer cells (NK), and Natural Killer T cells (NKT). Leukocytes % are expressed as box plots showing sample maxima and minima, and each group analysed by one-way ANOVA followed by Dunnet post-hoc analysis *p<0.05; p<0.01; *p<0.001; ****p<0.0001.

Figure 15:
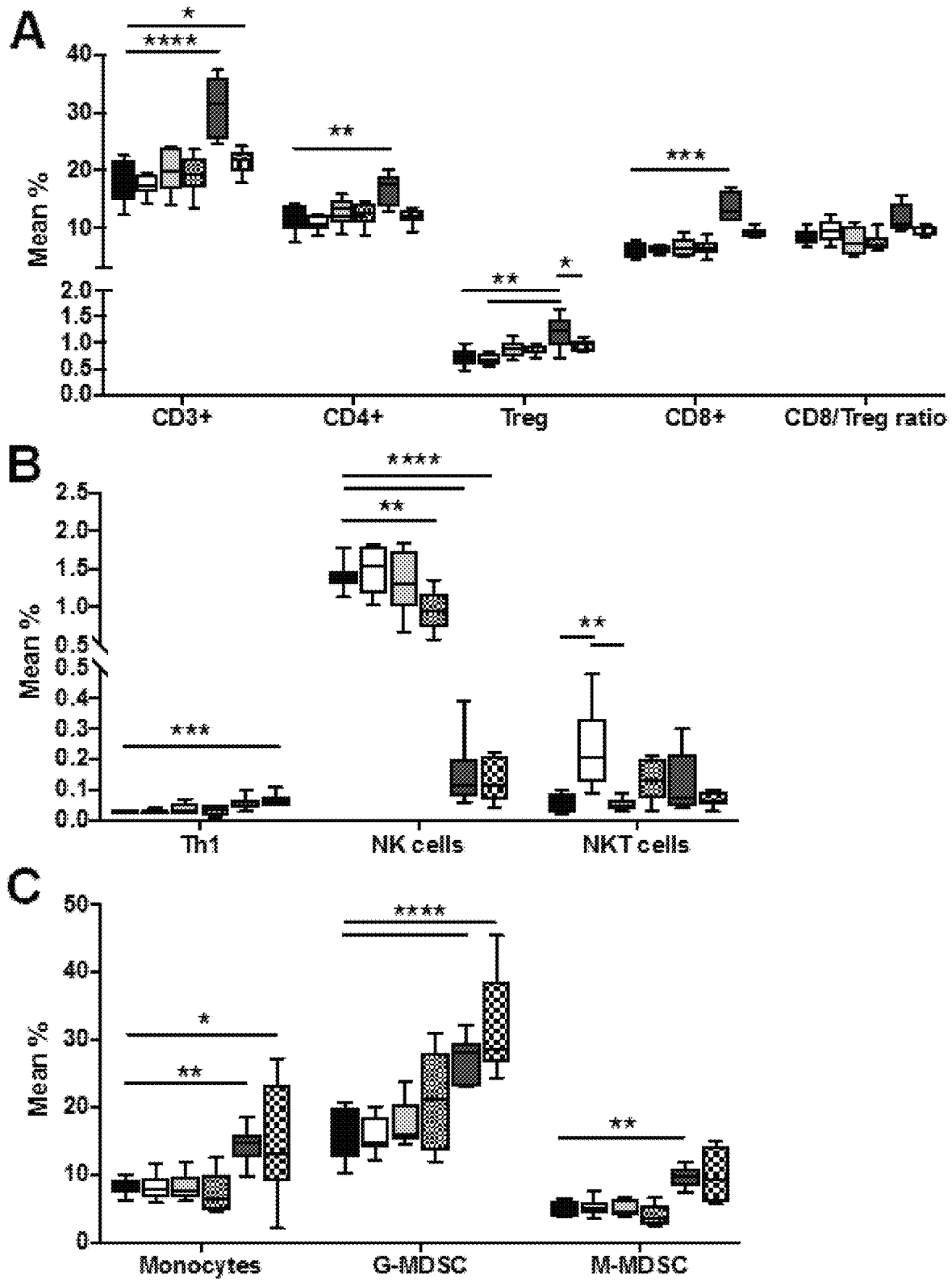

FIG. 15 shows the immune contexture of blood leukocyte analysis from treated Pan02 pancreatic cancer mice with large tumors treated with A30$_2$-Fc, 4-1 BB and PD-1 by flow cytometry (continuation of experiment in FIG. 13). Relevant leukocytes analysed present in the blood: A) CD3+ T cells, CD4+ T cells, Regulatory T cells (Treg), CD8+ T cells, and CD8+/Treg ratio. B) Th1 cells (CD4+ T cells IFNγ+), Natural Killer cells (NK), and Natural Killer T cells (NKT). C) Monocytes, Granulocyte-Myeloid Derived suppressor cells (G-MDSCs), and Monocytic-Myeloid Derived Suppressor cells (M-MDSCs). Leukocytes % are expressed as box plots showing sample maxima and minima, and each group analysed by one-way ANOVA followed by Dunnet post-hoc analysis *p<0.05; p<0.01; *p<0.001; ****p<0.0001.

Figure 16:
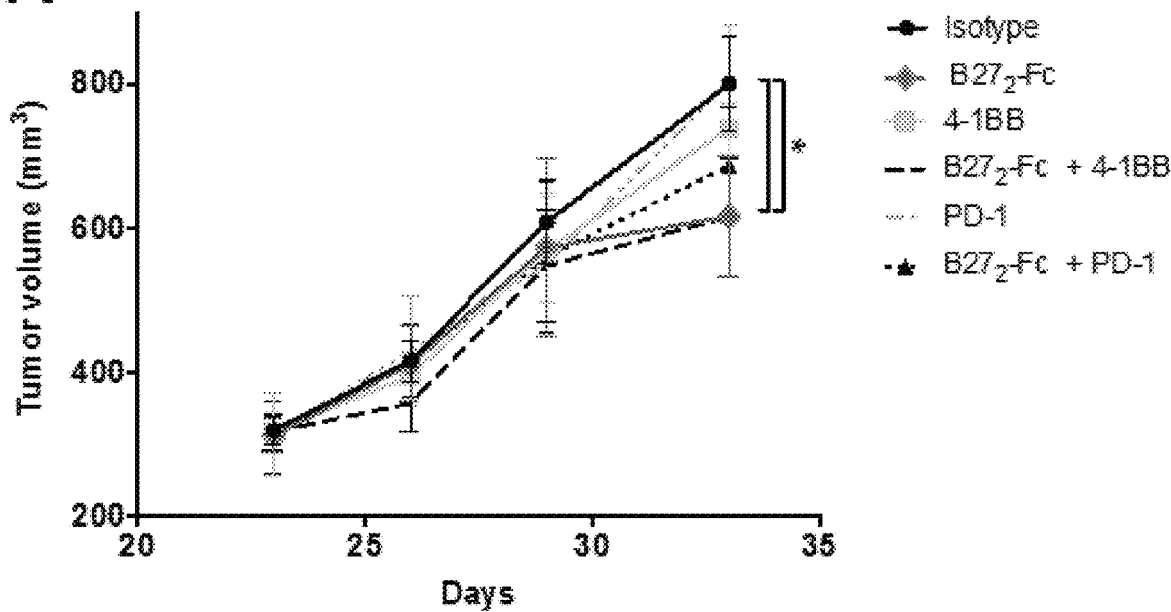
Figure 16:
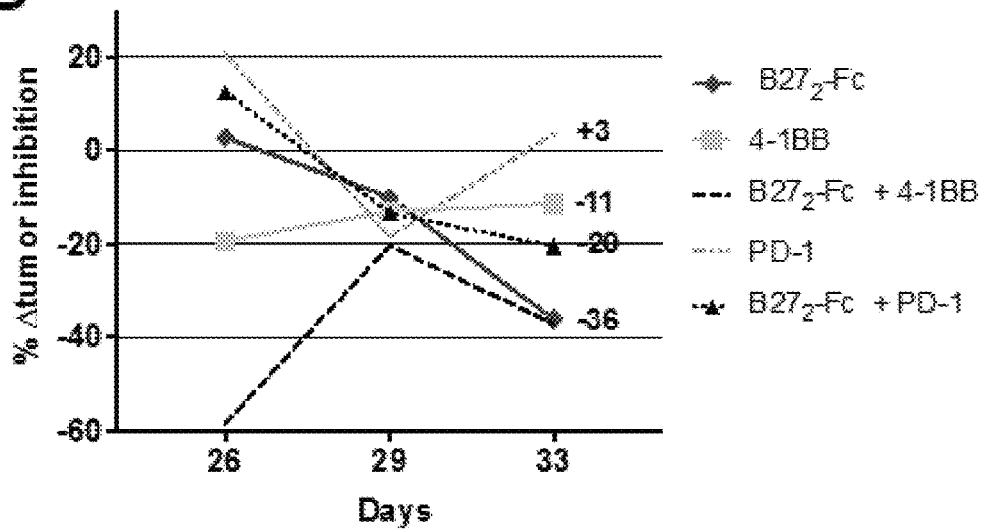

FIG. 16 shows the in vivo study of B27$_2$-Fc in combination with PD-1 and 4-1BB antibodies in large tumors of the pancreatic Pan02 syngeneic mouse model. A) Mean average tumor volume in mm$^3$ of B272-Fc treated animals (n=6). B) % Δtumor inhibition of treated mice groups compared to control. The experimental design of injection time points of substances was as follow: isotype (5 mg/Kg) biwk×2; B27$_2$-Fc (5 mg/Kg) biwk×2; 4-1BB antibody (1 mg/Kg) biwk×2 injections; B272-Fc+4-1 BB (5 mg/Kg and 1 mg/Kg, respectively) biwk×2; PD-1 antibody (5 mg/Kg) biwk×2; and B272-Fc+PD-1 (5 mg/Kg each) biwk×2. Tumor volumes are expressed as mean±SEM and analysed by two-way ANOVA followed by Bonferroni post-hoc analysis. Δtumor inhibition is calculated from the ΔT/ΔC tumor growth ratio, which represents the growth of the tumor in % from the beginning of the treatment (e.g. 300 mm$^3$), to the end volume of the treatment (e.g. 1000 mm$^3$) compared to isotype. biwk=twice a week.

Figure 17:
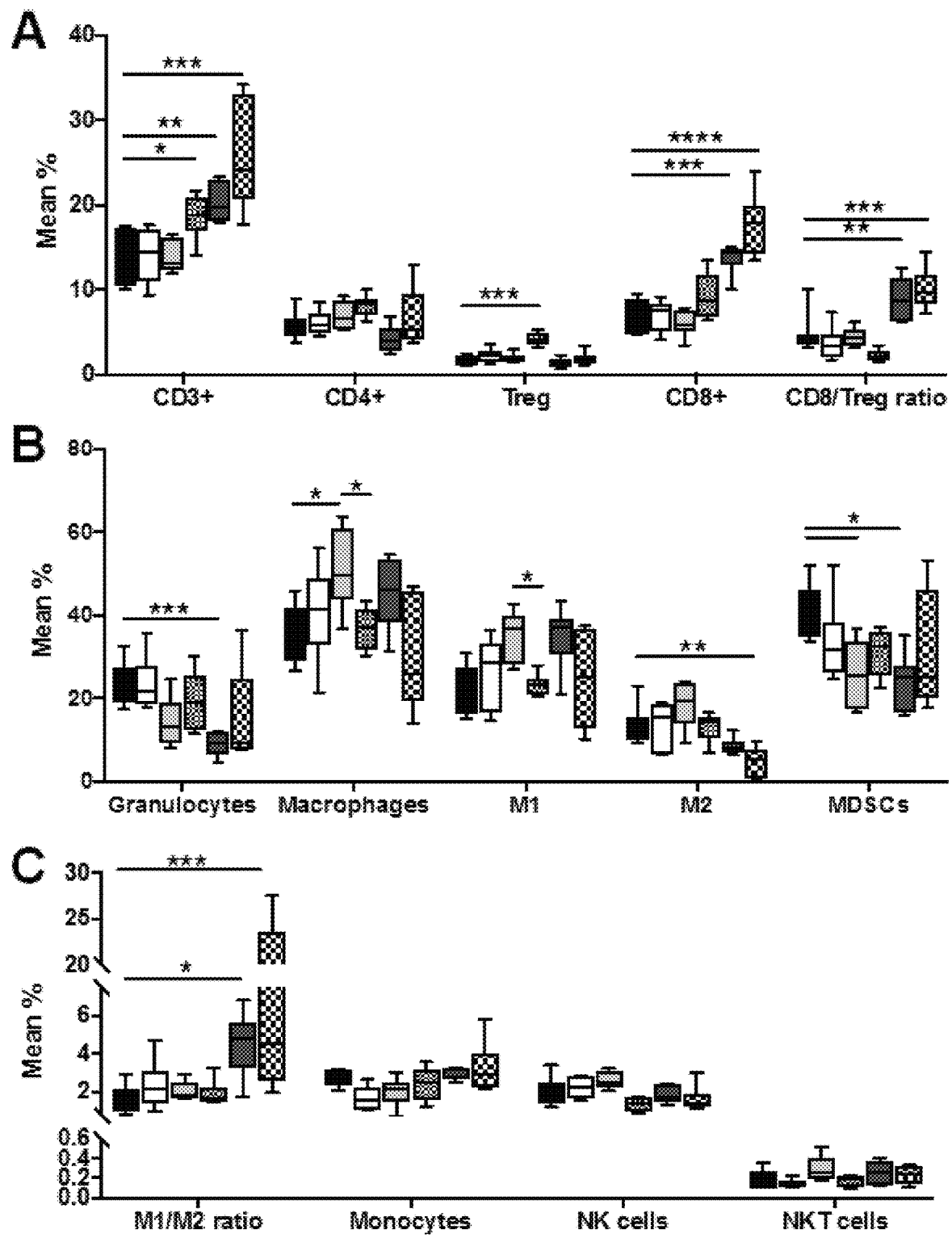

FIG. 17 shows the immune contexture of Tumor Infiltrating Lymphocytes (TILs) analysis from Pan02 pancreatic cancer mice with large tumors treated with B272-Fc, 4-1BB and PD-1 by flow cytometry (continuation of experiment in FIG. 16). Relevant leukocytes analysed infiltrating the tumor: A) CD3+ T cells, CD4+ T cells, Regulatory T cells (Treg), CD8+ T cells, and the CD8+/Treg ratio. B) Granulocytes, Macrophages, Macrophage M1-type, Macrophage M2-type, and Myeloid Derived Suppressor Cells (MDSCs). C) M1/M2 macrophage ratio, Monocytes, Natural killer cells (NK), and Natural Killer T cells (NKT). Leukocytes % are expressed as box plots showing sample maxima and minima, and each group analysed by one-way ANOVA followed by Dunnet post-hoc analysis *p<0.05; p<0.01; *p<0.001; ****p<0.0001.

Figure 18:
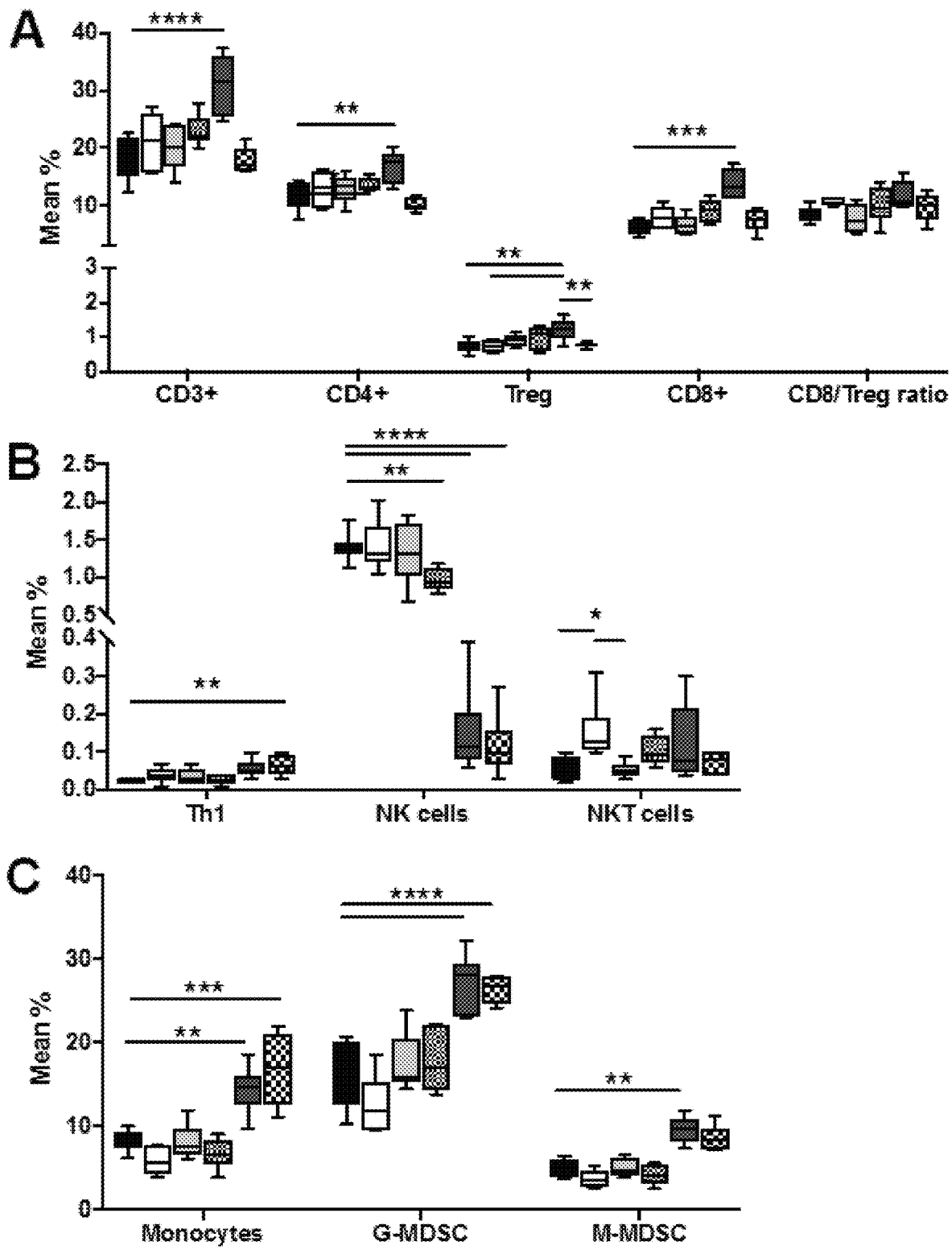

FIG. 18 shows the immune contexture of blood leukocyte analysis from treated Pan02 pancreatic cancer mice with large tumors treated with B272-Fc, 4-1 BB and PD-1 by flow cytometry (continuation of experiment in FIG. 16). Relevant leukocytes analysed present in the blood: A) CD3+ T cells, CD4+ T cells, Regulatory T cells (Treg), CD8+ T cells, and CD8+/Treg ratio. B) Th1 cells (CD4+ T cells IFNγ+), Natural Killer cells (NK), and Natural Killer T cells (NKT). C) Monocytes, Granulocyte-Myeloid Derived suppressor cells (G-MDSCs), and Monocytic-Myeloid Derived Suppressor cells (M-MDSCs). Leukocytes % are expressed as box plots showing sample maxima and minima, and each group analysed by one-way ANOVA followed by Dunnet post-hoc analysis *p<0.05; p<0.01; *p<0.001; ****p<0.0001.

Figure 19:
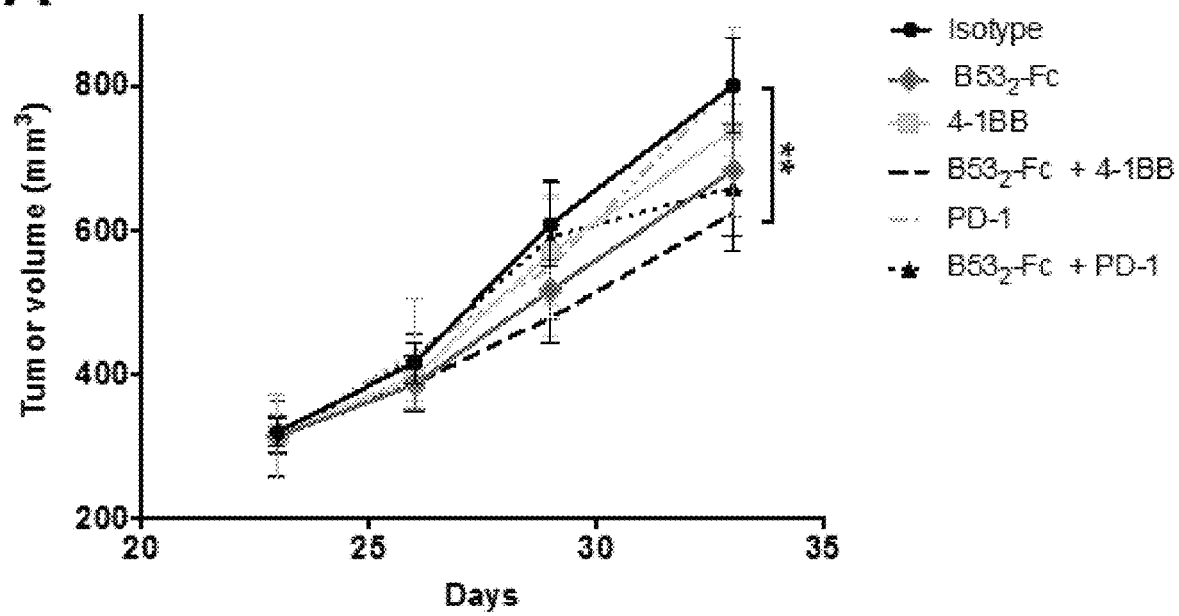
Figure 19:
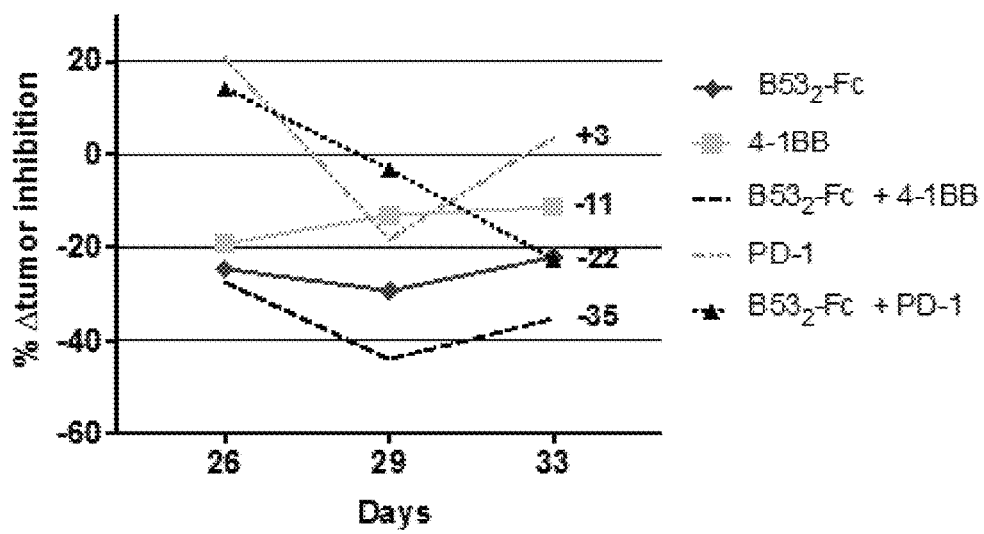

FIG. 19 shows the in vivo study of $B53_2$-Fc in combination with PD-1 and 4-1BB antibodies in large tumors of the pancreatic Pan02 syngeneic mouse model. A) Mean average tumor volume in mm³ of $B53_2$-Fc treated animals (n=6). B) % Δtumor inhibition of treated mice groups compared to control. The experimental design of injection time points of substances was as follow: isotype (5 mg/Kg) biwk×2; $B53_2$-Fc (5 mg/Kg) biwk×2; 4-1BB antibody (1 mg/Kg) biwk×2 injections; $B53_2$-Fc+4-1 BB (5 mg/Kg and 1 mg/Kg, respectively) biwk×2; PD-1 antibody (5 mg/Kg) biwk×2; and $B53_2$-Fc+PD-1 (5 mg/Kg each) biwk×2. Tumor volumes are expressed as mean±SEM and analysed by two-way ANOVA followed by Bonferroni post-hoc analysis. Δtumor inhibition is calculated from the ΔT/ΔC tumor growth ratio, which represents the growth of the tumor in % from the beginning of the treatment (e.g. 300 mm³), to the end volume of the treatment (e.g. 1000 mm³) compared to isotype. biwk=twice a week.

Figure 20:
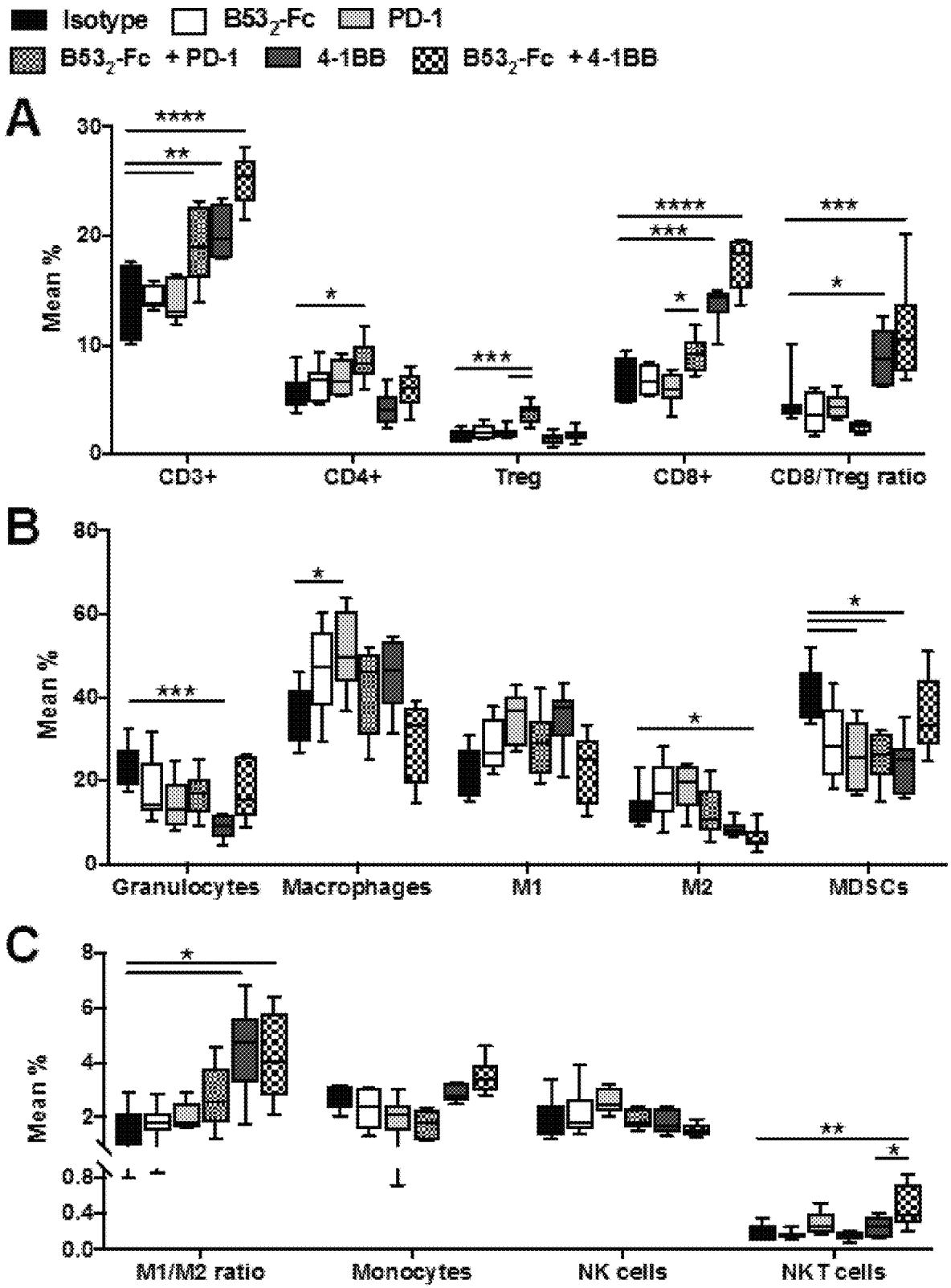

FIG. 20 shows the immune contexture of Tumor Infiltrating Lymphocytes (TILs) analysis from Pan02 pancreatic cancer mice with large tumors treated with $B53_2$-Fc, 4-1 BB and PD-1 by flow cytometry (continuation of experiment in FIG. 19). Relevant leukocytes analysed infiltrating the tumor: A) CD3+ T cells, CD4+ T cells, Regulatory T cells (Treg), CD8+ T cells, and the CD8+/Treg ratio. B) Granulocytes, Macrophages, Macrophage M1-type, Macrophage M2-type, and Myeloid Derived Suppressor Cells (MDSCs). C) M1/M2 macrophage ratio, Monocytes, Natural killer cells (NK), and Natural Killer T cells (NKT). Leukocytes % are expressed as box plots showing sample maxima and minima, and each group analysed by one-way ANOVA followed by Dunnet post-hoc analysis *p<0.05; p<0.01; *p<0.001; ****p<0.0001.

Figure 21:
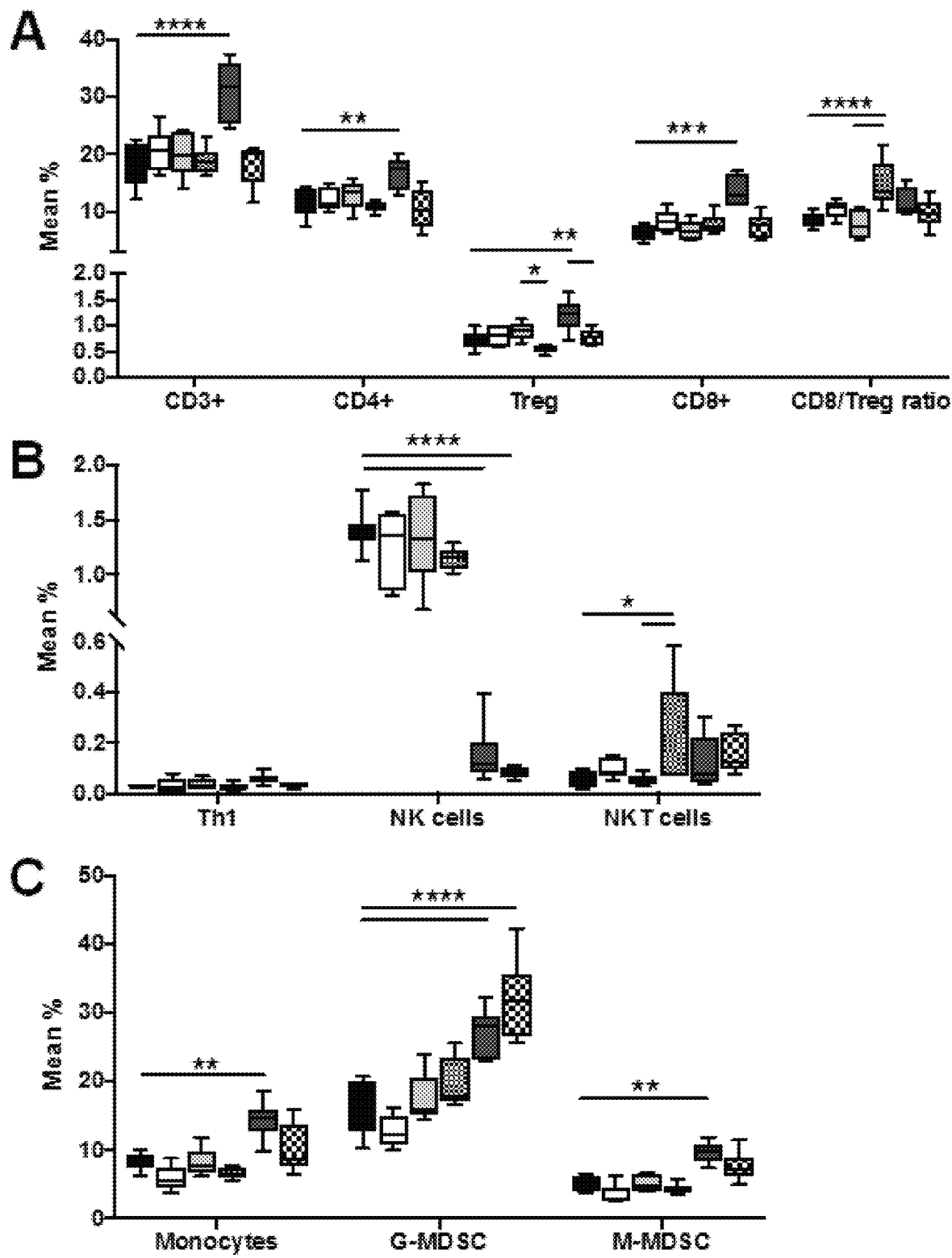

FIG. 21 shows the immune contexture of blood leukocyte analysis from treated Pan02 pancreatic cancer mice with large tumors treated with $B53_2$-Fc, 4-1 BB and PD-1 by flow cytometry (continuation of experiment in FIG. 19). Relevant leukocytes analysed present in the blood: A) CD3+ T cells, CD4+ T cells, Regulatory T cells (Treg), CD8+ T cells, and CD8+/Treg ratio. B) Th1 cells (CD4+ T cells IFNγ+), Natural Killer cells (NK), and Natural Killer T cells (NKT). C) Monocytes, Granulocyte-Myeloid Derived suppressor cells (G-MDSCs), and Monocytic-Myeloid Derived Suppressor cells (M-MDSCs). Leukocytes % are expressed as box plots showing sample maxima and minima, and each group analysed by one-way ANOVA followed by Dunnet post-hoc analysis *p<0.05; p<0.01; *p<0.001; ****p<0.0001.

Figure 22:
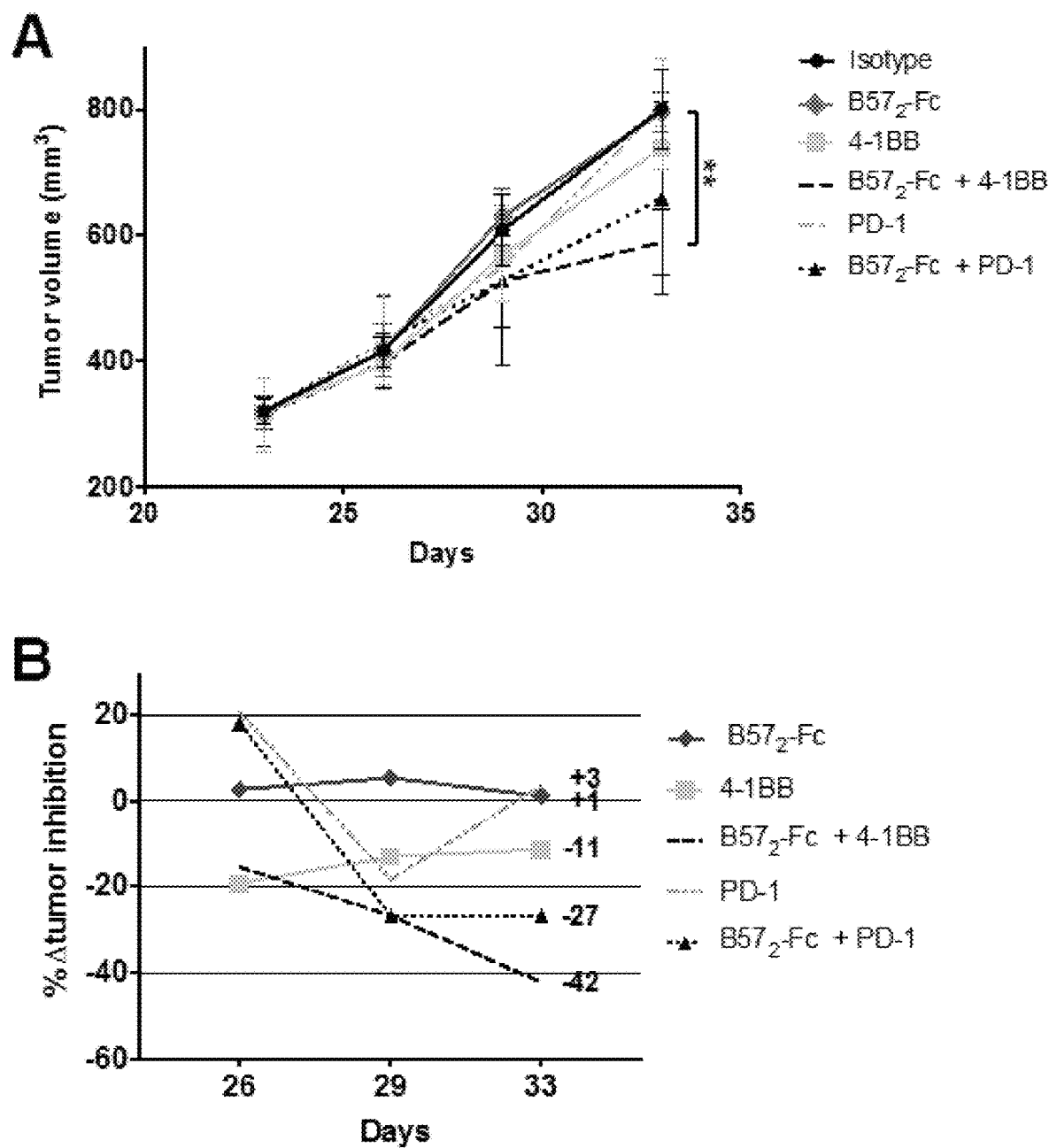

FIG. 22 shows the in vivo study of $B57_2$-Fc in combination with PD-1 and 4-1 BB antibodies in large tumors of the pancreatic Pan02 syngeneic mouse model. A) Mean average tumor volume in mm³ of $B57_2$-Fc treated animals (n=6). B) % Δtumor inhibition of treated mice groups compared to control. The experimental design of injection time points of substances was as follow: isotype (5 mg/Kg) biwk×2; $B57_2$-Fc (5 mg/Kg) biwk×2; 4-1 BB antibody (1 mg/Kg) biwk×2 injections; $B57_2$-Fc+4-1 BB (5 mg/Kg and 1 mg/Kg, respectively) biwk×2; PD-1 antibody (5 mg/Kg) biwk×2; and $B57_2$-Fc+PD-1 (5 mg/Kg each) biwk×2. Tumor volumes are expressed as mean±SEM and analysed by two-way ANOVA followed by Bonferroni post-hoc analysis. Δtumor inhibition is calculated from the ΔT/ΔC tumor growth ratio, which represents the growth of the tumor in % from the beginning of the treatment (e.g. 300 mm³), to the end volume of the treatment (e.g. 1000 mm³) compared to isotype. biwk=twice a week.

Figure 23:
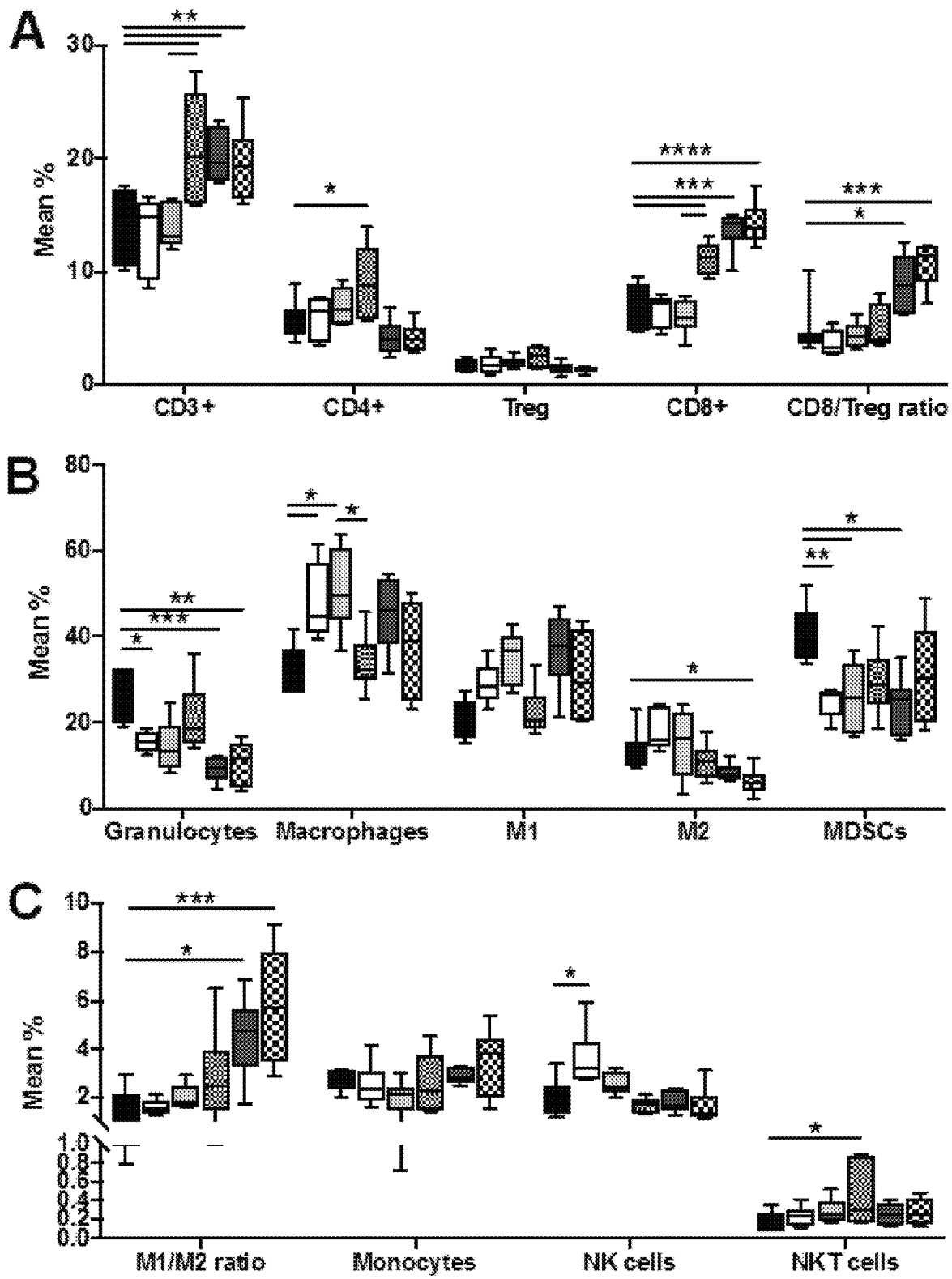

FIG. 23 shows the immune contexture of Tumor Infiltrating Lymphocytes (TILs) analysis from Pan02 pancreatic cancer mice with large tumors treated with $B57_2$-Fc, 4-1 BB and PD-1 by flow cytometry (continuation of experiment in FIG. 22). Relevant leukocytes analysed infiltrating the tumor: A) CD3+ T cells, CD4+ T cells, Regulatory T cells (Treg), CD8+ T cells, and the CD8+/Treg ratio. B) Granulocytes, Macrophages, Macrophage M1-type, Macrophage M2-type, and Myeloid Derived Suppressor Cells (MDSCs). C) M1/M2 macrophage ratio, Monocytes, Natural killer cells (NK), and Natural Killer T cells (NKT). Leukocytes % are expressed as box plots showing sample maxima and minima, and each group analysed by one-way ANOVA followed by Dunnet post-hoc analysis *p<0.05; p<0.01; *p<0.001; ****p<0.0001.

Figure 24:
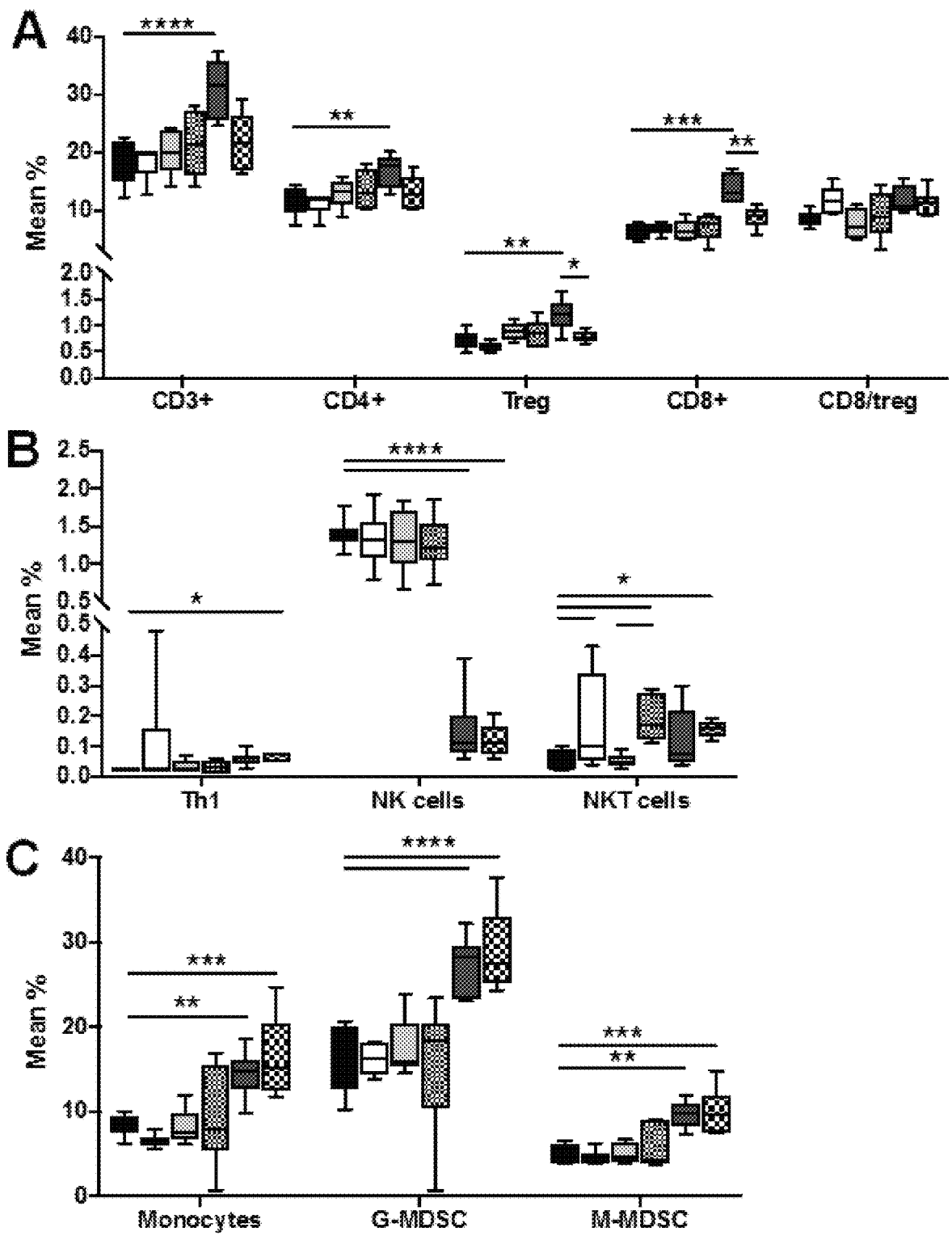

FIG. 24 shows the immune contexture of blood leukocyte analysis from treated Pan02 pancreatic cancer mice with large tumors treated with $B57_2$-Fc, 4-1 BB and PD-1 by flow cytometry (continuation of experiment in FIG. 22). Relevant leukocytes analysed present in the blood: A) CD3+ T cells, CD4+ T cells, Regulatory T cells (Treg), CD8+ T cells, and CD8+/Treg ratio. B) Th1 cells (CD4+ T cells IFNγ+), Natural Killer cells (NK), and Natural Killer T cells (NKT). C) Monocytes, Granulocyte-Myeloid Derived suppressor cells (G-MDSCs), and Monocytic-Myeloid Derived Suppressor cells (M-MDSCs). Leukocytes % are expressed as box plots showing sample maxima and minima, and each group analysed by one-way ANOVA followed by Dunnet post-hoc analysis *p<0.05; p<0.01; *p<0.001; ****p<0.0001.

Figure 25:
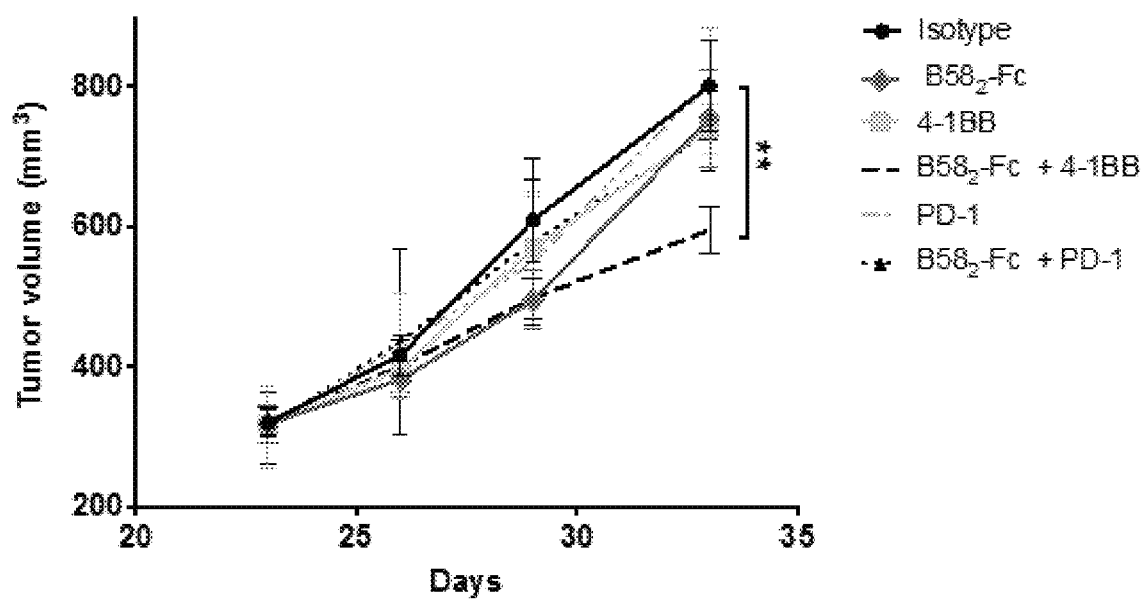
Figure 25:
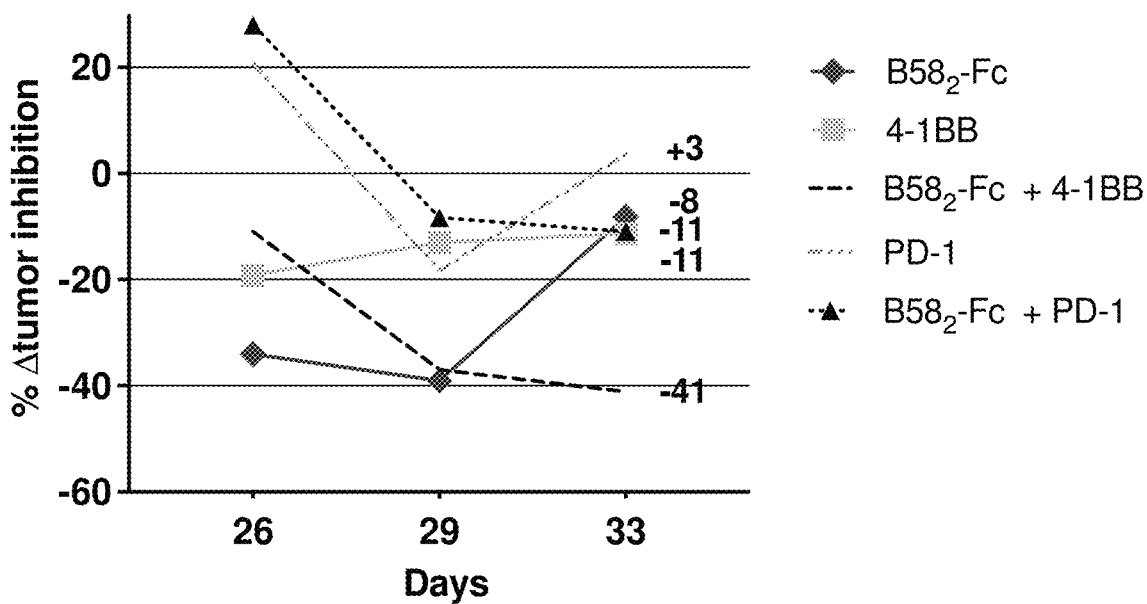

FIG. 25 shows the in vivo study of $B58_2$-Fc in combination with PD-1 and 4-1BB antibodies in large tumors of the pancreatic Pan02 syngeneic mouse model. A) Mean average tumor volume in mm³ of $B58_2$-Fc treated animals (n=6). B) % Δtumor inhibition of treated mice groups compared to control. The experimental design of injection time points of substances was as follow: isotype (5 mg/Kg) biwk×2; $B58_2$-Fc (5 mg/Kg) biwk×2; 4-1BB antibody (1 mg/Kg) biwk×2 injections; $B58_2$-Fc+4-1 BB (5 mg/Kg and 1 mg/Kg, respectively) biwk×2; PD-1 antibody (5 mg/Kg) biwk×2; and $B58_2$-Fc+PD-1 (5 mg/Kg each) biwk×2. Tumor volumes are expressed as mean±SEM and analysed by two-way ANOVA followed by Bonferroni post-hoc analysis. Δtumor inhibition is calculated from the ΔT/ΔC tumor growth ratio, which represents the growth of the tumor in % from the beginning of the treatment (e.g. 300 mm³), to the end volume of the treatment (e.g. 1000 mm³) compared to isotype. biwk=twice a week.

Figure 26:
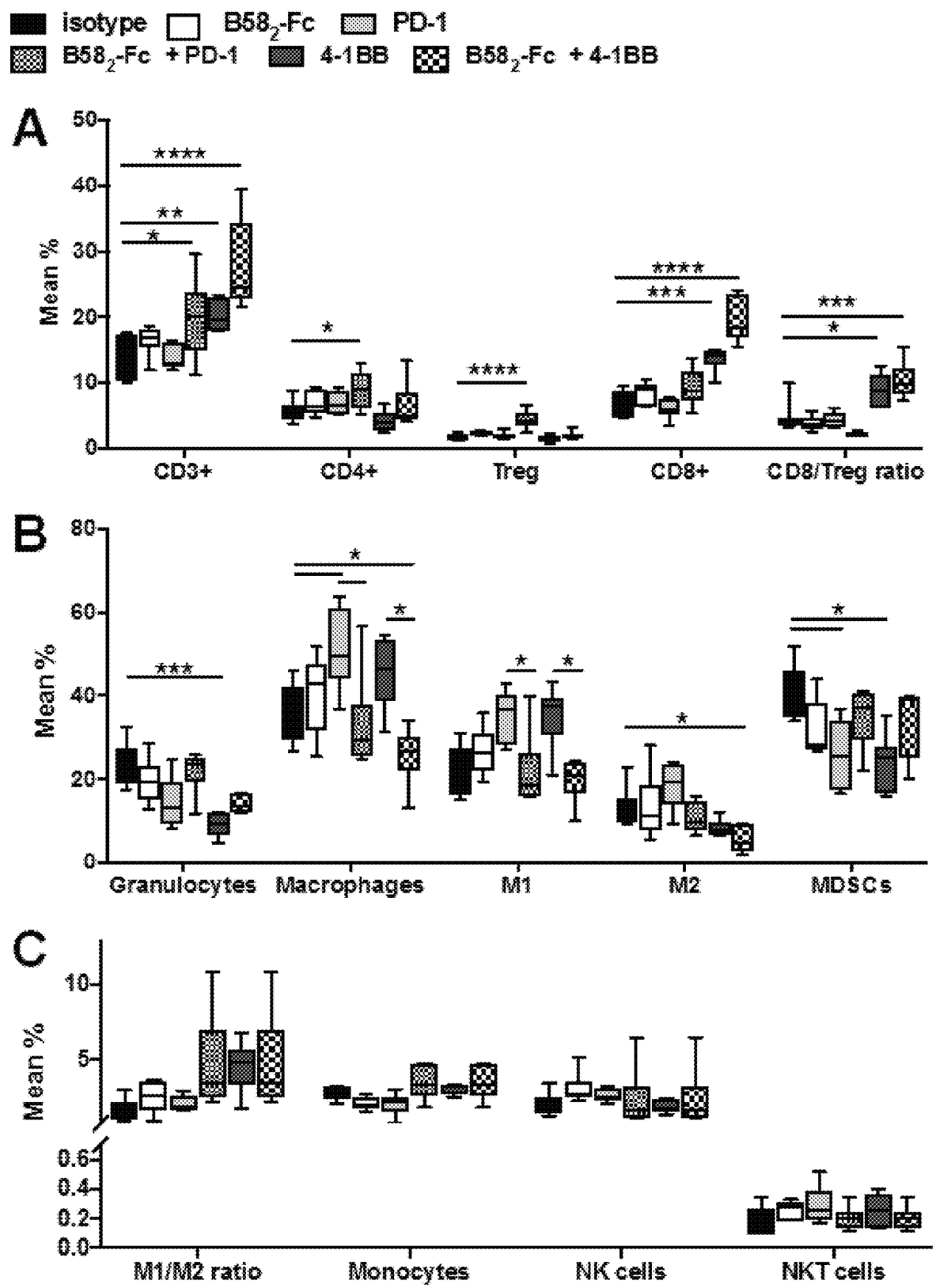

FIG. 26 shows the immune contexture of Tumor Infiltrating Lymphocytes (TILs) analysis from Pan02 pancreatic cancer mice with large tumors treated with $B58_2$-Fc, 4-1BB and PD-1 by flow cytometry (continuation of experiment in FIG. 25). Relevant leukocytes analysed infiltrating the tumor: A) CD3+ T cells, CD4+ T cells, Regulatory T cells (Treg), CD8+ T cells, and the CD8+/Treg ratio. B) Granulocytes, Macrophages, Macrophage M1-type, Macrophage M2-type, and Myeloid Derived Suppressor Cells (MDSCs). C) M1/M2 macrophage ratio, Monocytes, Natural killer cells (NK), and Natural Killer T cells (NKT). Leukocytes % are expressed as box plots showing sample maxima and minima, and each group analysed by one-way ANOVA followed by Dunnet post-hoc analysis *p<0.05; p<0.01; *p<0.001; ****p<0.0001.

Figure 27:
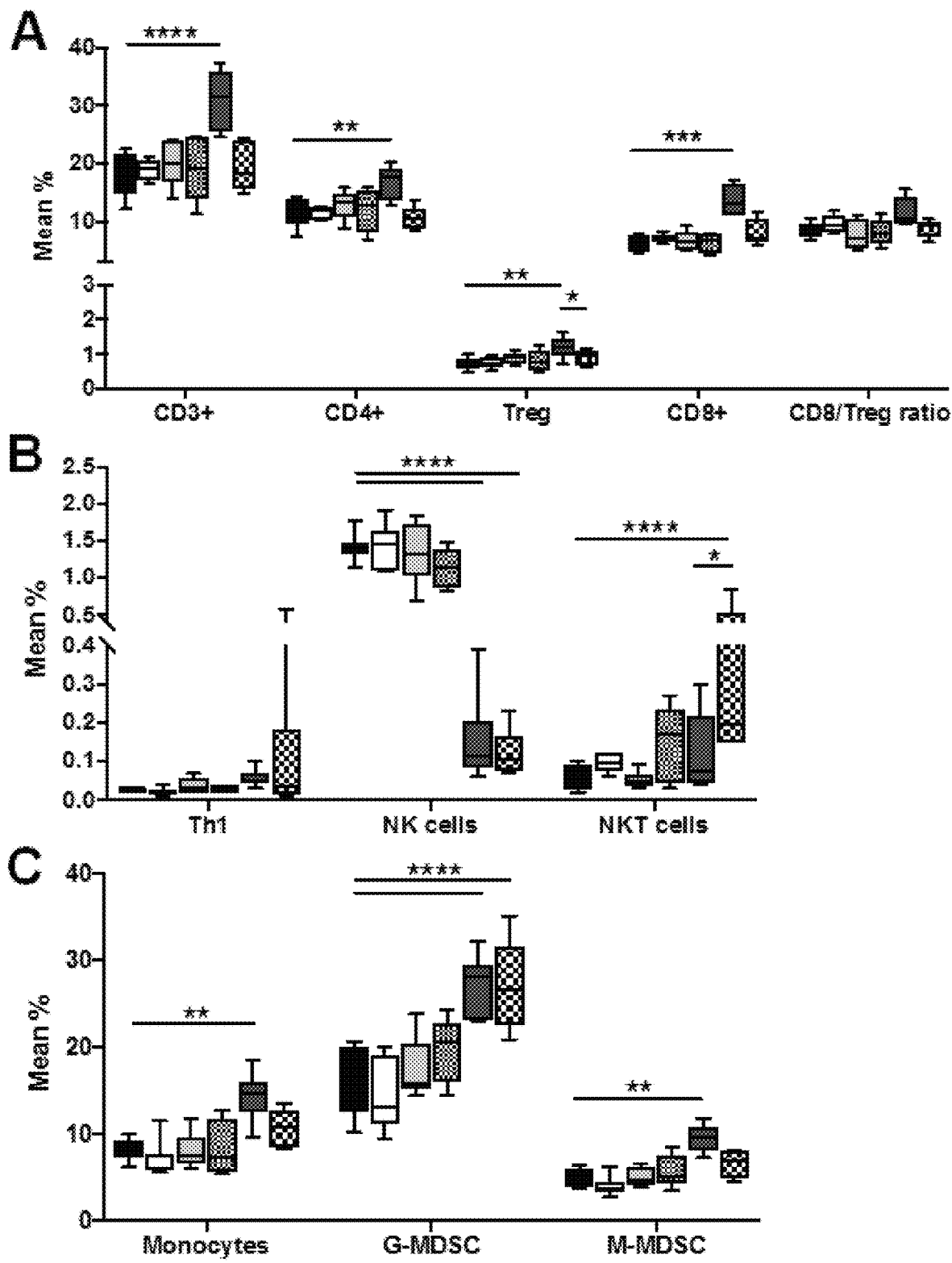

FIG. 27 shows the immune contexture of blood leukocyte analysis from treated Pan02 pancreatic cancer mice with large tumors treated with $B58_2$-Fc, 4-1 BB and PD-1 by flow cytometry (continuation of experiment in FIG. 25). Relevant leukocytes analysed present in the blood: A) CD3+ T cells, CD4+ T cells, Regulatory T cells (Treg), CD8+ T cells, and CD8+/Treg ratio. B) Th1 cells (CD4+ T cells IFNγ+), Natural Killer cells (NK), and Natural Killer T cells (NKT). C) Monocytes, Granulocyte-Myeloid Derived suppressor cells (G-MDSCs), and Monocytic-Myeloid Derived Suppressor cells (M-MDSCs). Leukocytes % are expressed as box plots showing sample maxima and minima, and each group analysed by one-way ANOVA followed by Dunnet post-hoc analysis *p<0.05; p<0.01; *p<0.001; ****p<0.0001.

Figure 28:
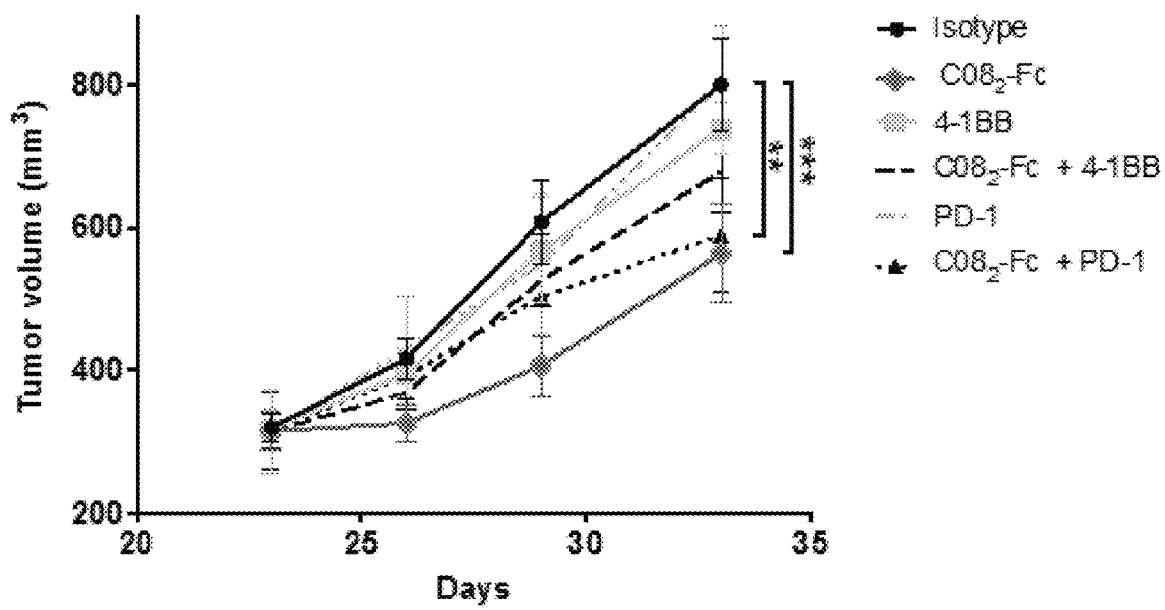
Figure 28:
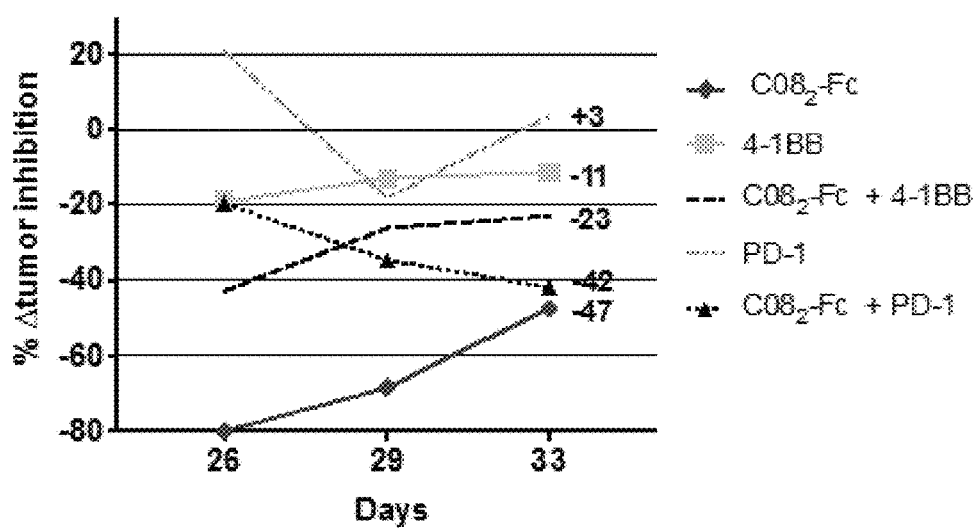

FIG. 28 shows the in vivo study of $C08_2$-Fc in combination with PD-1 and 4-1 BB antibodies in large tumors of the pancreatic Pan02 syngeneic mouse model. A) Mean average tumor volume in $mm^3$ of $C08_2$-Fc treated animals (n=6). B) % Δtumor inhibition of treated mice groups compared to control. The experimental design of injection time points of substances was as follow: isotype (5 mg/Kg) biwk×2; $C08_2$-Fc (5 mg/Kg) biwk×2; 4-1 BB antibody (1 mg/Kg) biwk×2 injections; $C08_2$-Fc+4-1 BB (5 mg/Kg and 1 mg/Kg, respectively) biwk×2; PD-1 antibody (5 mg/Kg) biwk×2; and $C08_2$-Fc+PD-1 (5 mg/Kg each) biwk×2. Tumor volumes are expressed as mean±SEM and analysed by two-way ANOVA followed by Bonferroni post-hoc analysis. Δtumor inhibition is calculated from the ΔT/ΔC tumor growth ratio, which represents the growth of the tumor in % from the beginning of the treatment (e.g. 300 $mm^3$), to the end volume of the treatment (e.g. 1000 $mm^3$) compared to isotype. biwk=twice a week.

Figure 29:
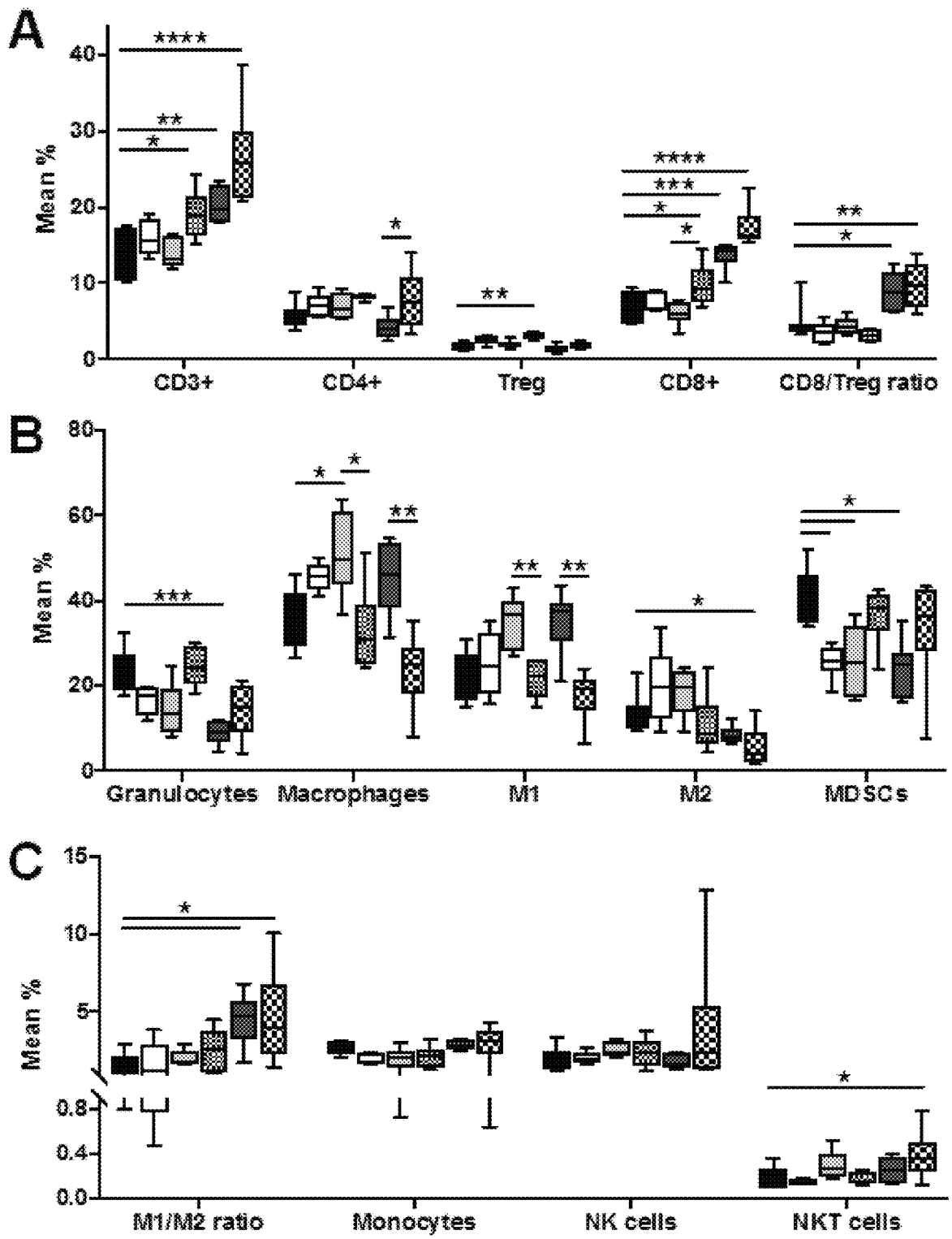

FIG. 29 shows the immune contexture of Tumor Infiltrating Lymphocytes (TILs) analysis from Pan02 pancreatic cancer mice with large tumors treated with $C08_2$-Fc, 4-1 BB and PD-1 by flow cytometry (continuation of experiment in FIG. 28). Relevant leukocytes analysed infiltrating the tumor: A) CD3+ T cells, CD4+ T cells, Regulatory T cells (Treg), CD8+ T cells, and the CD8+/Treg ratio. B) Granulocytes, Macrophages, Macrophage M1-type, Macrophage M2-type, and Myeloid Derived Suppressor Cells (MDSCs). C) M1/M2 macrophage ratio, Monocytes, Natural killer cells (NK), and Natural Killer T cells (NKT). Leukocytes % are expressed as box plots showing sample maxima and minima, and each group analysed by one-way ANOVA followed by Dunnet post-hoc analysis *p<0.05; p<0.01; *p<0.001; ****p<0.0001.

Figure 30:
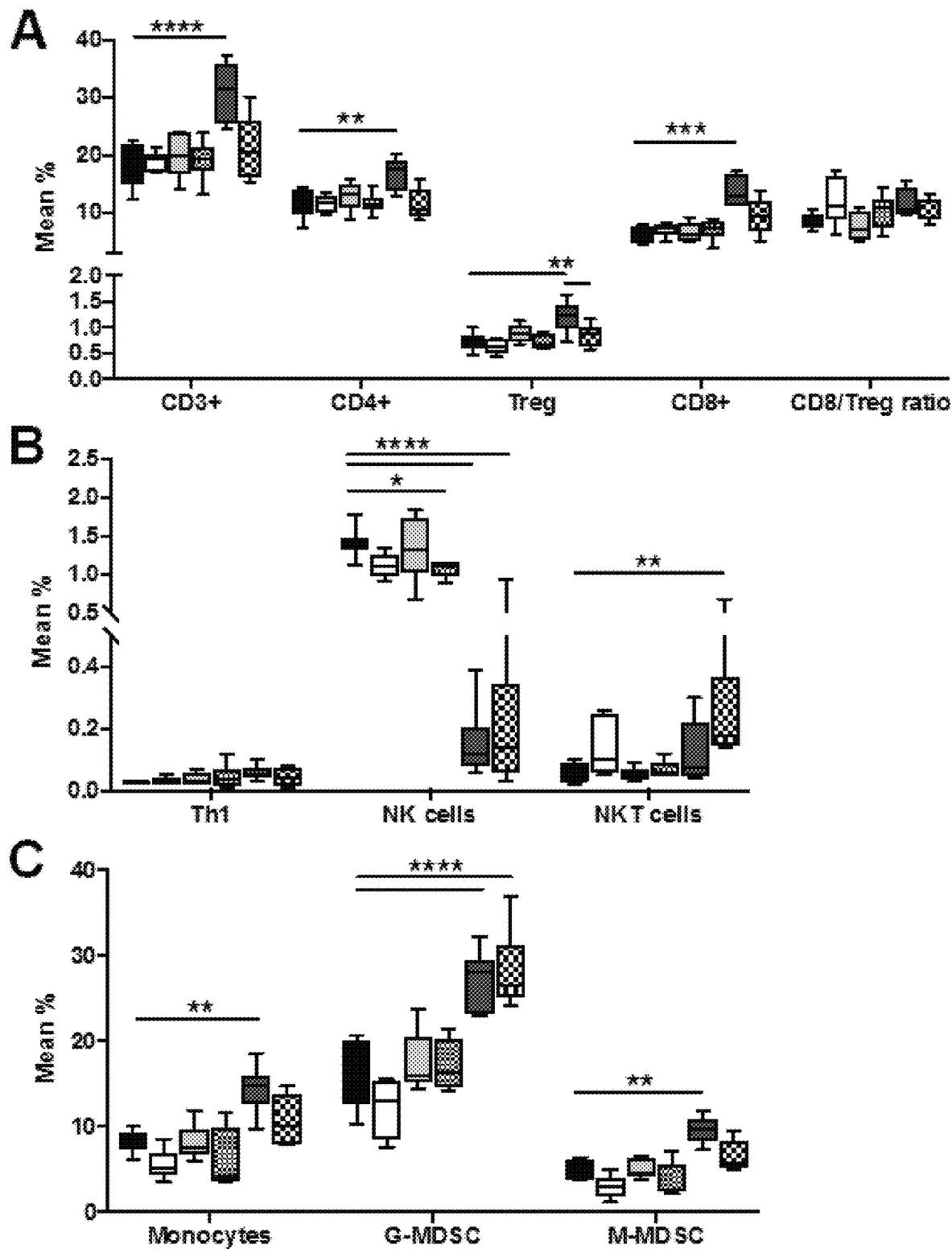

FIG. 30 shows the immune contexture of blood leukocyte analysis from treated Pan02 pancreatic cancer mice with large tumors treated with $C08_2$-Fc, 4-1 BB and PD-1 by flow cytometry (continuation of experiment in FIG. 28). Relevant leukocytes analysed present in the blood: A) CD3+ T cells, CD4+ T cells, Regulatory T cells (Treg), CD8+ T cells, and CD8+/Treg ratio. B) Th1 cells (CD4+ T cells IFNγ+), Natural Killer cells (NK), and Natural Killer T cells (NKT). C) Monocytes, Granulocyte-Myeloid Derived suppressor cells (G-MDSCs), and Monocytic-Myeloid Derived Suppressor cells (M-MDSCs). Leukocytes % are expressed as box plots showing sample maxima and minima, and each group analysed by one-way ANOVA followed by Dunnet post-hoc analysis *p<0.05; p<0.01; *p<0.001; ****p<0.0001.

Figure 31:
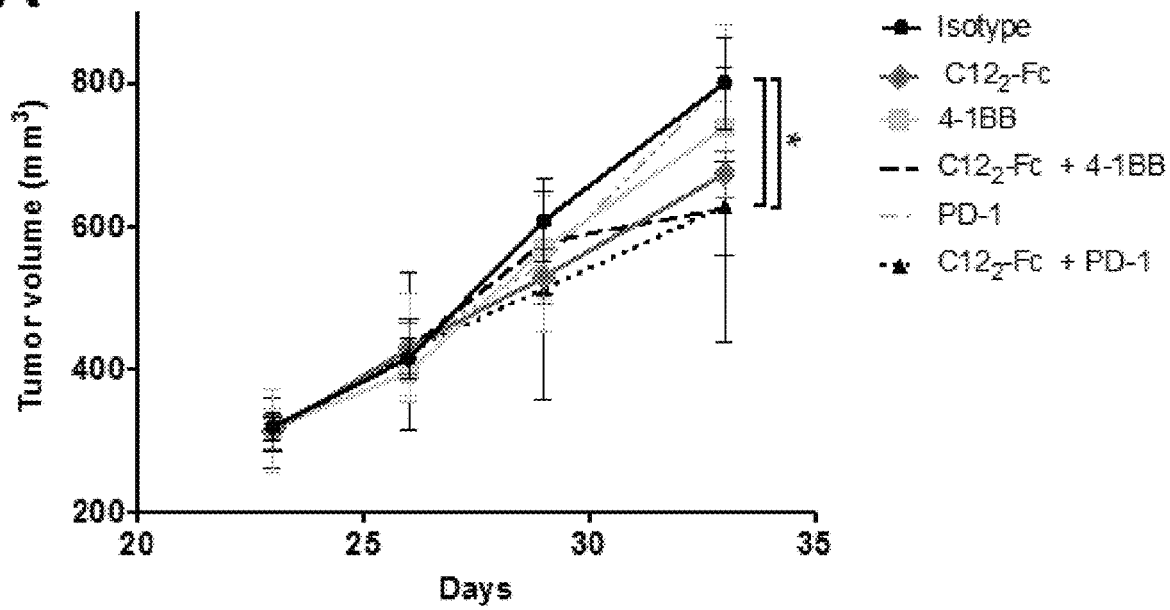
Figure 31:
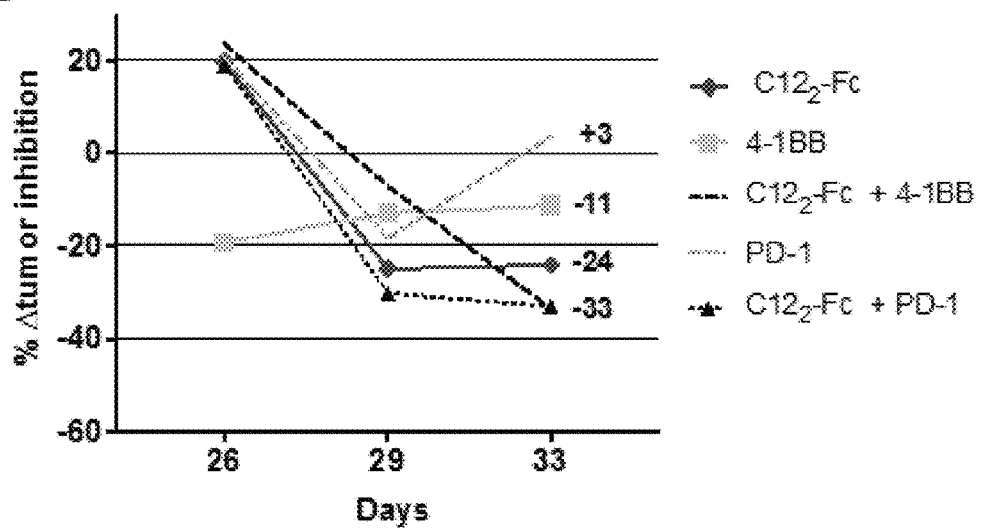

FIG. 31 shows the in vivo study of $C12_2$-Fc in combination with PD-1 and 4-1 BB antibodies in large tumors of the pancreatic Pan02 syngeneic mouse model. A) Mean average tumor volume in $mm^3$ of $C12_2$-Fc treated animals (n=6). B) % Δtumor inhibition of treated mice groups compared to control. The experimental design of injection time points of substances was as follow: isotype (5 mg/Kg) biwk×2; $C12_2$-Fc (5 mg/Kg) biwk×2; 4-1 BB antibody (1 mg/Kg) biwk×2 injections; $C12_2$-Fc+4-1 BB (5 mg/Kg and 1 mg/Kg, respectively) biwk×2; PD-1 antibody (5 mg/Kg) biwk×2; and $C12_2$-Fc+PD-1 (5 mg/Kg each) biwk×2. Tumor volumes are expressed as mean±SEM and analysed by two-way ANOVA followed by Bonferroni post-hoc analysis. Δtumor inhibition is calculated from the ΔT/ΔC tumor growth ratio, which represents the growth of the tumor in % from the beginning of the treatment (e.g. 300 $mm^3$), to the end volume of the treatment (e.g. 1000 $mm^3$) compared to isotype. biwk=twice a week.

Figure 32:
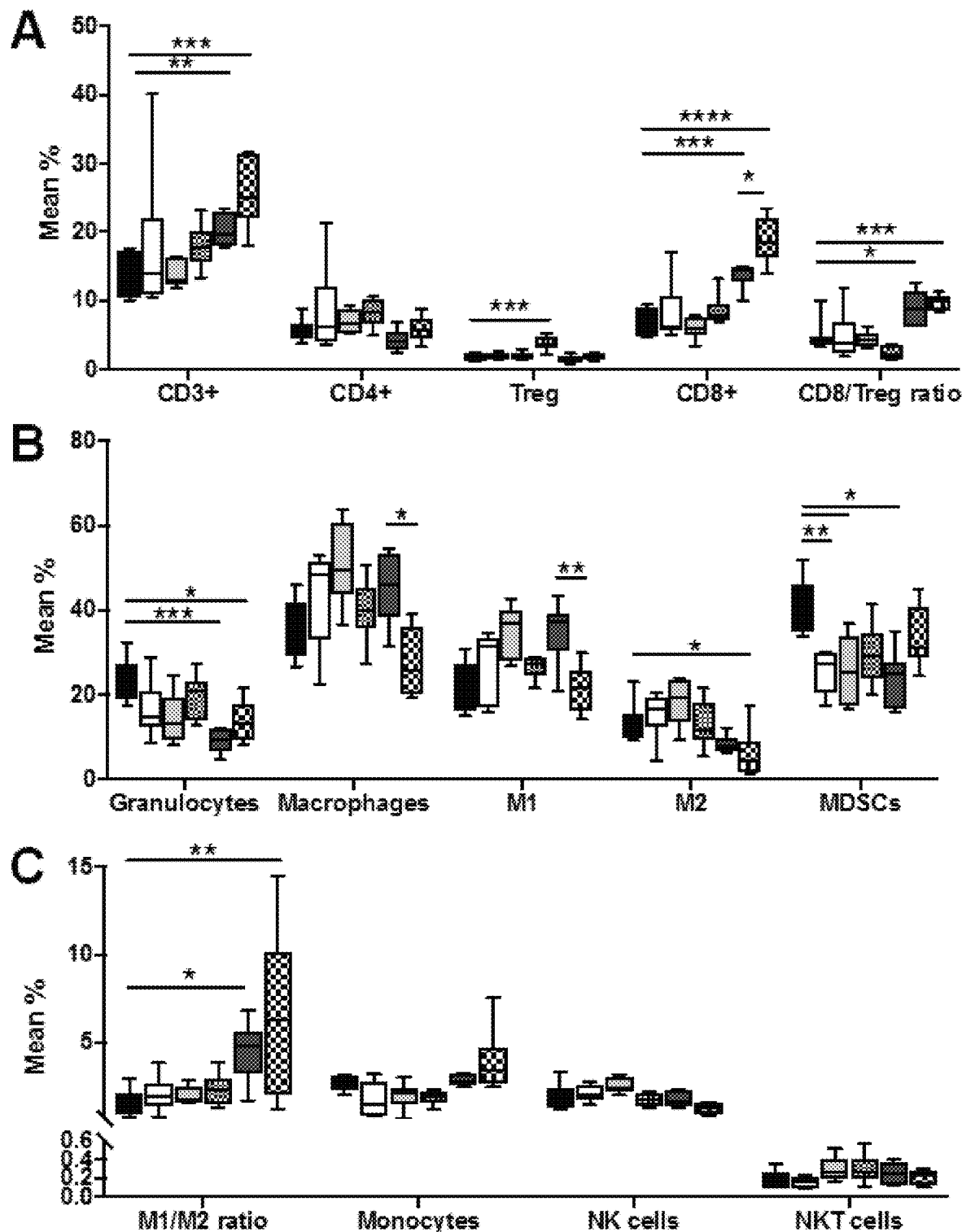

FIG. 32 shows the immune contexture of Tumor Infiltrating Lymphocytes (TILs) analysis from Pan02 pancreatic cancer mice with large tumors treated with $C12_2$-Fc, 4-1BB and PD-1 by flow cytometry (continuation of experiment in FIG. 31). Relevant leukocytes analysed infiltrating the tumor: A) CD3+ T cells, CD4+ T cells, Regulatory T cells (Treg), CD8+ T cells, and the CD8+/Treg ratio. B) Granulocytes, Macrophages, Macrophage M1-type, Macrophage M2-type, and Myeloid Derived Suppressor Cells (MDSCs). C) M1/M2 macrophage ratio, Monocytes, Natural killer cells (NK), and Natural Killer T cells (NKT). Leukocytes % are expressed as box plots showing sample maxima and minima, and each group analysed by one-way ANOVA followed by Dunnet post-hoc analysis *p<0.05; p<0.01; *p<0.001; ****p<0.0001.

Figure 33:
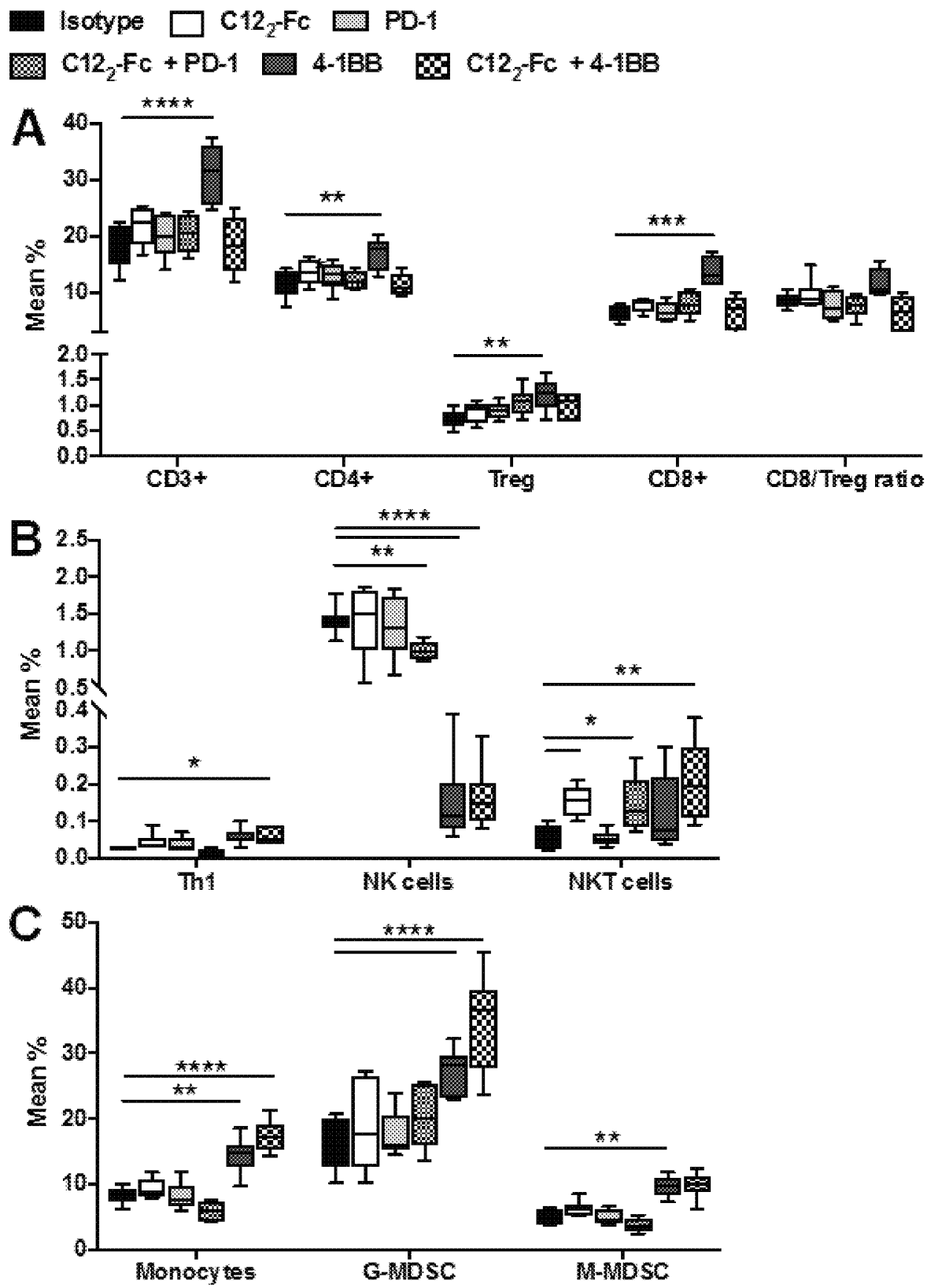

FIG. 33 shows the immune contexture of blood leukocyte analysis from treated Pan02 pancreatic cancer mice with large tumors treated with $C12_2$-Fc, 4-1 BB and PD-1 by flow cytometry (continuation of experiment in FIG. 31). Relevant leukocytes analysed present in the blood: A) CD3+ T cells, CD4+ T cells, Regulatory T cells (Treg), CD8+T cells, and CD8+/Treg ratio. B) Th1 cells (CD4+ T cells IFNγ+), Natural Killer cells (NK), and Natural Killer T cells (NKT). C) Monocytes, Granulocyte-Myeloid Derived suppressor cells (G-MDSCs), and Monocytic-Myeloid Derived Suppressor cells (M-MDSCs). Leukocytes % are expressed as box plots showing sample maxima and minima, and each group analysed by one-way ANOVA followed by Dunnet post-hoc analysis *p<0.05; p<0.01; *p<0.001; ****p<0.0001.

BRIEF DESCRIPTION OF THE DESCRIBED SEQUENCES

The amino acid sequences provided herewith are shown using standard three letter code for amino acids, as defined in 37 C.F.R. 1.822. The Sequence Listing is submitted as an ASCII text file named 95083_303_4001_ST25.txt, created Mar. 7, 2022, about 25 KB, which is incorporated by reference herein.

DETAILED DESCRIPTION

Terms and Definitions

Amino acid sequences are given from amino to carboxyl terminus. Capital letters for sequence positions refer to L-amino acids in the one-letter code (Stryer, Biochemistry, $3^{rd}$ ed. p. 21).

The term open conformer as used in the present specification refers to an isolated HLA heavy chain molecule not associated to β2-microglobulin either as a monomer or as a dimer (homodimer or heterodimer). Certain embodiments of the open conformers disclosed herein are fusion protein monomers or dimers, wherein the HLA heavy chain is covalently linked to a stabilizing polypeptide region, particularly a crystallizable fragment immunoglobulin domain.

In the context of the present specification the terms sequence identity and percentage of sequence identity refer to the values determined by comparing two aligned sequences. Methods for alignment of sequences for comparison are well-known in the art. Alignment of sequences for comparison may be conducted by the local homology algorithm of Smith and Waterman, Adv. Appl. Math. 2:482 (1981), by the global alignment algorithm of Needleman and Wunsch, J. Mol. Biol. 48:443 (1970), by the search for similarity method of Pearson and Lipman, Proc. Nat. Acad. Sci. 85:2444 (1988) or by computerized implementations of these algorithms, including, but not limited to: CLUSTAL, GAP, BESTFIT, BLAST, FASTA and TFASTA. Software for performing BLAST analyses is publicly available, e.g., through the National Center for Biotechnology-Information (http://blast.ncbi.nlm.nih.gov/). One example for comparison of amino acid sequences is the BLASTP algorithm that uses the default settings: Expect threshold: 10; Word size: 3; Max matches in a query range: 0; Matrix: BLOSUM62; Gap Costs: Existence 11, Extension 1; Compositional adjustments: Conditional compositional score matrix adjustment. One such example for comparison of nucleic acid sequences is the BLASTN algorithm that uses the default settings: Expect threshold: 10; Word size: 28; Max matches in a query range: 0; Match/Mismatch Scores: 1.-2; Gap costs: Linear. Unless otherwise stated, sequence identity values provided herein refer to the value obtained with the BLAST suite of programs (Altschul et al., J. Mol. Biol. 215:403-410 (1990)) using the above identified default parameters for protein and nucleic acid comparison, respectively.

In the context of the present specification, the term major histocompatibility complex (MHC) is used in its meaning known in the art of cell biology and immunology; it refers to a cell surface molecule that displays a specific fraction (peptide), also referred to as an epitope, of a protein. There a two major classes of MHC molecules: class I and class II. Within the MHC class I two groups can be distinguished based on their polymorphism: a) the classical (MHC-Ia) with corresponding polymorphic HLA-A, HLA-B, and HLA-C genes, and b) the non-classical (MHC-Ib) with corresponding less polymorphic HLA-E, HLA-F, HLA-G and HLA-H genes.

MHC class I heavy chain molecules usually (i.e. when not in open conformer form) occur as an alpha chain linked to a unit of the non-MHC molecule β2-microglobulin. The alpha chain comprises, in direction from the N-terminus to the C-terminus, a signal peptide, three extracellular domains (α1-3, with α1 being at the N terminus), a transmembrane region and a C-terminal cytoplasmic tail. The peptide being displayed or presented is held by the peptide-binding groove, in the central region of the α1/α2 domains.

In the context of the present specification, the term β2-microglobulin domain is used in its meaning known in the art of cell biology and biochemistry; it refers to a non-MHC molecule that is part of the MHC class I heterodimer molecule. In other words, it constitutes the β chain of the MHC class I heterodimer.

In the context of the present specification, the term human leukocyte antigen (HLA) is used in its meaning known in the art of cell biology and biochemistry; it refers to gene loci encoding the human MHC class I proteins. The three major classical MHC-Ia genes are HLA-A, HLA-B and HLA-C, and all of these genes have a varying number of alleles (Table 1). Closely related alleles are combined in subgroups of a certain allele. For example the allele HLA-B57 has more than 100 closely related alleles that vary in one or more amino acids, according to the WHO Nomenclature Committee for Factors of the HLA System, labelled HLA-B*57: 01:01 to HLA-B*57:82. The full or partial sequence of all known HLA genes and their respective alleles are available to the person skilled in the art in specialist databases such as IMGT/HLA (http://www.ebi.ac.uk/ipd/imgt/hla/).

In the context of the present specification, the term antibody is used in its meaning known in the art of cell biology and immunology; it refers to whole antibodies including but not limited to immunoglobulin type G (IgG), type A (IgA), type D (IgD), type E (IgE) or type M (IgM), any antigen binding fragment or single chains thereof and related or derived constructs. A whole antibody is a glycoprotein comprising at least two heavy (H) chains and two light (L) chains inter-connected by disulfide bonds. Each heavy chain is comprised of a heavy chain variable region ($V_H$) and a heavy chain constant region ($C_H$). The heavy chain constant region is comprised of three domains, $C_H1$, $C_H2$ and $C_H3$. Each light chain is comprised of a light chain variable region (abbreviated herein as $V_L$) and a light chain constant region ($C_L$). The light chain constant region is comprised of one domain, $C_L$. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component of the classical complement system.

The term antibody-like molecule in the context of the present specification refers to a molecule capable of specific binding to another molecule or target with high affinity/a Kd≤10E-8 mol/l. An antibody-like molecule binds to its target similarly to the specific binding of an antibody. The term antibody-like molecule encompasses a repeat protein, such as a designed ankyrin repeat protein (Molecular Partners, Zurich), a polypeptide derived from armadillo repeat proteins, a polypeptide derived from leucine-rich repeat proteins and a polypeptide derived from tetratricopeptide repeat proteins.

The term antibody-like molecule further encompasses a polypeptide derived from protein A domains, a polypeptide derived from fibronectin domain FN3, a polypeptide derived from consensus fibronectin domains, a polypeptide derived from lipocalins, a polypeptide derived from Zinc fingers, a polypeptide derived from Src homology domain 2 (SH2), a polypeptide derived from Src homology domain 3 (SH3), a polypeptide derived from PDZ domains, a polypeptide derived from gamma-crystallin, a polypeptide derived from ubiquitin, a polypeptide derived from a cysteine knot polypeptide and a polypeptide derived from a knottin.

The term protein A domains derived polypeptide refers to a molecule that is a derivative of protein A and is capable of specifically binding the Fc region and the Fab region of immunoglobulins.

The term armadillo repeat protein refers to a polypeptide comprising at least one armadillo repeat, wherein an armadillo repeat is characterized by a pair of alpha helices that form a hairpin structure.

In the context of the present specification, the term crystallizable fragment (Fc) region is used in its meaning known in the art of cell biology and immunology; it refers to a fraction of an antibody comprising two identical heavy chain fragments comprised of a $C_H2$ and a $C_H3$ domain, covalently linked by disulfide bonds.

In the context of the present specification, the term dimer refers to a unit consisting of two subunits.

In the context of the present specification, the term homodimer refers to a dimer comprised of two subunits that are either identical or are highly similar members of the same class of subunits. One example for a homodimer would be a dimer consisting of two subunits independently selected from the list of HLA alleles. In certain embodiments, homodimers consist of two identical HLA alleles.

In the context of the present specification, the term amino acid linker refers to a polypeptide of variable length that is used to connect two polypeptides in order to generate a single chain polypeptide. Exemplary embodiments of linkers useful for practicing the invention specified herein are oligopeptide chains consisting of 1, 2, 3, 4, 5, 10, 20, 30, 40 or 50 amino acids. A non-limiting example of an amino acid linker is the polypeptide GGGGSGGGGS (SEQ ID No. 001) that links an HLA-heavy chain polypeptide with an Fc domain.

In the context of the present specification, the term checkpoint inhibitory agent or checkpoint inhibitory antibody is meant to encompass an agent, particularly a (non-agonist) antibody (or antibody-like molecule) capable of disrupting the signal cascade leading to T cell inhibition after T cell activation as part of what is known in the art the immune checkpoint mechanism. Non-limiting examples of a checkpoint inhibitory agent or checkpoint inhibitory antibody include antibodies to CTLA-4 (Uniprot P16410), PD-1 (Uniprot Q15116), PD-L1 (Uniprot Q9NZQ7), B7H3 (CD276; Uniprot Q5ZPR3), Tim-3, Gal9, VISTA, or Lag3.

In the context of the present specification, the term checkpoint agonist agent or checkpoint agonist antibody is meant to encompass an agent, particularly but not limited to an antibody (or antibody-like molecule) capable of engaging the signal cascade leading to T cell activation as part of what is known in the art the immune checkpoint mechanism. Non-limiting examples of receptors known to stimulate T cell activation include CD122 and CD137 (4-1 BB; Uniprot Q07011). The term checkpoint agonist agent or checkpoint agonist antibody encompasses agonist antibodies to CD137 (4-1BB), CD134 (OX40), CD357 (GITR), CD278 (ICOS), CD27, CD28.

In the context of the present specification, the term (immune) checkpoint modulatory agent encompasses checkpoint inhibitory agents, checkpoint inhibitory antibodies, checkpoint agonist agents and checkpoint agonist antibodies.

Specific Description of the Invention

The present invention provides MHC-Ia open conformers (HLA-open conformers). MHC-Ia open conformers comprise HLA-A, HLA-B and HLA-C open conformers. In table 1 a list of known MHC-Ia alleles is provided. The present invention does not include MHC-Ia open conformers that comprise a HLA-B27 or a HLA-B57 allele.

According to a first aspect of the invention an isolated MHC-Ia open conformer is provided, with the proviso that the isolated MHC-Ia open conformer is not a HLA-B27 or a HLA-B57 open conformer.

In certain embodiments, the isolated MHC-Ia open conformer comprises a first monomer or a first and a second monomer, and each monomer independently of the other monomer comprises a HLA heavy chain.

According to an alternative to the first aspect of the invention an isolated HLA-A open conformer is provided.

According to another alternative to the first aspect of the invention an isolated HLA-B open conformer is provided, with the proviso that the isolated HLA-B open conformer is not a HLA-B27 or a HLA-B57 open conformer.

According to yet another alternative to the first aspect of the invention an isolated HLA-C open conformer is provided.

According to yet another alternative to the first aspect of the invention an isolated HLA-A open conformer and a HLA-C open conformer is provided.

According to a second aspect of the invention an isolated MHC-Ia open conformer, with the proviso that the isolated MHC-Ia open conformer is not a HLA-B27 or a HLA-B57 open conformer, is provided:
for use as a medicament,
particularly for use in the treatment or prevention of cancer, or
particularly for use as an immunomodulatory agent,
particularly in a treatment of an infectious disease,
more particularly for use in prevention, treatment or therapy of human immunodeficiency virus (HIV), hepatitis A, B, C, virus (HAV HBV, HCV respectively), influenza virus, Respiratory Syncytial Virus (RSV), measles virus, herpes viruses and/or yellow fever virus.

According to an alternative to the second aspect of the invention an isolated HLA-A open conformer is provided:
for use as a medicament,
particularly for use in the treatment or prevention of cancer, or
particularly for use as an immunomodulatory agent,
particularly in a treatment of an infectious disease,
more particularly for use in prevention, treatment or therapy of human immunodeficiency virus (HIV), hepatitis A, B, C, virus (HAV HBV, HCV respectively), influenza virus, Respiratory Syncytial Virus (RSV), measles virus, herpes viruses and/or yellow fever virus.

According to another alternative to the second aspect of the invention an isolated HLA-B open conformer, with the proviso that the isolated HLA-B open conformer is not a HLA-B27 or a HLA-B57 open conformer is provided:
for use as a medicament,
particularly for use in the treatment or prevention of cancer, or
particularly for use as an immunomodulatory agent,
particularly in a treatment of an infectious disease,
more particularly for use in prevention, treatment or therapy of human immunodeficiency virus (HIV), hepatitis A, B, C, virus (HAV HBV, HCV respectively), influenza virus, Respiratory Syncytial Virus (RSV), measles virus, herpes viruses and/or yellow fever virus.

According to yet another alternative to the second aspect of the invention an isolated HLA-C open conformer is provided:
for use as a medicament,
particularly for use in the treatment or prevention of cancer, or
particularly for use as an immunomodulatory agent.
particularly in a treatment of an infectious disease,
more particularly for use in prevention, treatment or therapy of human immunodeficiency virus (HIV), hepatitis A, B, C, virus (HAV HBV, HCV respectively), influenza virus, Respiratory Syncytial Virus (RSV), measles virus, herpes viruses and/or yellow fever virus.

The function as an immunomodulatory agent is particularly useful to treat diseases requiring the modification of white blood cell responses, such as infectious diseases. Infectious diseases that can preferably be treated by the present invention include human immunodeficiency virus (HIV) infection, hepatitis A, hepatitis B, hepatitis C, influenza, respiratory syncytial virus (RSV) infection, measles, herpes and yellow fever.

In certain embodiments of the second aspect of the invention or of any above-mentioned alternative to the second aspect of the invention, the cancer is colon cancer or pancreatic cancer.

A third aspect of the invention relates to a fusion MHC-Ia open conformer, with the proviso that the fusion MHC-Ia open conformer is not a HLA-B27 or a HLA-B57 open conformer. The fusion MHC-Ia open conformer comprises, or essentially consists of, a first HLA heavy chain monomer or a first and a second HLA heavy chain monomer. Each of these HLA heavy chain monomer independently of the other comprises or essentially consists of a HLA heavy chain. The fusion MHC open conformer additionally comprises an Fc polypeptide sequence. In certain embodiments, the HLA monomer sequence is situated at the N terminus of the fusion MHC open conformer, and the Fc construct is located towards the C terminus. In certain embodiments, an amino acid linker joins the HLA-heavy chain and the Fc fragment.

The fusion MHC-Ia open conformer additionally comprises a polypeptide domain known to metabolically stabilize a polypeptide in vivo. One example of such a stabilizing domain is an Fc (crystallisable fragment) domain of an immunoglobulin, particularly the Fc polypeptide domain of a gamma immunoglobulin. The HLA-heavy chain and the stabilizing domain may optionally be joined by an amino acid linker. An open conformer fusion protein comprising the HLA chain and an immunoglobulin Fc fragment is henceforth termed HLA-Fc open conformer or $HLA_2$-Fc herein.

The presence of the Fc domain in the fusion protein facilitates increasing the solubility, stability, avidity, half-life, and from a technological point of view, cost-effective production and purification in mammalian systems (protein A or G purification).

According to an alternative to the third aspect of the invention a HLA-A open conformer is provided, wherein the HLA-A open conformer comprises a first monomer or a first and a second monomer, and each monomer independently of the other monomer comprises a HLA heavy chain additionally comprising an Fc polypeptide sequence and optionally, an amino acid linker joining the HLA-heavy chain and the Fc fragment.

According to another alternative to the third aspect of the invention a HLA-B open conformer, with the proviso that the HLA-B open conformer is not a HLA-B27 or a HLA-B57 open conformer is provided, wherein the HLA-B open conformer comprises a first monomer or a first and a second monomer, and each monomer independently of the other monomer comprises a HLA heavy chain additionally comprising an Fc polypeptide sequence and optionally, an amino acid linker joining the HLA-heavy chain and the Fc fragment.

According to yet another alternative to the third aspect of the invention a HLA-C open conformer is provided, wherein the HLA-C open conformer comprises a first monomer or a first and a second monomer, and each monomer independently of the other monomer comprises a HLA heavy chain additionally comprising an Fc polypeptide sequence and optionally, an amino acid linker joining the HLA-heavy chain and the Fc fragment.

According to an alternative aspect of the invention a MHC-Ia open conformer monomer (i.e., the HLA-heavy chain unattached to a second HLA-heavy chain polypeptide, and not bound by β2-microglobulin) is provided for use in the treatment or prevention of cancer, or for use as an immunomodulatory agent, with the proviso that the MHC-Ia open conformer monomer is not a HLA-B27 or a HLA-B57 open monomer. In certain embodiments of this aspect, the MHC-Ia monomer additionally comprises a peptide epitope fragment.

This aspect can be summarized in the following items:
Item 1: An isolated single HLA-heavy chain polypeptide monomer derived from MHC-Ia alleles essentially free of associated β2-microglobulin for use as a medicament, particularly for use in the treatment or prevention of cancer, or for use as an immunomodulatory agent.

Item 2: An isolated single HLA-heavy chain polypeptide monomer derived from the MHC-Ia alleles for use in the treatment or prevention of cancer or as an immunomodulatory agent according to item 1, wherein the monomer additionally comprises a peptide epitope fragment.

Item 3: An isolated single HLA-heavy chain polypeptide monomer derived from the MHC-Ia alleles for use in the treatment or prevention of cancer or as an immunomodulatory agent according to items 1 or 2, wherein the HLA-heavy chain only consists of the HLA-alpha 1, 2 and 3 domains.

Item 4: An isolated single HLA-heavy chain polypeptide monomer derived from the MHC-Ia alleles for use in the treatment or prevention of cancer or as an immunomodulatory agent according to any one of the preceding items, wherein the HLA-heavy chain comprises the transmembrane domain and does not comprise the intracellular domain (cytoplasmic tail).

Item 5: A combination medicament comprising
  a. an isolated single HLA-heavy chain polypeptide monomer derived from the MHC-Ia alleles as specified in any one of items 1 to 4, and
  b. a checkpoint inhibitory agent, particularly a checkpoint inhibitory antibody, and/or a checkpoint agonist agent, particularly a checkpoint agonist antibody.

Item 6: The combination medicament according to item 5, wherein said checkpoint inhibitory agent is selected from an inhibitor of CTLA4 interaction with CD80 or CD86, and an inhibitor of the interaction of PD-1 with its ligand PD-L1, particularly an antibody against any one of CTLA4, CD80, CD86, PD-1, PD-L1, more particularly a monoclonal antibody against human CTLA4, PD-1, or PD-L1, and/or wherein said checkpoint agonist agent is selected from an agonist antibody or ligand to 4-1BB and/or 4-1BBL (CD137L, Uniprot P41273).

In certain embodiments of this alternative aspect of the invention, the cancer is colon cancer or pancreatic cancer.

According to another aspect of the invention a MHC-Ia open conformer protein is provided as an immunomodulatory agent, with the proviso that the MHC-Ia open conformer is not a HLA-B27 or a HLA-B57 open conformer. Without wishing to be bound by theory the inventors believe that particularly its capacity to bind to diverse immunoregulatory receptors present in white blood cells and to modify the proliferation of T cell lymphoma cells is particularly useful. Furthermore the use of MHC-Ia open conformers as negative modulator of regulatory T cells (Tregs) is particularly suitable, for use in human diseases where Tregs impair the development of protective immunity, such as cancer and infectious diseases (von Boehmer et al. ibid.).

According to an alternative to this other aspect of the invention a HLA-A open conformer is provided as an immunomodulatory agent.

According to another alternative to this other aspect of the invention a HLA-B open conformer is provided as an immunomodulatory agent, with the proviso that the HLA-B open conformer is not a HLA-B27 or a HLA-B57 open conformer.

According to yet another alternative to this other aspect of the invention a HLA-C open conformer is provided as an immunomodulatory agent.

In certain embodiments of any one of the aspects of the invention, the HLA-heavy chain comprises the transmembrane domain and does not comprise the intracellular domain (cytoplasmic tail).

In certain embodiments of any one of the aspects of the invention, the isolated MHC-Ia open conformer or fusion MHC-Ia open conformer consists of two subunits independently selected from the above HLA-alleles. In certain embodiments, homodimers consist of two identical HLA-alleles.

In certain embodiments of any one of the aspects of the invention, the isolated MHC-Ia open conformer or fusion MHC-Ia open conformer comprise two identical HLA polypeptide chains.

In certain embodiments, the isolated MHC-Ia open conformer or fusion MHC-Ia open conformer comprises two different HLA polypeptide chains.

In certain embodiments of any one of the aspects of the invention, the isolated MHC-Ia open conformer or fusion MHC-Ia open conformer additionally comprises a peptide epitope fragment.

In certain embodiments of any one of the aspects of the invention, a peptide epitope fragment is non-covalently attached to the polypeptide within the antigen presenting domain of the HLA peptide chain.

In certain embodiments of any one of the aspects of the invention, the first and/or second monomer additionally comprises a peptide epitope fragment.

In certain embodiments of any one of the aspects of the invention, the fusion MHC-Ia open conformer comprises only the extracellular HLA-alpha 1, HLA-alpha 2 and HLA-alpha 3 domains. In these embodiments, the transmembrane and intracellular domains of the HLA heavy chains are not included in the therapeutic polypeptide of the invention in order to allow its extracellular expression in recombinant cells. The person skilled in the art can easily identify the respective domains even in previously unknown HLA-sequences by pair-wise sequence alignment with annotated HLA-sequences.

In certain embodiments of any one of the aspects of the invention, the fusion MHC-Ia open conformers comprise an Fc domain. In certain particular embodiments, the Fc domain comprises heavy chain constant regions $C_H2$ and $C_H3$ from immunoglobulin type G (IgG), type A (IgA), type D (IgD), type E (IgE) or type M (IgM).

In certain embodiments of any one of the aspects of the invention, the fusion MHC-Ia open conformers comprise an amino acid linker joining a stabilizing domain, particularly an Fc domain, to the HLA polypeptide. In certain particular embodiments, the amino acid linker comprises 1 to 50 amino acids, particularly 5 to 40 amino acids, more particularly 10 to 30 amino acids, even more particularly 15 to 25 amino acids that link the HLA-heavy chain to the Fc domain as one single polypeptide chain.

In certain embodiments of any one of the aspects of the invention, the isolated MHC-Ia open conformers or fusion MHC-Ia open conformers, are provided as parenteral dosage form, particularly confectioned for injection. In certain embodiments, the immune checkpoint inhibitor agent or agonist agent is provided as parenteral dosage form, particularly confectioned for injection. In certain embodiments, both the MHC-Ia open conformers and the immune checkpoint inhibitor agent or agonist agent are present in the same administration form.

In certain embodiments of the third aspect of the invention, the fusion MHC-Ia open conformer is for use as a medicament.

In certain embodiments of the third aspect of the invention, the fusion MHC-Ia open conformer is for use in the treatment or prevention of cancer, in particular for colon cancer or pancreatic cancer.

In certain embodiments of the third aspect of the invention, the fusion MHC-Ia open conformer is for use as an immunomodulatory agent, particularly for use as negative modulator of regulatory T cells (Treg). In certain embodiments, the fusion MHC-Ia open conformer is for use in the treatment of infectious diseases. In certain embodiments, the fusion MHC-Ia open conformer is for use in the treatment of human immunodeficiency virus (HIV) infection, hepatitis A, hepatitis B, hepatitis C, influenza, respiratory syncytial virus (RSV) infection, measles, herpes and yellow fever.

According to a fourth aspect of the invention, a nucleic acid molecule encoding MHC-Ia open conformer monomers, particularly an Fc open conformer monomer, according to the above aspects of the invention is provided for use in the treatment or the therapy of cancer or for use as an immunomodulatory agent, particularly in a treatment of an infectious disease. Expression of the open conformer in vivo from the nucleic acid molecule will, after dimerization, lead to the fusion protein polypeptide of the invention. The concept of expressing pharmaceutically active polypeptides from nucleic acids encoding them in the patient's body is well known and may confer significant benefits to the patient.

According to an alternative to the fourth aspect of the invention a nucleic acid encoding HLA-A open conformers monomers for use in the treatment or the therapy of cancer or for use as an immunomodulatory agent, particularly in a treatment of an infectious disease is provided.

According to another alternative to the fourth aspect of the invention a nucleic acid encoding HLA-B open conformers monomers for use in the treatment or the therapy of cancer or for use as an immunomodulatory agent, particularly in a treatment of an infectious disease is provided, with the proviso that the HLA-B open conformer is not a HLA-B27 or a HLA-B57 open conformer.

According to yet another alternative to the fourth aspect of the invention a nucleic acid encoding HLA-C open conformers monomers for use in the treatment or the therapy of cancer or for use as an immunomodulatory agent, particularly in a treatment of an infectious disease is provided.

In certain embodiments of the fourth aspect of the invention or any above-mentioned alternative thereof, the cancer is colon cancer or pancreatic cancer.

In certain embodiments, the nucleic acid molecule encodes MHC-Ia open conformers monomers, particularly an Fc open conformer monomer comprising a peptide epitope fragment. In certain embodiments, the nucleic acid molecule encodes MHC-Ia open conformers monomers, particularly an Fc open conformer monomer that comprises only the extracellular HLA-alpha 1, 2 and 3 domains. In certain embodiments, the nucleic acid molecule encodes HLA open conformers monomers, particularly an Fc open conformer monomer that comprises only the extracellular HLA-alpha 1, 2 and 3 domains, and a peptide epitope fragment.

In certain embodiments, the nucleic acid molecule encodes MHC-Ia open conformers monomers, particularly an Fc open conformer monomer that comprises an amino acid linker and/or an Fc (fragment crystallizable) domain, and is used in the treatment or the therapy of cancer, in particular colon or pancreatic cancer.

According to an alternative aspect of the invention a recombinant expression vector comprising the nucleic acid molecule according to the fourth aspect of the invention (and its alternative aspects) is provided for use in the treatment or the therapy of cancer, in particular colon or pancreatic cancer.

In certain embodiments the recombinant expression vector is a plasmid comprising a promoter that is operable in a mammalian cell, particularly in a human cell. The promoter is operably linked to the nucleic acid molecule of the invention.

According to a fifth aspect of the invention a virus comprising the nucleic acid molecule according to the fourth aspect of the invention (and its alternative aspects) is provided for use in the treatment or the therapy of cancer, in particular colon or pancreatic cancer, or for use as an immunomodulatory agent, particularly in a treatment of an infectious disease. The nucleic acid molecule is under control of a promoter sequence operable in a mammalian cell, particularly in a human cell. In certain embodiments, the virus is an adenovirus, adeno-associated virus, a herpes virus or a lentivirus.

According to a sixth aspect of the invention an in vitro genetically modified host cell comprising the nucleic acid molecule according to the fourth aspect of the invention (and its alternative aspects) is provided.

Another aspect of the invention provides for the use of the isolated MHC-Ia open conformers homodimer or MHC-Ia open conformers homodimer according to the first and second aspect of the invention (and their alternatives) in the manufacture of a medicament for the treatment or prevention of cancer, in particular colon or pancreatic cancer.

According to yet another aspect, the invention provides a method of treatment for cancer, in particular colon or pancreatic cancer, comprising administering an MHC-Ia open conformer according to the first and second aspect of the invention (and their alternative aspects) to a patient in need thereof.

According to a seventh aspect of the invention, a combination medicament is provided, wherein the combination medicament comprises:
  isolated MHC-Ia open conformers or fusion MHC-Ia open conformers, according to any one of the above aspects or embodiments of the invention, and
  an immune checkpoint modulatory agent selected from
    an immune checkpoint inhibitor agent (CPI) selected from:
      an inhibitor of cytotoxic T-lymphocyte-associated protein 4 (CTLA4; also known as CD152) interaction with either B7-1 (CD80) and/or B7-2 (CD86), particularly a polypeptide ligand to CTLA-4 or to cd80 or to cd86 such as for example an antibody,
    an inhibitor of the interaction of programmed cell death protein 1 (PD-1; also known as CD279) with its ligand PD-L1 (also known as CD274; UniProt ID: Q9NZQ7) and/or PD-L2 (also known as CD273; Uni Prot ID: Q9BQ51), particularly a polypeptide ligand to PD-1 or to PD-L1 or to PD-L2 such as for example an antibody, and
    an inhibitory polypeptide ligand, particularly an antibody, of T cell immunoglobulin and mucin domain-containing 3 (TIM-3), and
  a checkpoint agonist agent, particularly a checkpoint agonist antibody selected to bind to and activate the tumor necrosis factor receptor 4-1 BB (also known as CD137 or TNFRSF9).

According to an alternative to the seventh aspect of the invention the isolated MHC-Ia open conformer or fusion MHC-Ia open conformer comprised within the combination medicament is selected from a HLA-A open conformer, a HLA-B open conformer (with the proviso that the HLA-B open conformer is not a HLA-B27 or a HLA-B57 open conformer) or a HLA-C open conformer.

In certain embodiments, the immune checkpoint inhibitor agent is an inhibitor of interaction of CTLA4 with CD80 or CD86.

In certain embodiments, the immune checkpoint inhibitor agent is ipilimumab (Yervoy; CAS No. 477202-00-9).

In certain embodiments, the immune checkpoint inhibitor agent is an inhibitor of interaction of programmed cell death protein 1 (PD-1) with its receptor PD-L1. In certain embodiments, the immune checkpoint inhibitor agent is selected from the clinically available antibody drugs nivolumab (Bristol-Myers Squibb; CAS No 946414-94-4), pembrolizumab (Merck Inc.; CAS No. 1374853-91-4), pidilizumab (CAS No. 1036730-42-3), atezolizumab (Roche AG; CAS No. 1380723-44-3), and Avelumab (Merck KGaA; CAS No. 1537032-82-8).

In certain embodiments, the immune checkpoint agonist agent is utomilumab (PF-05082566), a fully human IgG2 monoclonal antibody against 4-1BB currently undergoing clinical trials.

In certain embodiments, the checkpoint modulatory agent is a polypeptide selected from an antibody, an antibody fragment, and an antibody-like molecule, and the polypeptide is selectively reactive to a checkpoint mediator. In certain embodiments, the checkpoint mediator is selected from CTLA4, PD-1, CD80, CD86, PD-L1, and PD-L2, TIM-3, 4-1 BB and 4-1BBL.

In yet another aspect, the invention relates to a method for producing recombinant HLA heavy chain polypeptides. This method is summarized in the following items:

Item A: A method for producing, by methods of recombinant biotechnology, a human HLA heavy chain polypeptide, wherein said method comprises the following steps:
  a. Expression step:
    i. a HLA-encoding nucleic acid sequence encoding at least the alpha 1 chain, the alpha 2 chain and the alpha 3 chain of a HLA heavy chain under control of a promoter sequence operable in a cell, particularly a eukaryotic cell, more particularly a mammalian cell, and
    ii. a β2-microglobulin encoding nucleic acid sequence encoding the human HLA beta 2 microglobulin (UniProt P61769) under control of a promoter sequence operable in said cell (the same cell as in item 1. a.) are co-expressed in a mammalian cell ("production cell line");

b. Purification step: the resulting HLA-heavy-chain /β2-microglobulin complex is purified from the mammalian cell (the production cell line);
c. Dissociation step: the purified HLA-heavy-chain /β2-microglobulin complex is dissociated under suitable conditions and the HLA heavy chain polypeptides are separated from the β2-microglobulin polypeptides;
d. Refolding step: the separated HLA heavy chain polypeptides are incubated under conditions leading to refolding (of their native tertiary protein structure found in physiologically active HLA open conformer molecules).

Item AA: Item A with the proviso that the human HLA heavy chain polypeptide is neither a B27 heavy chain nor a B57 heavy chain.

Item B: The method for producing a human HLA heavy chain polypeptide according to item A or item AA, wherein the HLA-encoding nucleic acid sequence comprises, from N to C terminus of the encoded polypeptide, the alpha 1 chain, the alpha 2 chain, the alpha 3 chain and a stabilizing sequence.

Item C: The method for producing a human HLA heavy chain polypeptide according to item B, wherein the stabilizing sequence is selected from bovine serum albumin and an immunoglobulin constant fragment (Fc), particularly an immunoglobulin G constant fragment, more particularly an IgG4 Fc.

Item D: The method for producing a human HLA heavy chain polypeptide according to any of the preceding items, wherein the HLA-encoding nucleic acid sequence and the β2-microglobulin encoding nucleic acid sequence are present on the same nucleic acid vector molecule (particularly, a DNA expression plasmid).

Item E: The method for producing a human HLA heavy chain polypeptide according to any of the preceding items A to C, wherein the HLA-encoding nucleic acid sequence and the β2-microglobulin encoding nucleic acid sequence are present on different nucleic acid vector molecules (particularly, different DNA expression plasmids).

Item F: The method of item E, wherein the nucleic acid vector comprising the HLA-encoding nucleic acid sequence is present in approximately 1- to 5-fold excess, particularly 1.5 to 5-fold excess with respect to the nucleic acid vector comprising the β2-microglobulin encoding nucleic acid sequence, particularly in approximately 3-fold excess.

Item G: The method of any of the preceding items, wherein the HLA-encoding nucleic acid sequence comprises an immunoglobulin Fc fragment as a stabilizing sequence and the purification step is effected by adsorbing the recombinant HLA heavy chain polypeptides to a surface linked to protein A.

Item H: The method of any of the preceding items, wherein the dissociation step is effected by treatment under acidic conditions, particularly at approximately pH 2, and dialysis under reductive conditions.

Item I: The method of any of the preceding items, wherein the refolding step is effected by treatment under neutral conditions.

More specifically pointed at the MHC-Ia open conformers specified herein, the method can be summarized in the following items:

Item A': A method for producing, by methods of recombinant biotechnology, a human HLA-heavy chain polypeptide, wherein said method comprises the following steps:
a. Expression step:
  i. a HLA heavy chain-encoding nucleic acid sequence encoding at least the alpha 1 chain, the alpha 2 chain and the alpha 3 chain of a HLA heavy chain under control of a promoter sequence operable in a cell, particularly a eukaryotic cell, more particularly a mammalian cell, and
  ii. a β2-microglobulin encoding nucleic acid sequence encoding the human HLA beta 2 microglobulin (UniProt P61769) under control of a promoter sequence operable in said cell (the same cell as in item 1. a.) are co-expressed in a mammalian cell ("production cell line");
b. Purification step: the resulting HLA-heavy-chain /β2-microglobulin complex is purified from the mammalian cell (the production cell line);
c. Dissociation step: the purified HLA-heavy-chain /β2-microglobulin complex is dissociated under suitable conditions and the HLA heavy chain polypeptides are separated from the β2-microglobulin polypeptides;
d. Refolding step: the separated HLA-heavy chain polypeptides are incubated under conditions leading to refolding (of their native tertiary protein structure found in physiologically active HLA open conformer molecules).

Item AA': Item A' with the proviso that the human HLA heavy chain polypeptide is neither a B27 heavy chain nor a B57 heavy chain.

Item B': The method for producing a human HLA-heavy chain polypeptide according to item A' or item AA', wherein the HLA-encoding nucleic acid sequence comprises, from N to C terminus of the encoded polypeptide, the alpha 1 chain, the alpha 2 chain, the alpha 3 chain and a stabilizing sequence.

Item C': The method for producing a human HLA-heavy chain polypeptide according to item B', wherein the stabilizing sequence is selected from bovine serum albumin and an immunoglobulin constant fragment (Fc), particularly an immunoglobulin G constant fragment, more particularly an IgG4 Fc.

Item D': The method for producing a human HLA-heavy chain polypeptide according to any of the preceding items, wherein the HLA-encoding nucleic acid sequence and the β2-microglobulin encoding nucleic acid sequence are present on the same nucleic acid vector molecule (particularly, a DNA expression plasmid).

Item E': The method for producing a human HLA-heavy chain polypeptide according to any of the preceding items A' to C', wherein the HLA-encoding nucleic acid sequence and the β2-microglobulin encoding nucleic acid sequence are present on different nucleic acid vector molecules (particularly, different DNA expression plasmids).

Item F': The method of item E', wherein the nucleic acid vector comprising the HLA-encoding nucleic acid sequence is present in approximately 1- to 5-fold excess, particularly 1.5 to 5-fold excess with respect to the nucleic acid vector comprising the 82-microglobulin encoding nucleic acid sequence, particularly in approximately 3-fold excess.

Item G': The method of any of the preceding items, wherein the HLA encoding nucleic acid sequence comprises an immunoglobulin Fc fragment as a stabilizing sequence and the purification step is effected by adsorbing the recombinant HLA heavy chain polypeptides to a surface linked to protein A.

Item H': The method of any of the preceding items, wherein the dissociation step is effected by treatment under acidic conditions, particularly at approximately pH 2, and dialysis under reductive conditions.

Item I': The method of any of the preceding items, wherein the refolding step is effected by treatment under neutral conditions.

Wherever alternatives for single separable features such as, for example, an allele or coding sequence are laid out herein as "embodiments", it is to be understood that such alternatives may be combined freely to form discrete embodiments of the invention disclosed herein.

The invention is further illustrated by the following examples and figures, from which further embodiments and advantages can be drawn. These examples are meant to illustrate the invention but not to limit its scope.

Examples

The inventors surprisingly found that MHC-Ia open conformers interact with diverse immunoregulatory cell surface receptors present in NK cells, NKT cells, T cells, macrophages and MDSC cells with unique binding or stronger affinity than their control MHC-Ia heterotrimers. HLA class I-a open conformers can be used as a therapeutics to target diseases were white blood cells impair the development of protective immunity, as is the case of cancer and infectious diseases.

Additionally, they discovered a novel in vivo mode of action with injections of $HLA_2$-Fc as monotherapy or combinatorial approaches using checkpoint modulatory agents. $HLA_2$-Fc therapy alone or in combinatorial therapies can modulate the infiltration of diverse sets of leukocytes into tumors as determined by the increased infiltration of macrophages M1/M2 ratio, increased NK cells, NKT cells, CD3+ T cells, and CD8+ T cells, and reduction of MDSCs.

Furthermore, they observed that systemically by blood analysis $HLA_2$-Fc therapy increase the expansion of NKT cells and in some cases Th1 cells, indicating the presence of a biomarker that can be used for therapy efficacy in preclinical and clinical settings. Interestingly, they also observed that monotherapy with 4-1 BB increases systemically the expansion of CD3+, CD4+, CD8+ T cells and Tregs in the blood of animals, indicating a potential side effect of hyper activation of the immune system by 4-1 BB. Diverse combinations of $HLA_2$-Fc+4-1 BB reduced significantly the presence of blood CD3+, CD4+, Treg, and CD8+ T cells, indicating a positive combinatorial approach in case of unwanted lymphocyte expansion on the blood of treated patients with agonistic antibodies.

Overall, the mode of action of MHC-Ia open conformers, particularly when present as fusion proteins comprising an Fc immunoglobulin fragment, alone or in a combinatorial approach with antagonistic/agonistic antibodies is of undoubted relevance as immunomodulatory agents, and can be useful for its translation in the treatment of cancer.

HLA open conformers can be used as a therapeutic to target diseases where immunomodulation is a therapeutic approach, as is the case of cancer and infectious diseases.

In Vitro Tests

Figure 5:
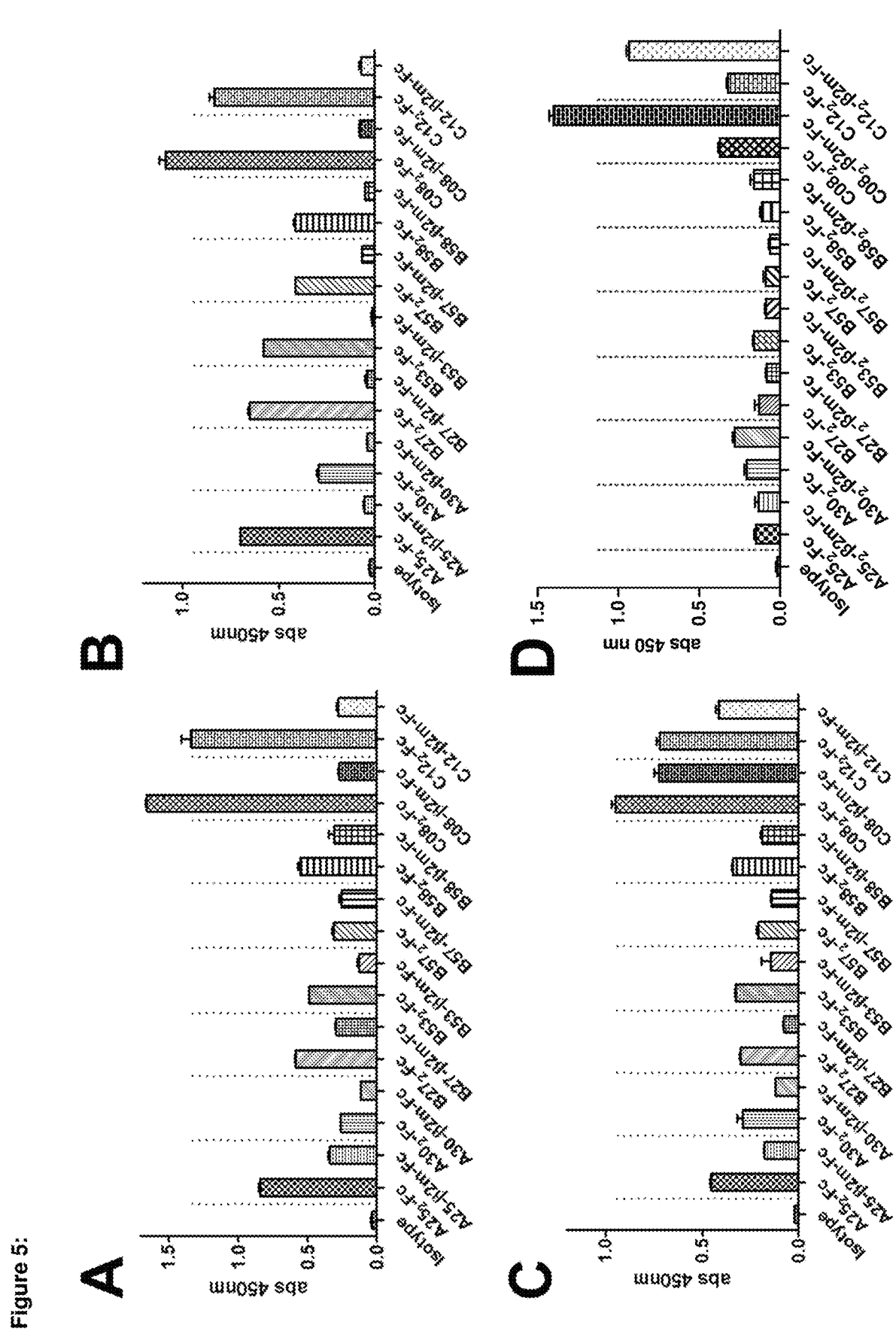
FIG. 5 shows the interaction $HLA_2$-Fc ($A25_2$-Fc, $A30_2$-Fc, $B27_2$-Fc, $B53_2$-Fc, $B57_2$-Fc, $B58_2$-Fc, $C08_2$-Fc and $C12_2$-Fc) to different immune regulatory receptors of leukocytes populations by enzyme-linked immunosorbent assay (ELISA). A) hu $KIR3DL1$, B) hu $KIR3DL2$, and C) hu KIR3DL3 are expressed in NK cells and subpopulations of T cells. D) LILRB1, and E) LILRB2 expressed mostly in myeloid cells, F) PirB (murine homologue to LILRB) and G) PTPRJ (on leukocytes is preferentially expressed in MDSCs cells and activated T cells)
Figure 5:
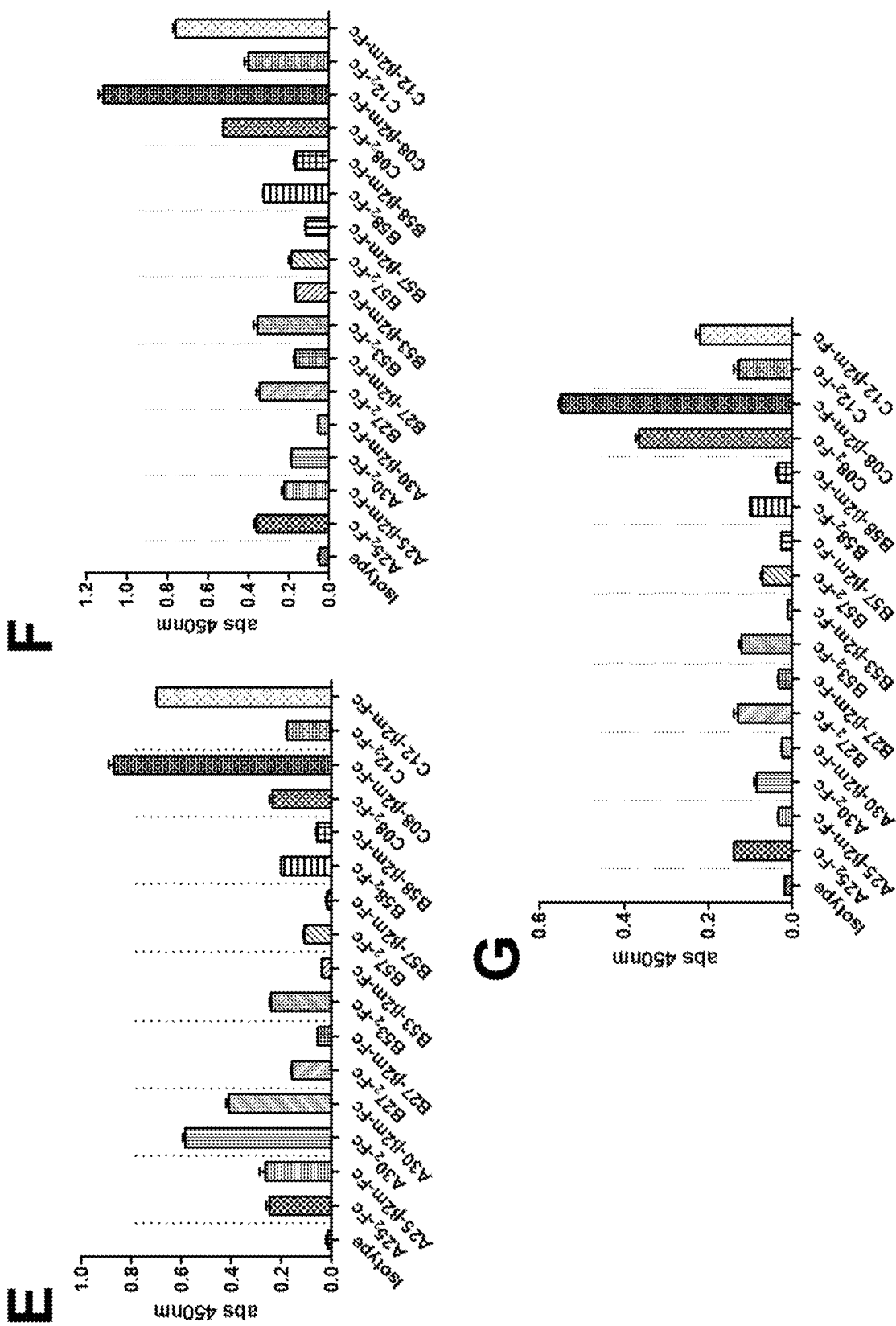

MHC-Ia open conformers bind to immunoregulatory receptors expressed in diverse types of white blood cells with unique binding or different affinity than their HLA-β2m-Fc control counterparts The inventors determined if MHC-Ia open conformers interact with specific immunomodulatory receptors by enzyme-linked immunosorbent assay (ELISA). Results demonstrated that MHC-Ia open conformers interact uniquely to KIR3DL2, and PTPRJ (for exception of HLA-C-β2m-Fc) and display different affinities to KIR3DL1, KIR3DL3, LILRB1, LILRB2, and Pirb immunoregulatory receptors than their HLA-β2m-Fc control counterparts (FIG. 5 A-G). This data shows for the first time that MHC classical alleles (HLA-A, HLA-B & HLA-C) (MHC-Ia) have a similar binding pattern to immunoregulatory receptors when they are present as open conformers.

MHC-Ia Open Conformers Blocks Conversion of Murine $CD4^+$ T Cells into iTregs

Figure 6:
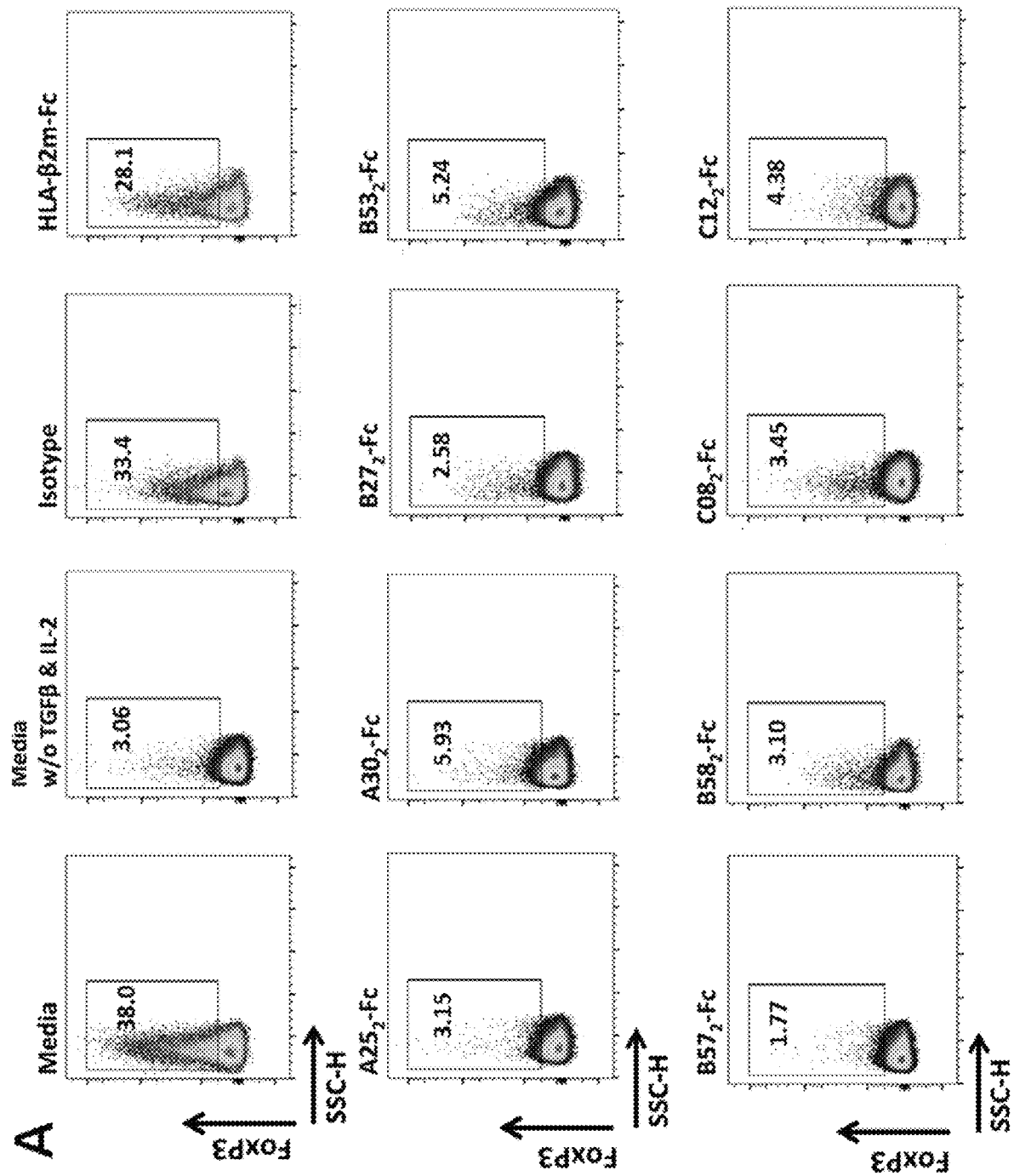
FIG. 6 shows that $HLA_2$-Fc molecules ($A25_2$-Fc, $A30_2$-Fc, $B27_2$-Fc, $B53_2$-Fc, $B57_2$-Fc, $B58_2$-Fc, $C08_2$-Fc, and $C12_2$-Fc) invariably block mouse CD4+ T cell conversion into iTreg. Incubation of $HLA_2$-Fc in a dose dependent manner with naïve CD4+ T cells blocks the conversion to iTregs. A-B) $HLA_2$-Fc molecules blocks the expression of FoxP3 (differentiation marker of Tregs) in optimal culture conditions for iTreg differentiation (10 µg/mL) Control HLA-β2m-Fc molecules, isotype, media supplemented with TGFβ and IL-2 and media w/o supplementation demonstrate the specific influence of $HLA_2$-Fc on iTreg conversion.
Figure 6:
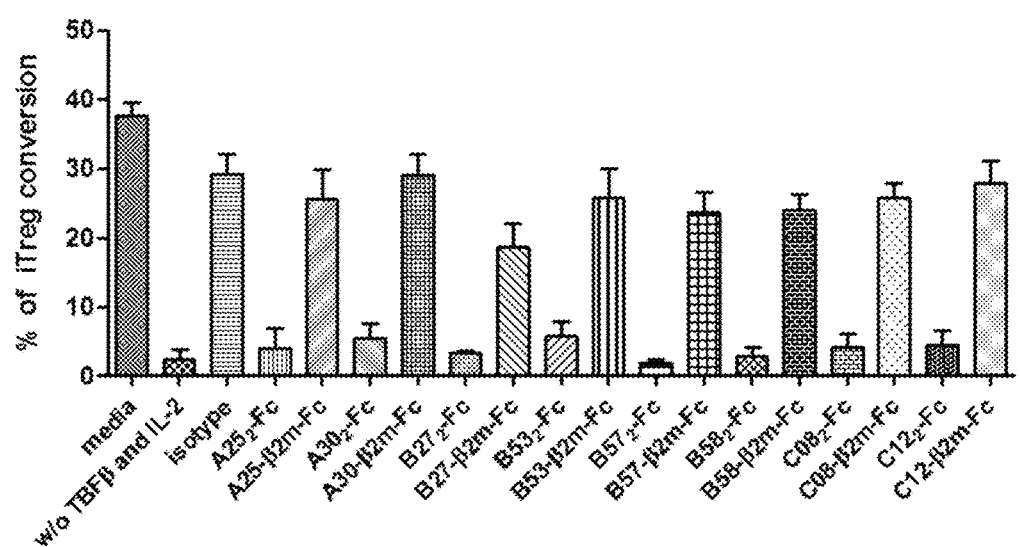

The influence of MHC-Ia molecules on naïve $CD4^+$ T cells for iTreg conversion was analysed with 10 μg/mL of $HLA_2$-Fc ($A25_2$-Fc, $A30_2$-Fc, $B272$-Fc, $B53_2$-Fc, $B57_2$-Fc, $B58_2$-Fc, $C08_2$-Fc and $C12_2$-Fc), HLA-β2m controls (A25-β2m-Fc, A30-β2m-Fc, B27-β2m-Fc, B53-β2m-Fc, B57-β2m-Fc, B58-β2m-Fc, C08-β2m-Fc and C12-β2m-Fc), isotype, and PBS, incubated with naïve $CD4^+$ T cells in optimal culture conditions for iTreg conversion. MHC-Ia open conformers demonstrated invariably to down modulate the induction of FoxP3 (FIG. 6) and thus conversion of naïve CD4+ T cells into iTregs.

MHC-Ia Open Conformers Impair the Proliferation of Leukaemia T Cells.

Figure 7:
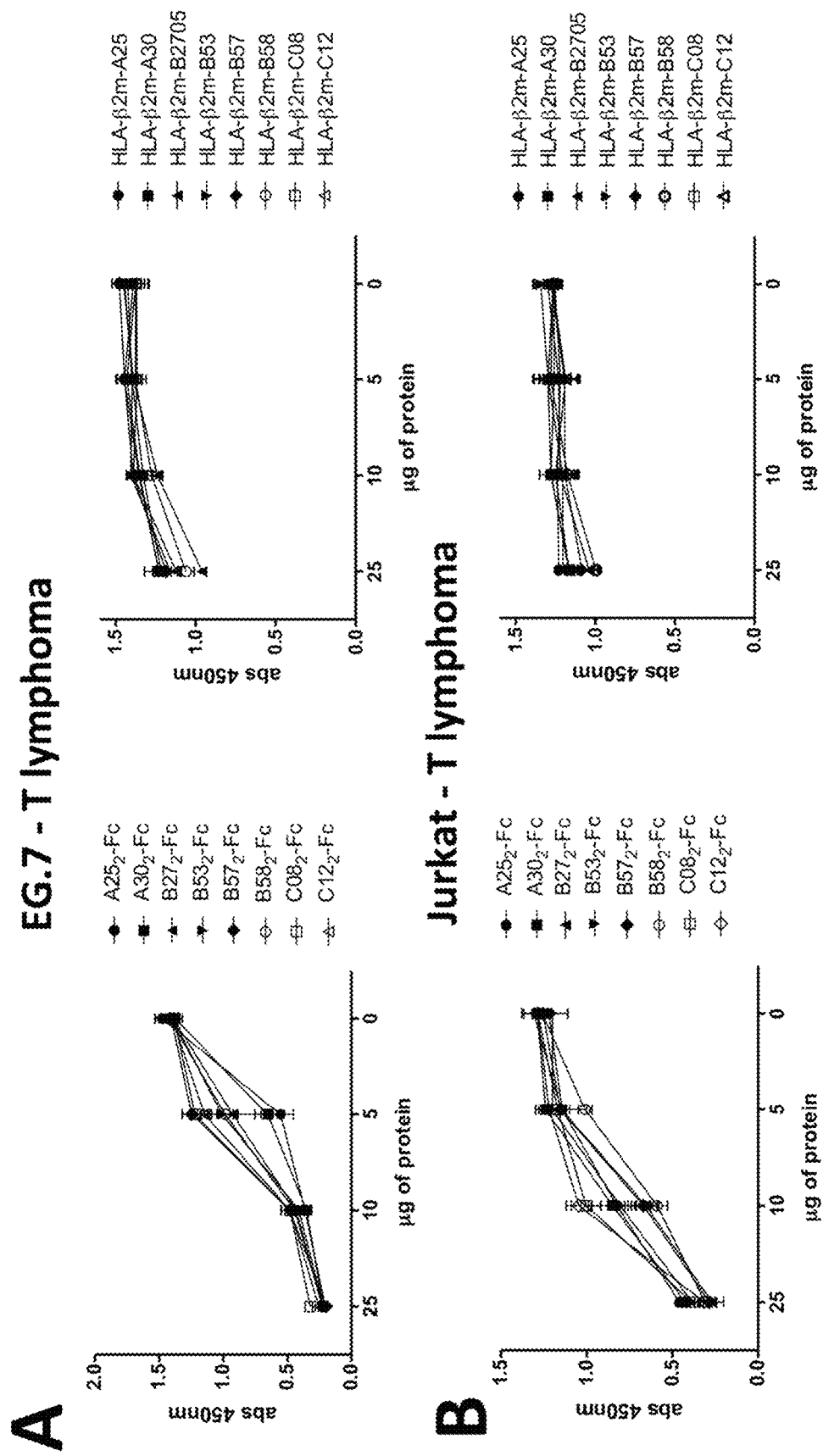
FIG. 7 shows that $HLA_2$-Fc ($A25_2$-Fc, $A30_2$-Fc, $B27_2$-Fc, $B53_2$-Fc, $B57_2$-Fc, $B58_2$-Fc, $C08_2$-Fc and $C12_2$-Fc) suppresses lymphoma T cells. A-E) suppression assays to determine the proliferation of cells in the presence of $HLA_2$-Fc molecules or control HLA-β2m-Fc molecules. $HLA_2$-Fc suppress human (Jurkat) and mouse (EG.7) lymphoma cell lines in a dose dependent manner (µg/200 µL), other cell lines such as Daudi, B cell lymphoma; SK-N-AS, neuroblastoma; and L540, human Hodgkin lymphoma were assessed but not suppression was observed from $HLA_2$-Fc molecules in optimal culture conditions. Other cell lines such as L428, human Hodgkin lymphoma; L1236, human Hodgkin lymphoma; IMR-5, neuroblastoma; and M130428, Melanoma were also tested but no suppression was observed.
Figure 7:
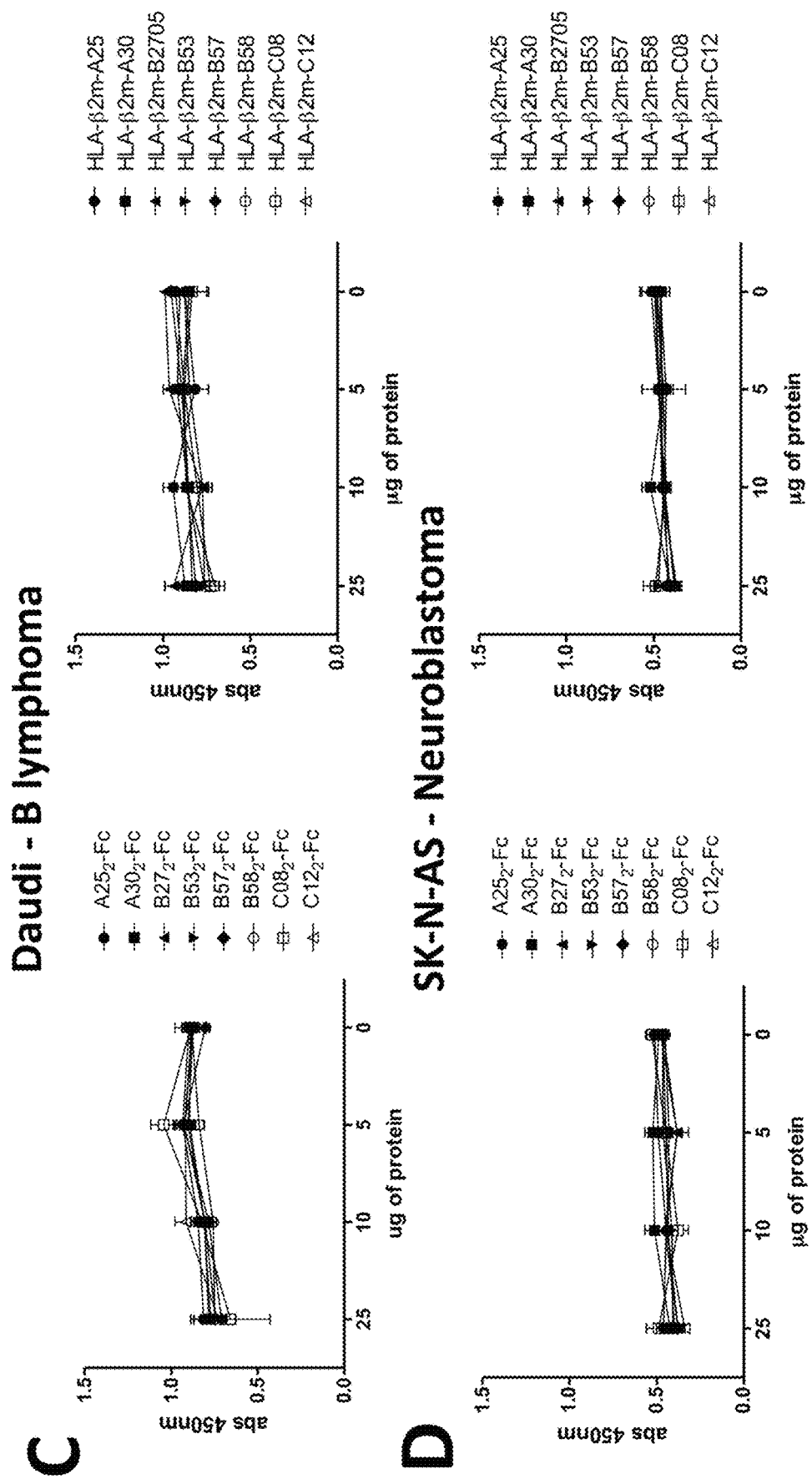
Figure 7:

The inventors determined the effect of MHC-Ia open conformers ($A25_2$-Fc, $A30_2$-Fc, $B272$-Fc, $B53_2$-Fc, $B57_2$-Fc, $B58_2$-Fc, $C08_2$-Fc and $C12_2$-Fc) with the blocking of proliferation in different tumor cell lines. Results demonstrated that MHC-Ia open conformers modulate invariably the proliferation of lymphoma T cell lines, when compared to their control counterparts HLA-β2m-Fc (FIG. 7) or isotype IgG4 (data not provided), indicating its potential application to the treatment of lymphoma as a targeted therapy.

In Vivo Tests

Figure 8:
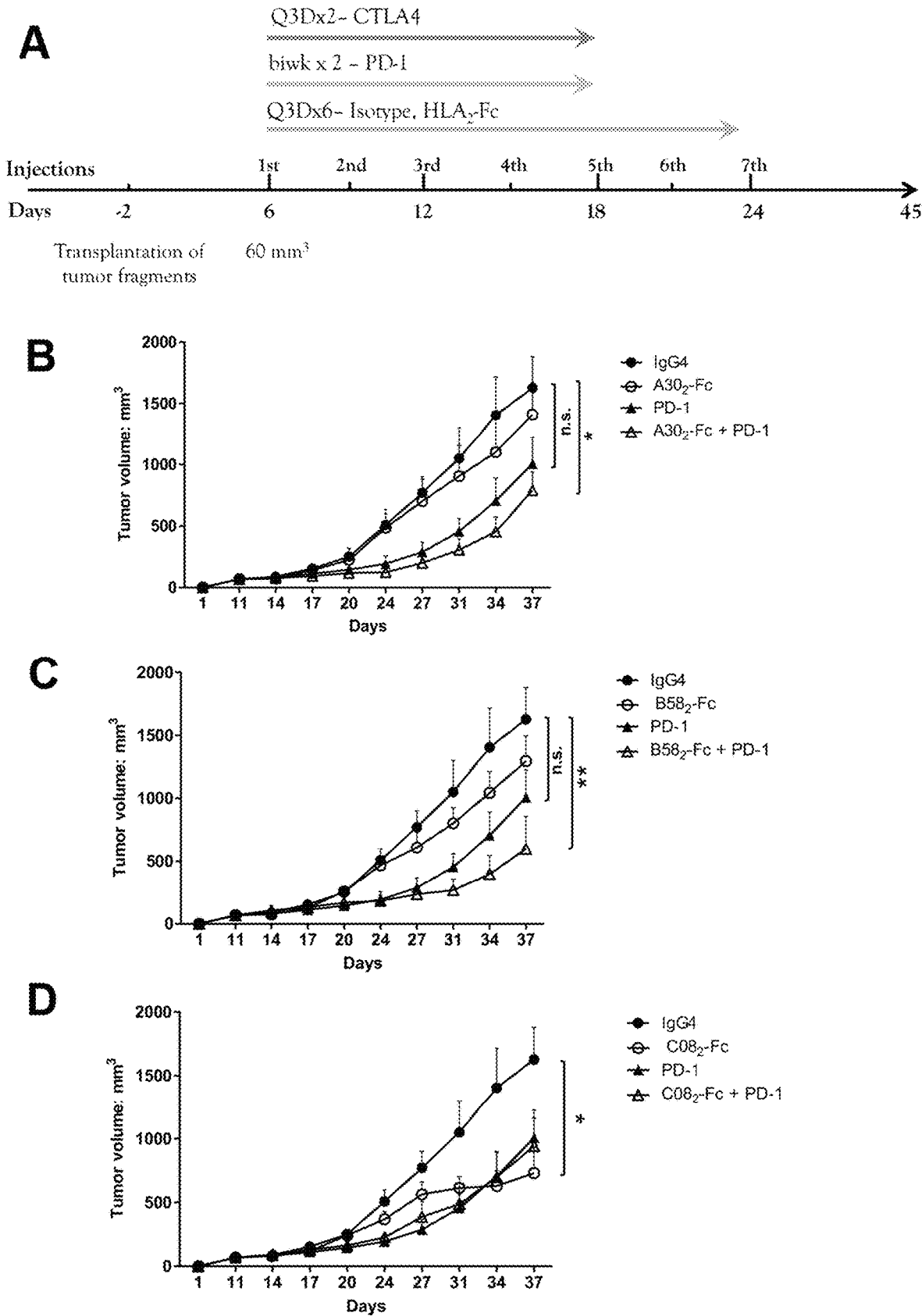
FIG. 8 shows that $HLA_2$-Fc ($A30_2$-Fc, $B58_2$-Fc, and $C08_2$-Fc) as monotherapy or in combination with PD-1 antibodies can reduce the size of tumors in the C38 murine syngeneic colon carcinoma model. A) Experimental design of injection time points of colon carcinoma cells (C38) and injection of compounds. B) Mean average tumor volume $mm^3$ of $A30_2$-Fc treated groups (n=5). C) Mean average tumor volume $mm^3$ of $B58_2$-Fc treated groups (n=5). D) Mean average tumor volume $mm^3$ of $C08_2$-Fc treated groups (n=5). The experimental design of injection time points of cells and injection of substances was as follow: vehicle PBS Q3Dx6, isotype (10 mg/Kg) Q3Dx6; $HLA_2$-Fc (10 mg/Kg) Q3Dx6; PD-1 biwk×2 (200 µg); and $HLA_2$-Fc+PD-1 (Q3Dx6 & biwk×2, respectively). Tumor volumes are expressed as mean±SEM and analysed by two-way ANOVA followed by Bonferroni post-hoc analysis, *p<0.05, **p<0.01, n.s.=not significant. Q=days between injections; Dx=number of injections; biwk=twice a week.

The in vivo proof of concept of MHC-Ia open conformers as immunomodulatory therapeutic molecules for cancer therapy was demonstrated using a validated pre-clinical syngeneic murine C38 and MC38-OVA colon carcinoma models (FIGS. 8 and 9), and in the pancreatic (Pan02) cancer mouse model (FIGS. 10, 13, 16, 19, 22, 25, 28 and 31).

Production of MHC-Ia Open Conformers as a Human Fc Fusion Protein in CHO Cells

Figure 1:
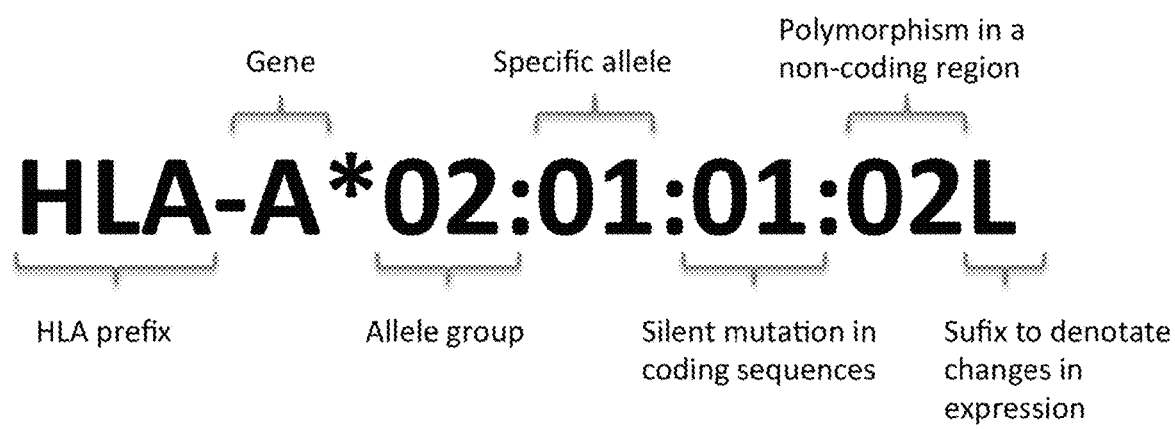
FIG. 1 shows the nomenclature of MHC class I molecules.
Figure 2:
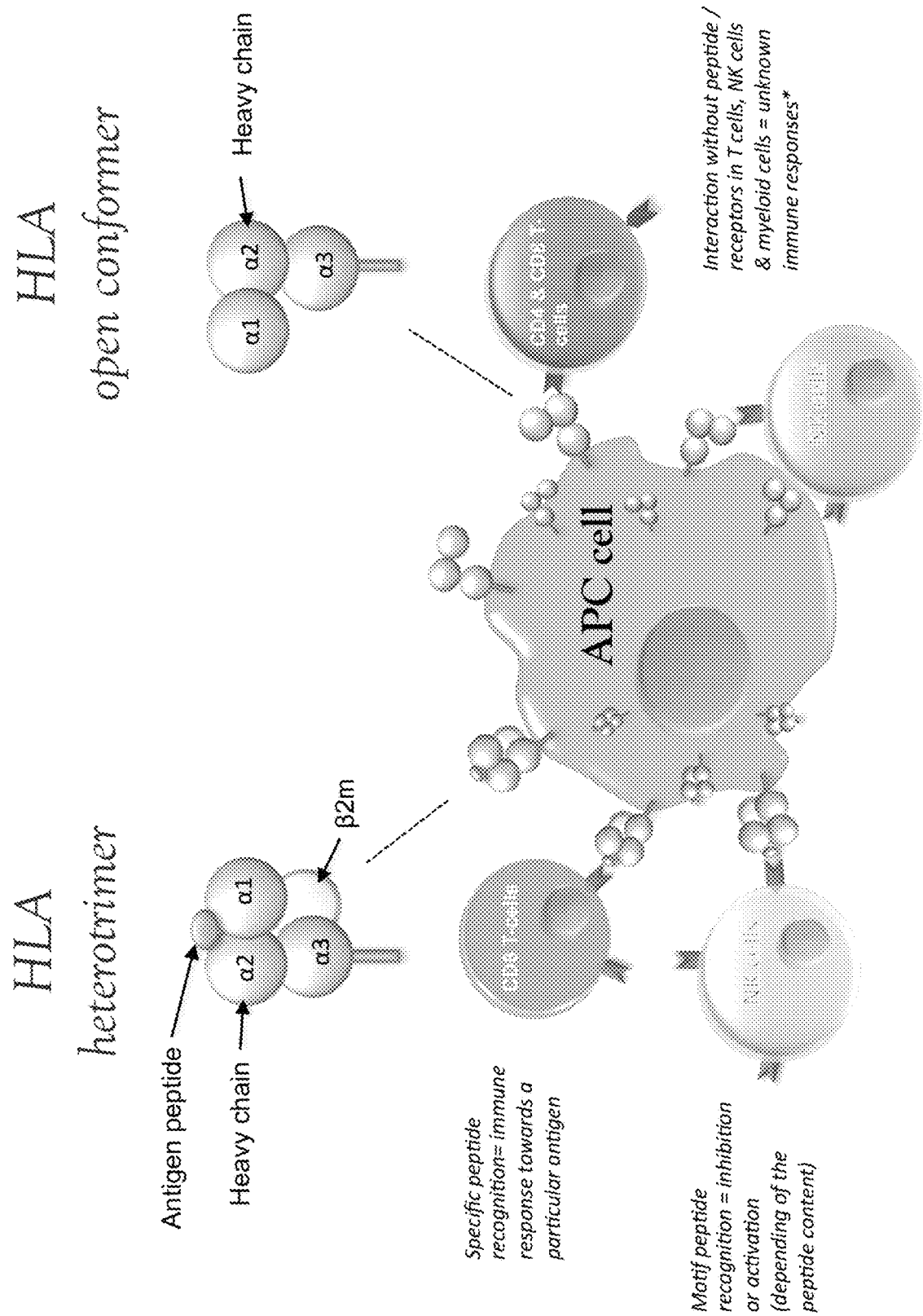
FIG. 2 shows the schematic representation of HLA-heterotrimers and HLA-open conformers (free-heavy chains). Both forms may exist at the cell surface of antigen presenting cells (APC cells). The inventors propose that the interaction of open conformers with immunoregulatory receptors (KIR's, LIL's, PTPRJ, etc.) is different in affinity and thus modified to induce immune responses that favour anti-tumor immunity.
Figure 3:
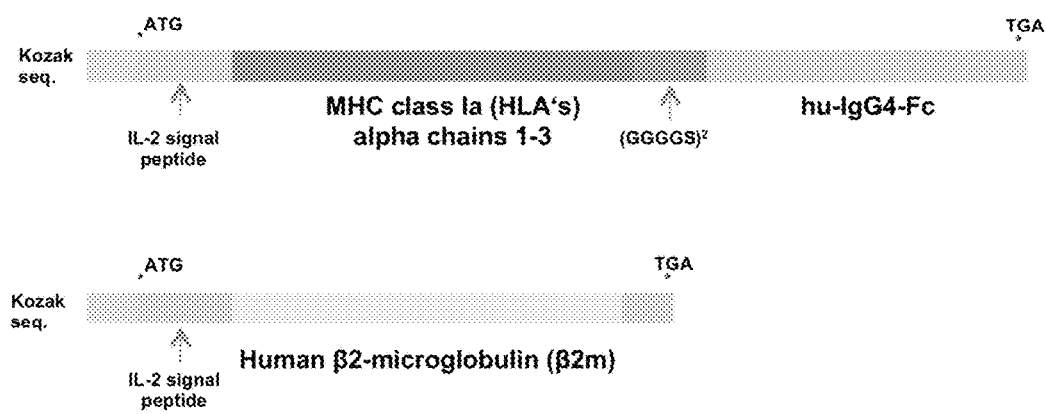
FIG. 3 shows the schematic representation of HLA-Fc and β2m DNA cassettes and expression of HLA-β2m-Fc molecules from CHO cells. A) alpha 1, 2 and 3 domains of MHC-Ia heavy chains (HLA-heavy chain) are inserted into a human IgG4-Fc vector cassette; and the human-β2 microglobulin inserted in a separate vector cassette. B) Transfections in Chinese hamster ovary cells (CHO) cells are performed using both the HLA-Fc-vector+β2m-vector at a ratio of 1:1 for the extracellular production of the HLA-β2m-Fc protein. Supernatants were collected and HLA-β2m-Fc purified using standard antibody purification protocols. β2m is removed from the HLA-β2m-Fc complex and following HLA-Fc monomers are refolded to form $HLA_2$-Fc homodimers.
Figure 3:
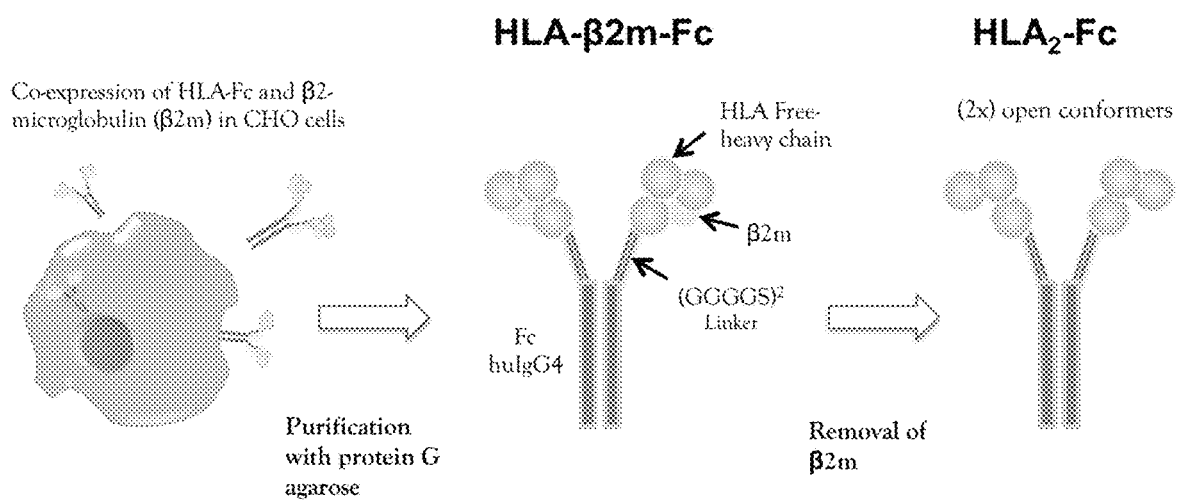
Figure 4:
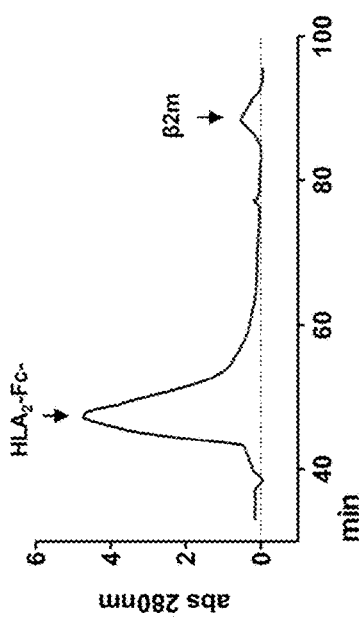
FIG. 4 shows the separation of β2m from the HLA-β2m-Fc complex and purification and refolding of $HLA_2$-Fc by SEC. A) Chromatography histogram plot of HLA-β2m-Fc molecules in Urea-Tris-BME denaturing buffer show the dissociation of HLA-Fc-free heavy chains from β2m using Sephacryl S-100 HR columns by SEC. B) and C) SDS-page gels stained with coomassie blue show the presence of β2m before and after SEC. B) shows HLA-B2m-Fc molecules before being separated in SEC, and C) show $HLA_2$-Fc molecules recovered and re-folded following SEC.
Figure 4:
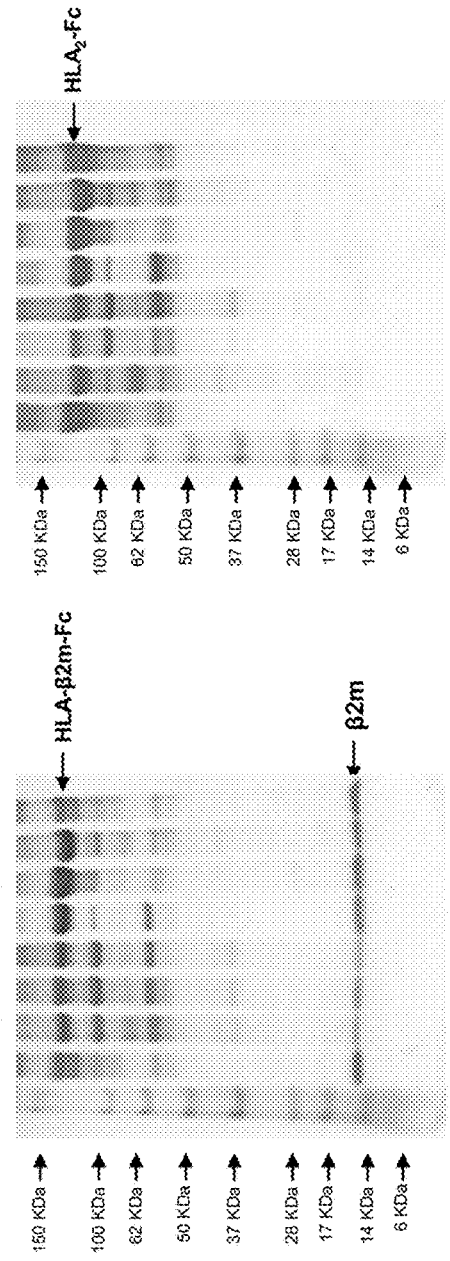

A valid strategy, from a therapeutic point of view, is to produce MHC-Ia open conformers molecules in stable format (Fc fusion), to increase solubility, stability, avidity, half-life, and from a technological point of view, cost-effective production and purification in mammalian systems. HLA-β2m-Fc complex was successfully produced by inserting the alpha 1, 2 and 3 domains of HLA-A25, HLA-A30, HLA-B27, HLA-B53, HLA-B57, HLA-B58, HLA-008 and HLA-C12 into a human IgG4-Fc vector cassette (FIG. 3A), together with a human-β2m vector, necessary for extracellular production of the HLA-β2m-Fc protein (FIG. 3A,B). Transfections in Chinese hamster ovary cells (CHO) cells were performed using both the HLA-Fc-vector+β2m-vector at a ratio of 1:1. Supernatants were collected and HLA-β2m-Fc purified using standard antibody purification protocols (Recombinant Protein Purification Handbook, principles and methods. 2009. GE Healthcare, 18-1142-75). Separation of β2m from HLA-Fc free-heavy chains was performed using denaturing conditions by SEC (FIG. 4A), or dialysis (data not shown). Refolding of HLA$_2$-Fc was assessed using the dilution method in refolding buffer and analysed SDS page (FIG. 4B,C) or by western blot (data not shown).

Pre-Clinical Combination Therapy Tests of HLA$_2$-Fc with CTLA4 and PD-1 Antibodies in Murine Syngeneic Colon Cancer Models The in vivo proof of concept study using HLA$_2$-Fc (A30$_2$-Fc, B27$_2$-Fc, B57$_2$-Fc, B58$_2$-Fc, and C08$_2$-Fc) as immunomodulatory therapeutic molecules was demonstrated in the C38 and MC38-OVA murine colon carcinoma cancer models as monotherapy or in combination with a murine CTLA4 or murine PD-1 antibody.

Following established protocols C38 or MC38-OVA fragment tumours were subcutaneously injected in the flank of syngeneic mice. Once the tumour reached 60 mm$^3$ (between 1-2 weeks after transplantation of tumors), mice were distributed according to their tumor volume. A30$_2$-Fc, B27$_2$-Fc, B57$_2$-Fc, B58$_2$-Fc, and C08$_2$-Fc was injected i.p. six times every 3$^{rd}$ day (Q3Dx6), CTLA4 was injected two times (Q3Dx2), and PD-1 injected 4 times twice a week (biwkx2) (FIG. 8A).

Figure 9:
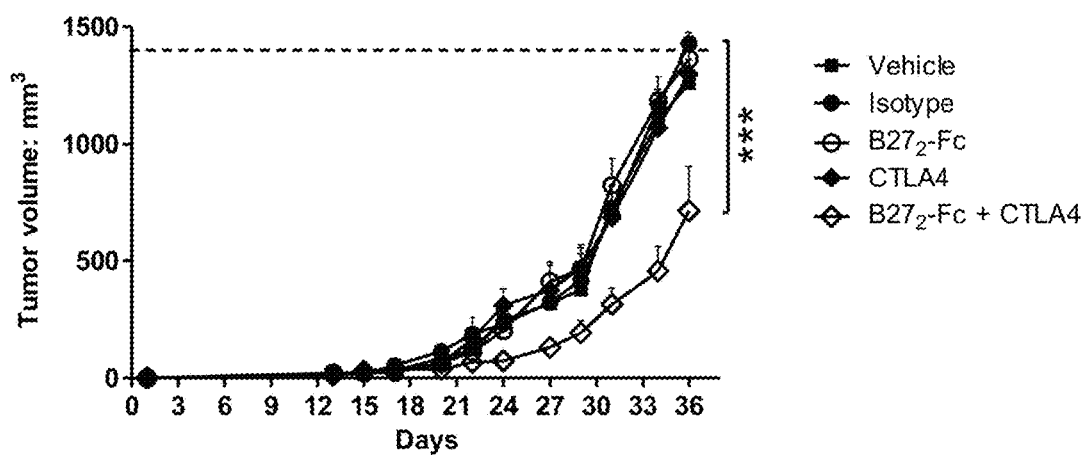
FIG. 9 shows that $HLA_2$-Fc ($B27_2$-Fc and $B57_2$-Fc) in combination with CTLA4 or PD-1 antibodies reduce the size of tumors in the MC38-OVA or C38 murine syngeneic colon carcinoma model. A) Mean average tumor volume $mm^3$ of B272-Fc treated groups (n=6). B) Mean average tumor volume $mm^3$ of B572-Fc treated groups (n=6). The experimental design of injection time points of cells and injection of substances was as follow: vehicle PBS Q3Dx6, isotype (10 mg/Kg) Q3Dx6; $HLA_2$-Fc (10 mg/Kg) Q3Dx6; CTLA-4 Q3Dx2 (d1=100 µg; d4=50 µg), PD-1 biwk×2 (200 µg); $HLA_2$-Fc+CTLA-4 (Q3Dx6 & Q3Dx2, respectively), and $HLA_2$-Fc+PD-1 (Q3Dx6 & biwk×2, respectively). Tumor volumes are expressed as mean±SEM and analysed by two-way ANOVA followed by Bonferroni post-hoc analysis, p<0.01, *p<0.001, n.s.=not significant. Q=days between injections; Dx=number of injections; biwk=twice a week.
Figure 9:
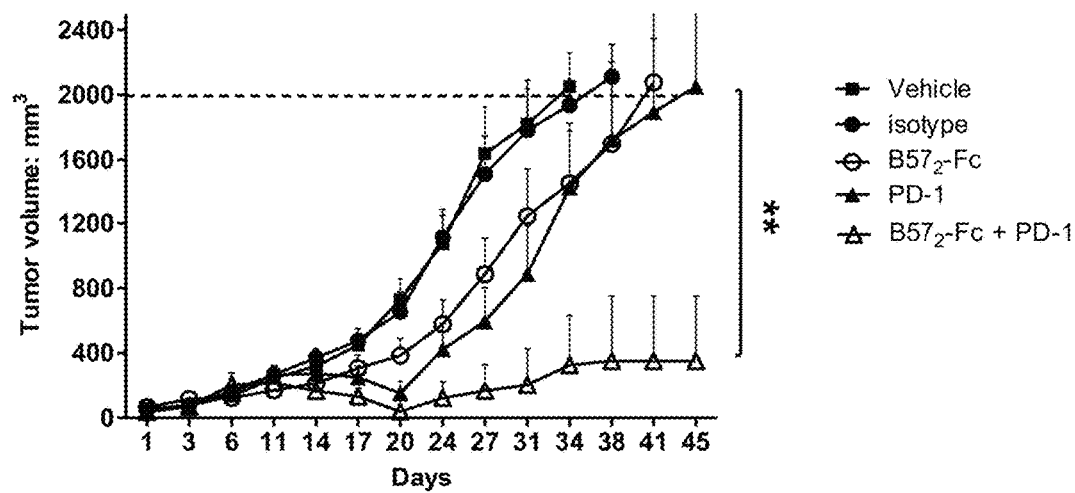

Selected HLA$_2$-Fc can synergize and enhance anti-tumor responses in syngeneic C38 and MC38-OVA colon cancer mouse models (FIGS. 8 & 9) either as monotherapy (C08$_2$-Fc) (FIG. 8D) or in combination with checkpoint antibodies, such as PD-1+A30$_2$-Fc (FIG. 8B), B58$_2$-Fc (FIG. 8C), B57$_2$-Fc (FIG. 9B) and CTLA4+B27$_2$-Fc (FIG. 9A).

Pre-Clinical Combination Therapy Tests of HLA$_2$-Fc with PD-1 and 4-1BB Antibodies in Large Tumors of a Murine Syngeneic Pancreatic Cancer Model For the pancreas (Pan02) cancer mouse model, following established protocols Pan02 cells were injected at 1×10$^5$ in the right flank of syngeneic mice respectively. Once the tumors had reached 300 mm3 (approximately 3 weeks after injection of cells) mice were statistically distributed according to their tumor volume. To note that large tumors are harder to treat than smaller tumors, but are useful for further analysis of tumor infiltrating lymphocytes (TILs). Furthermore large tumors are closer to a clinical setting where interventions with immunomodulators are performed in large size tumors of patients.

In pancreas (Pan02) data demonstrated that HLA$_2$-Fc combination with PD-1 antibody can significantly reduce large Pan02 tumors in combination with A25$_2$-Fc (FIG. 10A-B), B27$_2$-Fc (FIG. 16A-B), C08$_2$-Fc (FIG. 28A-B), and C12$_2$-Fc (FIG. 31A-B), whereas PD-1 monotherapy showed no therapeutic effect. Other HLA$_2$-Fc combinations with PD-1 did not demonstrate statistical significance, however % Δtumor inhibition was observed in combination B57$_2$-Fc (FIG. 22). Additionally, combo therapy of HLA$_2$-Fc with 4-1BB antibody demonstrated to significantly reduce the tumor size or several HLA$_2$-Fc combo therapies (for exception of A30$_2$-Fc and C08$_2$-Fc) when compared to isotype. The most striking tumor reductions (p<0.01) were observed with B53$_2$-Fc (FIG. 19A-B), B57$_2$-Fc (FIG. 22A-B), and B58$_2$-Fc (FIG. 25A-B). 4-1 BB monotherapy was not significantly different when compared to isotype control. Monotherapy with C08$_2$-Fc (FIG. 28A-B) showed significant tumor reduction (p<0.01) compared to isotype.

The tumor immune contexture of pancreas (Pan02) mice demonstrated the influence of HLA$_2$-Fc therapy towards diverse sets of tumor infiltrating leukocytes as observed with the infiltration of macrophages M1/M2 ratio, increased NK cells, NKT cells, CD3+ T cells, and CD8+ T cells, and reduction of MDSCs, with variations for each HLA$_2$-Fc as observed in A25$_2$-Fc (FIG. 11A-C), A30$_2$-Fc (14A-C), B27$_2$-Fc (17A-C), B53$_2$-Fc (20A-C), B57$_2$-Fc (23A-C), B58$_2$-Fc (26A-C), C08$_2$-Fc (29A-C), and C12$_2$-Fc (32A-C). Systemically analysis of leukocytes from the blood demonstrated only few changes when compared to their control monotherapy counterparts in NKT cells and Th1 cells for some cases, A25$_2$-Fc (FIG. 12A-C), A30$_2$-Fc (15A-C), B27$_2$-Fc (18A-C), B53$_2$-Fc (21A-C), B57$_2$-Fc (24A-C), B58$_2$-Fc (27A-C), C08$_2$-Fc (30A-C), and C12$_2$-Fc (33A-C).

CONCLUSION

The present invention demonstrates for the first time that the family of classical MHC-Ia molecules when produced as heavy chains without β2m (HLA-A, HLA-B and HLA-C open conformers and their corresponding HLA$_2$-Fc fusion proteins) have immunomodulatory properties that differ from their control HLA-β2m counterparts. Using as non-limiting examples diverse sets of HLA alleles the inventors provide data demonstrating that invariably MHC-Ia molecules, when present as open conformers are immunomodulatory agents with unique properties as demonstrated by the modulation of leukocytes present in the tumor microenvironment and in the blood. Furthermore its use is not only limited to modulatory agents, but also for its use as therapeutics for the treatment of cancer as demonstrated in pre-clinical cancer mouse models of colon cancer and pancreatic cancer either as monotherapy or in combination therapy with checkpoint inhibitor antibodies (e.g. CTLA4 and PD-1) and checkpoint agonistic antibodies (e.g. 4-1 BB).

Interaction of HLA$_2$-Fc with diverse immunoregulatory receptors (KIR3DL1, KIR3DL2, KIR3DL3, LILRB1, LILRB2, PTPRJ and Pirb) distributed in diverse white blood cells (e.g. NK, NKT, CD4+ T-cells, macrophages and MDSCs) demonstrates that the multitasking nature of the molecules paves a new way of modulating the immune system with HLA open conformers.

Additionally, HLA$_2$-Fc molecules demonstrated to block the conversion of naïve CD4+ T-cells to iTregs in vitro, pointing out to a mode of action were HLA$_2$-Fc acts as an immunomodulatory molecule affecting the differentiation and function of iTregs. Targeting iTregs is a strategy for diverse therapeutic indications, such as infectious diseases and cancer.

Overall, the mode of action of HLA$_2$-Fc as combinatorial approaches with antagonistic/agonistic antibodies is of undoubted relevance in the treatment of cancer, and correlates to the current clinical need in cancer immunotherapy.

HLA$_2$-Fc molecules emerge as a novel class of immunomodulatory drugs. In vitro and in vivo data points to a mechanism were HLA$_2$-Fc molecules act as a switch-on mechanism for the activation of anti-tumor immunity. Without wishing to be bound by theory, the inventors hypothesize that the interaction of HLA$_2$-Fc open conformers with diverse immunomodulatory receptors present in NK, T cells, macrophages and MDSCs, and functional modulation of Tregs participate synergistically and exacerbates the immune response.

Materials and Methods

Cell Lines

In vivo experiments were performed using C38 and MC38-OVA colon carcinoma mouse cell lines.

In vitro experiment cell lines used were: EL4, mouse T cell lymphoma; EG.7, mouse T cell lymphoma; Jurkat, human T cell lymphoma; L428, human Hodgkin lymphoma; L540, human Hodgkin lymphoma; L1236, human Hodgkin lymphoma; Daudi, B cell lymphoma; IMR-5, neuroblastoma; SK-N-AS, neuroblastoma; and M130428, Melanoma.

Antibodies

Lymphocytes populations for iTreg conversion experiments were stained with: CD4 (FITC-BD Bioscience), FoxP3+(efluor 450-eBioscience), CD3 (PE-Cy7-eBioscience), CD45 (PerCP-eBioscience).

Analysis of tumor infiltrating lymphocytes was performed with the following antibodies: CD45 (Biolegend, clone 30-F11); CD3 (BD Bioscience, clone 145-2C11); CD4 (Biolegend, clone GK1.5), CD8 (BD Bioscience, clone 53-6.7), CD25 (Biolegend, clone PC61), FoxP3 (eBioscience, clone FJK-16s), CD335 (Biolegend, clone 29A1.4), F4/80 (Biolegend, clone BM8), CD11 b (Biolegend, clone M1/70), Gr-1 (BD Bioscience, clone RB6-8C5), MHCII I-A/I-E (BD Bioscience, clone 2G9), CD206 (Biolegend, clone C068C2) and L/D stain (eBioscience).

Analysis of blood leukocytes was performed with the following antibodies: CD45 (Biolegend, clone 30-F11); CD3 (BD Bioscience, clone 145-2C11), CD4 (Biolegend, clone GK1.5), CD8 (BD Bioscience, clone 53-6.7), FoxP3 (eBioscience, clone FJK-16s), T-Bet (BD Bioscience, clone 4610), CD335 (Biolegend, clone 29A1.4), F4/80 (Biolegend, clone BM8), CD115 (Biolegend, clone AFS98), CD11b (Biolegend, clone M1/70), Ly6G (Biolegend, clone 1A8), Ly6C (Biolegend, clone HK1.4) and L/D stain (eBioscience).

Checkpoint inhibitor antibodies CTLA4 clone 9H10, PD-1 clone RMP1-14, and agonist antibody 4-1 BB clone 3H3 were obtained from Bio X Cell Co.

HC10 mAb (IgG2a) binding to $\beta$2m-free heavy chains of MHC-Ia alleles was a gift from Dr. Hidde Ploegh (MIT, MA).

Production, Purification and Re-Folding of $HLA_2$-Fc

Recombinant production of HLA-$\beta$2m-Fc (A25-$\beta$2m-Fc, A30-$\beta$2m-Fc, B2705-$\beta$2m-Fc, B53-$\beta$2m-Fc, B57-$\beta$2m-Fc, B58-$\beta$2m-Fc, C08-$\beta$2m-Fc & 012-$\beta$2m-Fc) was achieved by inserting the alpha 1, 2 and 3 domains of HLAs into a human IgG4-Fc vector (InvivoGen), and the human $\beta$2-microglobulin ($\beta$2m) in a separate vector. Production of recombinant HLA-$\beta$2m-Fc was performed by co-transfection of the HLA-Fc-vector sand $\beta$2m-vector into Chinese hamster ovary (CHO) cells. Production of HLA-$\beta$2m-Fc was outsourced to Evitria AG.

Purification of HLA-$\beta$2m-Fc constructs was performed using conventional protocols for antibody purification. Production of $HLA_2$-Fc was performed with the addition of a denaturing step to remove $\beta$2m from the HLA-$\beta$2m-Fc complex.

Briefly, the capture step of HLA-$\beta$2m-Fc proteins was performed after running supernatants (5 mL/min) through protein-G columns (Amersham Pharmacia). Intermediate purification steps were performed by eluting the selected HLA-$\beta$2m-Fc from protein G-columns using elution buffer (100 mM glycine, pH 2.0), and recovering fractions in 8M Urea, 100 mM Tris-HCl pH 8.0. The $1^{st}$ Polishing step was to separate HLA-Fc monomers fractions from $\beta$2m by either size exclusion chromatography (SEC) using superdex 200 prep grade or Sephacryl S-100 HR (GE Lifescience) with an ÄKTA system (GE Lifescience), or by dialysis with membranes of 50 KDa pore size (Millipore). The recovered HLA-Fc monomers from both protocols were re-folded by the dilution method after pulsation of the HLA-Fc monomers at 3 times with intervals of 8 hours each in 100 times volume of refolding buffer (50 mM Tris-HCl pH8.5, 500 mM L-Arginine, 1 mM EDTA, 0.15 mM NaCl, 1% Sucrose, 0.01% Tween-20). The $2^{nd}$ Polishing step by SEC was performed to remove further impurities and to buffer exchange newly recovered fractions of $HLA_2$-Fc proteins into dilution buffer (PBS, 1% Sucrose, and 0.01% Tween-20). Purified solutions of $HLA_2$-Fc proteins ($A25_2$-Fc, $A25_2$-Fc, $B2705_2$-Fc, $B53_2$-Fc, $B57_2$-Fc, $B58_2$-Fc, $C08_2$-F, $C12_2$-Fc) were filter sterilized using 0.2 μm membranes (Millipore).

Fractions HLA-$\beta$2m-Fc complexes and $HLA_2$-Fc were analysed by gradient 4-20% SDS polyacrylamide gel electrophoresis (SDS-PAGE) and western blot using HC10 (specific for HLA-free-heavy chains) antibodies. $\beta$2m western blots were performed with and without denaturing conditions (10 mM DTT) (data not shown).

ELISA Assays

Competition ELISA assays were performed using Maxisorp (Nunc, Switzerland) 96 well plates coated with 10 μg/mL of selected leukocyte receptors (human KIR3DL1, human KIR3DL2, human KIR3DL3, human LILRB1, human LILRB2, human PTPRJ and mouse Pirb) purchased from Creative Biomart. Receptors were incubated for ON 4° C., blocked with 5% milk powder-TBS 2 hrs. $HLA_2$-Fc selected constructs ($A25_2$-Fc, $A30_2$-Fc, $B2705_2$-Fc, $B53_2$-Fc, $B57_2$-Fc, $B58_2$-Fc, $C08_2$-F, and $C12_2$-Fc) and their controls (A25-$\beta$2m-Fc, A30-$\beta$2m-Fc, B2705132m-Fc, B53-$\beta$2m-Fc, B57-$\beta$2m-Fc, B58-$\beta$2m-Fc, C08-$\beta$2m-Fc and 012-$\beta$2m-Fc) and isotype IgG4 were added at 10 μg/mL for 2 hrs RT. HRP-conjugated antibodies against human Fc were used as detectors.

Flow Cytometry of Leukocytes

Flow cytometry analysis was performed using a FACS canto II (BD Bioscience) and data were analysed using FlowJo version 7.6.4.

Generation of Tregs

To induce expression of Foxp3 in murine $CD4^+$ T cells, we harvested spleen cells from C57BL/6 splenocytes and purified (Mouse Naïve $CD4^+$ T Cell Isolation Kit-Easy Sep) to obtain $CD4^+$ T naive cells. Cells were then cultured for 96 h at $10^5$ cells/200 μL/well in 96-well plates with coated 5 μg/mL anti-CD3mAb (eBioscience), soluble 2 μg/mL anti-CD28 mAb (Biolegend), 10 μg/mL of TGF-$\beta$1 (R&D systems) and 100 IU/mL of IL-2 (R&D systems).

iTreg Conversion in the Presence of $HLA_2$-Fc

Murine naive CD4+ T cells in optimal culture conditions for iTreg conversion were incubated in the presence at dose concentrations (5 μg/200 μL) of $HLA_2$_Fc ($A25_2$-Fc, $A30_2$-Fc, $B2705_2$-Fc, $B53_2$-Fc, $B57_2$-Fc, $B58_2$-Fc, $C08_2$-F, and $C12_2$-Fc), controls (A25-$\beta$2m-Fc, A30-$\beta$2m-Fc, B2705-$\beta$2m-Fc, B53-$\beta$2m-Fc, B57-$\beta$2m-Fc, B58-$\beta$2m-Fc, C08-$\beta$2m-Fc and C12-$\beta$2m-Fc) Isotype IgG4, media without differentiation factors and PBS for 72 h. iTreg conversion was measured by flow cytometry.

Proliferation Assay

Cells were plated in round 96-wells plates at a density of $5 \times 10^5$ cells/well following the addition of drugs at different concentrations (25, 10, and 5 μg/well) for 1 day. XTT proliferation assay was performed accordingly to the manual instructions (cell proliferation kit II, Roche). Results were obtained with the absorbance of wells at 450 nm using a microtiter plate reader.

In Vivo Treatments

C38 or MC38-OVA tumour fragments were injected subcutaneously into the right flanks of syngeneic female C57BL/6 mice at week 6. Pan02 cell lines were injected at $1 \times 10^5$ in the right flank of syngeneic mice C57BL/6 at week 6. Animals were distributed according to their individual tumour volume size and divided into groups displaying no statistical differences between them. For C38 and MC38-

OVA experimental treatment began when the tumors had reach ±60 mm$^3$. For pancreas Pan02 experimental treatment began in large tumors of 300 mm$^3$. Tumour diameters were measured using a caliper, and volume was calculated according to the formula, $D/2 \times d^2$ where D and d are the longest and shortest diameter of the tumour in mm, respectively.

The Experimental design of injection of substances was established as follow for colon (C38 and MC38): vehicle (PBS 200 µL) Q3Dx6; isotype (10 mg/Kg) Q3Dx6; HLA$_2$-Fc (10 mg/Kg) Q3Dx6; anti-CTLA4 Q3Dx2 (1st injection 100 µg and 2$^{nd}$ injection 50 µg); PD-1 biwkx2 (200 µg); HLA$_2$-Fc+CTLA-4 (Q3Dx6 and Q3Dx2, respectively); HLA$_2$-Fc+PD-1 (Q3Dx6 and biwkx2, respectively). For pancreas (Pan02) the experimental design of injection of substances was as follow: isotype (5 mg/Kg) biwkx2; HLA$_2$-Fc (5 mg/Kg) biwkx2; PD-1 (5 mg/Kg) biwkx2; 4-1 BB (1 mg/Kg) biwkx2; HLA$_2$-Fc+PD-1 biwkx2; and HLA$_2$-Fc+4-1 BB biwkx2.

% ΔInhibition is calculated from the ΔT/ΔC tumor growth ratio, which represents the growth of the tumor in % from the beginning of the treatment (e.g. 300 mm3), to the end volume of the treatment (e.g. 1000 mm3) compared to control using the following formula: Mean % ΔInhibition= (mean(C)−mean(C0))−(mean(T)−mean(T0))/(mean(C)−mean(C0))*100%. Where T=treated group value, T0—treated group initial value; C—control group value, C0—control group initial value.

For the analysis of tumor infiltrating lymphocytes the following gating strategies where used: CD45+ for total leukocytes; CD45+ CD3+ for total T cells; CD45+ CD3+ CD4+ for CD4 T helper cell; CD45+ CD3+ CD8+ for CD8 Cytotoxic T cell; CD45+ CD3+ CD4+ FoxP3+CD25+ for Treg cell; CD45+ CD3− CD11+ Gr-1+ for MDSCs; CD45+ CD3− CD11+ F4/80+ for Macrophages; CD45+ CD3− CD11+ F4/80+ MHCII+ for M1-type macrophages; CD45+ CD3− CD11+ F4/80+ CD206+ for M2-type macrophages; CD45+ Gr-1− F4/80− CD335+ for NK cells; and CD45+ Gr-1− F4/80− CD335+ CD3+ for NKT cells.

For the analysis of blood leukocytes the following gating strategies where used: CD45+ for total leukocytes; CD45+ CD3+ for total T cells; CD45+ CD3+ CD4+ for CD4 T helper cell; CD45+ CD3+ CD8+ for CD8 Cytotoxic T cell; CD45+ CD3+ CD4+ FoxP3+ for Treg cell; CD45+ CD3+ CD4+ T− Bet+ for Th1 cells; CD45+ CD3− CD11+ Ly6C+ Ly6G+ for G-MDSCs and M-MDSCs; CD45+ Ly6C− Ly6G− CD335+ for NK cells; and CD45+ Ly6C− Ly6G− CD335+CD3+ for NKT cells.

Preparation of tumor and blood samples for flow cytometry were performed using protocols described by eBioscience (https://www.ebioscience.com/media/pdf/best-protocols/cell-preparation-for-flow-cytometry.pdf, accessed Feb. 21, 2017).

TABLE 1

List of MHC-Ia alleles

| HLA-A | HLA-B | HLA-B | HLA-C |
|---|---|---|---|
| A*01 | B*07 | B*53 | C*01 |
| A*02 | B*08 | B*54 | C*02 |
| A*03 | B*13 | B*55 | C*03 |
| A*11 | B*14 | B*56 | C*04 |
| A*23 | B*15 | B*57 | C*05 |
| A*24 | B*18 | B*58 | C*06 |
| A*25 | B*27 | B*59 | C*07 |
| A*26 | B*35 | B*67 | C*08 |
| A*29 | B*37 | B*73 | C*12 |
| A*30 | B*38 | B*78 | C*14 |
| A*31 | B*39 | B*81 | C*15 |
| A*32 | B*40 | B*82 | C*16 |
| A*33 | B*42 | B*83 | C*17 |
| A*34 | B*44 | | C*18 |
| A*36 | B*46 | | |
| A*43 | B*47 | | |
| A*66 | B*48 | | |
| A*68 | B*49 | | |
| A*69 | B*50 | | |
| A*74 | B*51 | | |
| A*80 | B*52 | | |

TABLE 2

Selected MHC-Ia alleles

| Sequence identifier (length in aa) | Amino acid sequence |
|---|---|
| A*25:01:01 HLA00071 (365 aa) SEQ ID NO. 002 | MAVMAPRTLVLLLSGALALTQTWAGSHSMRYFYTSVSRPGRGEPRFIAVGYVD DTQFVRFDSDAASQRMEPRAPWIEQEGPEYWDRNTRNVKAHSQTDRESLRIAL RYYNQSEDGSHTIQRMYGCDVGPDGRFLRGYQQDAYDGKDYIALNEDLRSWTA ADMAAQITQRKWETAHEAEQWRAYLEGRCVEWLRRYLENGKETLQRTDAPKTH MTHHAVSDHEATLRCWALSFYPAEITLTWQRDGEDQTQDTELVETRPAGDGTF QKWASVVVPSGQEQRYTCHVQHEGLPKPLTLRWEPSSQPTIPIVGIIAGLVLF GAVIAGAVVAAVMWRRKSSDRKGGSYSQAASSDSAQGSDMSLTACKV |
| A*30:01:01 HLA00089 (365 aa) SEQ ID NO. 003 | MAVMAPRTLLLLLSGALALTQTWAGSHSMRYFSTSVSRPGSGEPRFIAVGYVD DTQFVRFDSDAASQRMEPRAPWIEQERPEYWDQETRNVKAQSQTDRVDLGTLR GYYNQSEAGSHTIQIMYGCDVGSDGRFLRGYEQHAYDGKDYIALNEDLRSWTA ADMAAQITQRKWEAARWAEQLRAYLEGTCVEWLRRYLENGKETLQRTDPPKTH MTHHPISDHEATLRCWALGFYPAEITLTWQRDGEDQTQDTELVETRPAGDGTF QKWAAVVVPSGEEQRYTCHVQHEGLPKPLTLRWELSSQPTIPIVGIIAGLVLL GAVITGAVVAAVMWRRKSSDRKGGSYTQAASSDSAQGSDVSLTACKV |

TABLE 2-continued

Selected MHC-Ia alleles

| Sequence identifier (length in aa) | Amino acid sequence |
|---|---|
| B*27:05:02 HLA00225 (362 aa) SEQ ID NO. 004 | MRVTAPRTLLLLLWGAVALTETWAGSHSMRYFHTSVSRPGRGEPRFITVGYVD DTLFVRFDSDAASPREEPRAPWIEQEGPEYWDRETQICKAKAQTDREDLRTLL RYYNQSEAGSHTLQNMYGCDVGPDGRLLRGYHQDAYDGKDYIALNEDLSSWTA ADTAAQITQRKWEAARVAEQLRAYLEGECVEWLRRYLENGKETLQRADPPKTH VTHHPISDHEATLRCWALGFYPAEITLTWQRDGEDQTQDTELVETRPAGDRTF QKWAAVVVPSGEEQRYTCHVQHEGLPKPLTLRWEPSSQSTVPIVGIVAGLAVL AVVVIGAVVAAVMCRRKSSGGKGGSYSQAACSDSAQGSDVSLTA |
| B*53:01:01 HLA00364 (362 aa) SEQ ID NO. 005 | MRVTAPRTVLLLLWGAVALTETWAGSHSMRYFYTAMSRPGRGEPRFIAVGYVD DTQFVRFDSDAASPRTEPRAPWIEQEGPEYWDRNTQIFKTNTQTYRENLRIAL RYYNQSEAGSHIIQRMYGCDLGPDGRLLRGHDQSAYDGKDYIALNEDLSSWTA ADTAAQITQRKWEAARVAEQLRAYLEGLCVEWLRRYLENGKETLQRADPPKTH VTHHPVSDHEATLRCWALGFYPAEITLTWQRDGEDQTQDTELVETRPAGDRTF QKWAAVVVPSGEEQRYTCHVQHEGLPKPLTLRWEPSSQSTIPIVGIVAGLAVL AVVVIGAVVATVMCRRKSSGGKGGSYSQAASSDSAQGSDVSLTA |
| B*57:01:01 HLA00381 (36 2aa) SEQ ID NO. 006 | MRVTAPRTVLLLLWGAVALTETWAGSHSMRYFYTAMSRPGRGEPRFIAVGYVD DTQFVRFDSDAASPRMAPRAPWIEQEGPEYWDGETRNMKASAQTYRENLRIAL RYYNQSEAGSHIIQVMYGCDVGPDGRLLRGHDQSAYDGKDYIALNEDLSSWTA ADTAAQITQRKWEAARVAEQLRAYLEGLCVEWLRRYLENGKETLQRADPPKTH VTHHPISDHEATLRCWALGFYPAEITLTWQRDGEDQTQDTELVETRPAGDRTF QKWAAVVVPSGEEQRYTCHVQHEGLPKPLTLRWEPSSQSTVPIVGIVAGLAVL AVVVIGAVVAAVMCRRKSSGGKGGSYSQAACSDSAQGSDVSLTA |
| B*58:01:01:01 HLA00386 (362 aa) SEQ ID NO. 007 | MRVTAPRTVLLLLWGAVALTETWAGSHSMRYFYTAMSRPGRGEPRFIAVGYVD DTQFVRFDSDAASPRTEPRAPWIEQEGPEYWDGETRNMKASAQTYRENLRIAL RYYNQSEAGSHIIQRMYGCDLGPDGRLLRGHDQSAYDGKDYIALNEDLSSWTA ADTAAQITQRKWEAARVAEQLRAYLEGLCVEWLRRYLENGKETLQRADPPKTH VTHHPVSDHEATLRCWALGFYPAEITLTWQRDGEDQTQDTELVETRPAGDRTF QKWAAVVVPSGEEQRYTCHVQHEGLPKPLTLRWEPSSQSTIPIVGIVAGLAVL AVVVIGAVVATVMCRRKSSGGKGGSYSQAASSDSAQGSDVSLTA |
| C*08:01:01 HLA00445 (366 aa) SEQ ID NO. 008 | MRVMAPRTLILLLSGALALTETWACSHSMRYFYTAVSRPGRGEPRFIAVGYVD DTQFVQFDSDAASPRGEPRAPWVEQEGPEYWDRETQKYKRQAQTDRVSLRNLR GYYNQSEAGSHTLQRMYGCDLGPDGRLLRGYNQFAYDGKDYIALNEDLRSWTA ADTAAQITQRKWEAARTAEQLRAYLEGTCVEWLRRYLENGKKTLQRAEHPKTH VTHHPVSDHEATLRCWALGFYPAEITLTWQRDGEDQTQDTELVETRPAGDGTF QKWAAVVVPSGEEQRYTCHVQHEGLPEPLTLRWGPSSQPTIPIVGIVAGLAVL AVLAVLGAVMAVVMCRRKSSGGKGGSCSQAASSNSAQGSDESLIACKA |
| C*12:02:01 HLA00453 (366 aa) SEQ ID NO. 009 | MRVMAPRTLILLLSGALALTETWACSHSMRYFYTAVSRPGRGEPRFIAVGYVD DTQFVRFDSDAASPRGEPRAPWVEQEGPEYWDRETQKYKRQAQADRVSLRNLR GYYNQSEAGSHTLQRMYGCDLGPDGRLLRGYDQSAYDGKDYIALNEDLRSWTA ADTAAQITQRKWEAAREAEQWRAYLEGTCVEWLRRYLENGKETLQRAEHPKTH VTHHPVSDHEATLRCWALGFYPAEITLTWQRDGEDQTQDTELVETRPAGDGTF QKWAAVVVPSGEEQRYTCHVQHEGLPEPLTLRWEPSSQPTIPIVGIVAGLAVL AVLAVLGAVMAVVMCRRKSSGGKGGSCSQAASSNSAQGSDESLIACKA |

We claim:

1. A fusion MHC-Ia open conformer dimer comprising a first and a second monomer, wherein each monomer independently of the other monomer is or comprises a HLA heavy chain fusion polypeptide,
and wherein each HLA heavy chain fusion polypeptide comprises or consists essentially of
a HLA heavy chain polypeptide comprising or consisting of a HLA alpha 1, 2 and 3 domain of a HLA heavy chain selected from A25, B58, C08, A30, B53, or C12, and
wherein said HLA heavy chain fusion polypeptide is covalently linked to an Fc polypeptide sequence, and
wherein the HLA heavy chain fusion polypeptide is not associated with an antigen peptide either as a monomer or as a dimer.

2. The fusion MHC-Ia open conformer dimer according to claim 1, wherein an amino acid linker joins the HLA-heavy chain polypeptide and the Fc polypeptide sequence.

3. The fusion MHC-Ia open conformer according to claim 1, wherein the first and the second monomer are the same.

4. The fusion MHC-Ia open conformer dimer according to claim 1, wherein the HLA-heavy chain polypeptide consists of the HLA alpha 1, 2 and 3 domains of the HLA heavy chain.

5. The fusion MHC-Ia open conformer dimer according to claim 1, wherein the HLA-heavy chain polypeptide comprises the transmembrane domain and does not comprise the intracellular domain.

6. The fusion MHC-Ia open conformer dimer according to claim 1, wherein the Fc polypeptide sequence comprises a heavy chain constant region $C_H2$ and $C_H3$ selected from any one of immunoglobulin type G (IgG), type A (IgA), type D (IgD), type E (IgE) or type M (IgM).

7. The fusion MHC-Ia open conformer dimer according to claim 1, wherein the amino acid linker comprises 1 to 50 amino acids linking the HLA-heavy chain polypeptide to the Fc polypeptide sequence as one single polypeptide chain.

8. A nucleic acid molecule encoding the HLA heavy chain fusion polypeptide of claim 1.

9. A virus comprising a nucleic acid molecule of claim 8 under control of a promoter sequence operable in a mammalian cell, wherein the virus is an adenovirus, adeno-associated virus, a herpes virus or a lentivirus.

10. An in vitro genetically modified host cell comprising the nucleic acid molecule of claim 8.

11. A combination medicament comprising:
  a) the fusion MHC-Ia open conformer dimer as specified in claim 1, and
  b) a checkpoint modulatory agent selected from the group consisting of:
    i) a checkpoint inhibitory agent (CPI) selected from the group consisting of:
      an inhibitor of the interaction of CTLA4 with either B7-1 (cd80) and/or B7-2 (cd86);
      an inhibitor of the interaction of PD-1 with either PD-L1 and/or PD-L2; and
      an inhibitory polypeptide ligand of T cell immunoglobulin and mucin domain-containing 3 (TIM-3); and
    ii) a checkpoint agonist antibody selected to bind to and activate the tumor necrosis factor receptor 4-1BB,
  wherein said checkpoint modulatory agent is a polypeptide selected from an antibody, an antibody fragment, and an antibody-like molecule, and the polypeptide is selectively reactive to a checkpoint mediator selected from CTLA4, PD-1, CD80, CD86, PD-L1, PD-L2, TIM-3, 4-1BB and 4-1BBL.

12. The fusion MHC-Ia open conformer dimer according to claim 1, wherein the A25, B58, C08, A30, B53, and C12 HLA heavy chain sequences are respectively SEQ ID NO: 002, SEQ ID NO: 007, SEQ ID NO: 008, SEQ ID NO: 003, SEQ ID NO: 005, and SEQ ID NO: 009.

13. The fusion MHC-Ia open conformer dimer according to claim 7, wherein the amino acid linker comprises 5 to 40 amino acids linking the HLA-heavy chain polypeptide to the Fc polypeptide sequence as one single polypeptide chain.

14. The fusion MHC-Ia open conformer dimer according to claim 7, wherein the amino acid linker comprises 10 to 30 amino acids, linking the HLA-heavy chain polypeptide to the Fc polypeptide sequence as one single polypeptide chain.

15. The fusion MHC-Ia open conformer dimer according to claim 7, wherein the amino acid linker comprises 15 to 25 amino acids linking the HLA-heavy chain polypeptide to the Fc polypeptide sequence as one single polypeptide chain.

* * * * *